(12) United States Patent
Newman et al.

(10) Patent No.: US 12,097,196 B2
(45) Date of Patent: Sep. 24, 2024

(54) DOPAMINE D3 RECEPTOR SELECTIVE ANTAGONISTS/PARTIAL AGONISTS AND USES THEREOF

(71) Applicant: The United States of America, as Represented by the Secretary, Department of Health & Human Services, Bethesda, MD (US)

(72) Inventors: Amy Hauck Newman, Phoenix, MD (US); Vivek Kumar, Baltimore, MD (US); Anver Basha Shaik, Baltimore, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 126 days.

(21) Appl. No.: 17/738,301

(22) Filed: May 6, 2022

(65) Prior Publication Data
US 2022/0265643 A1 Aug. 25, 2022

Related U.S. Application Data

(63) Continuation of application No. 17/265,150, filed as application No. PCT/US2019/050165 on Sep. 9, 2019, now Pat. No. 11,337,971.

(60) Provisional application No. 62/729,709, filed on Sep. 11, 2018.

(51) Int. Cl.
*A61K 31/496* (2006.01)
*A61K 31/485* (2006.01)
*A61P 25/36* (2006.01)

(52) U.S. Cl.
CPC .......... *A61K 31/496* (2013.01); *A61K 31/485* (2013.01); *A61P 25/36* (2018.01)

(58) Field of Classification Search
CPC ..... A61K 31/496; A61K 31/485; A61P 25/04; A61P 25/18; A61P 25/30; A61P 25/36
USPC ............................................ 514/252.13, 282
See application file for complete search history.

(56) References Cited

U.S. PATENT DOCUMENTS

| | | | |
|---|---|---|---|
| 7,605,259 B2 | 10/2009 | Newman et al. | |
| 8,119,642 B2 | 2/2012 | Newman et al. | |
| 8,748,608 B2 | 6/2014 | Newman et al. | |
| 11,299,476 B2 * | 4/2022 | Newman | C07D 405/12 |
| 2005/0197343 A1 | 9/2005 | Gmeiner et al. | |
| 2006/0106030 A1 | 5/2006 | Newman et al. | |
| 2010/0068138 A1 | 3/2010 | Newman et al. | |
| 2014/0296249 A1 | 10/2014 | Newman et al. | |
| 2020/0291000 A1 | 9/2020 | Newman et al. | |
| 2021/0346373 A1 | 11/2021 | Newman et al. | |

FOREIGN PATENT DOCUMENTS

| | | |
|---|---|---|
| WO | 199731916 A1 | 9/1997 |
| WO | 199734889 A1 | 9/1997 |
| WO | 199806717 A1 | 2/1998 |
| WO | 03028728 A1 | 4/2003 |
| WO | 2004004729 A1 | 1/2004 |
| WO | 2004024878 A2 | 3/2004 |
| WO | 2006015737 A1 | 2/2006 |
| WO | 2006050976 A1 | 5/2006 |
| WO | 2006072608 A2 | 7/2006 |
| WO | 2008009741 A1 | 1/2008 |
| WO | 2014059265 A1 | 4/2014 |
| WO | 2017160552 A1 | 9/2017 |
| WO | 2020055725 A1 | 3/2020 |

OTHER PUBLICATIONS

Jordan, C.J. et al.: The highly selective dopamine D3R antagonist, R-VK4-40 attenuates oxycodone reward and au7gments analgesia in rodents. Neuropharmacology, vol. 158, pp. 107597, 2019.*
Simms et al., "In vivo characterization of a novel dopamine D3 receptor agonist to treat motor symptoms of Parkinson's disease," Neuropharmacology, vol. 100, 2016, pp. 106-115.
Veselinovic et al., "Cariprazine, a new, orally active dopamine D2/3 receptor partial agonist for the treatment of schizophrenia, bipolar mania and depression," Expert Reviews, Neurother., vol. 13, No. 11, 2013, pp. 1141-1159.
Shaik, Anver Basha, et al. "Investigation of novel primary and secondary pharmacophores and 3-substitution in the linking chain of a series of highly selective and bitopic dopamine D3 receptor antagonists and partial agonists." Journal of medicinal chemistry, (2019), vol. 62, No. 20: 9061-9077.
Kiss, Béla, et al. "Neuronal dopamine D3 receptors: translational implications for preclinical research and CNS disorders." Biomolecules, (2021), vol. 11, No. 104, pp. 1-39.
Laszlovszky, István, et al. "Cariprazine, a broad-spectrum antipsychotic for the treatment of schizophrenia: pharmacology, efficacy, and safety." Advances in Therapy, (2021), vol. 38, No. 7: 3652-3673.
Tohen, Mauricio. "Cariprazine as a Treatment Option for Depressive Episodes Associated with Bipolar 1 Disorder in Adults: An Evidence-Based Review of Recent Data." Drug Design, Development and Therapy 15, (2021): 2005-2012.

(Continued)

*Primary Examiner* — Charanjit Aulakh
(74) *Attorney, Agent, or Firm* — Leydig, Voit & Mayer, Ltd.

(57) ABSTRACT

Disclosed herein are novel methods of treating pain in a patient in need thereof by providing to the patient a selective dopamine D3 receptor antagonist/partial agonist which when used with an opioid analgesic, can mitigate the development of opioid dependence, by preventing the need for dose escalation while either maintaining the opioid analgesic effect or providing analgesia with a lower dose of the opioid. In addition, the D3 antagonists/partial agonists described herein may be used to augment the effectiveness of current Medication Assisted Treatment regimens (e.g. methadone or buprenorphine) for the treatment of opioid use disorders.

17 Claims, 9 Drawing Sheets

(56) References Cited

OTHER PUBLICATIONS

Maramai, Samuele, et al. "Dopamine D3 receptor antagonists as potential therapeutics for the treatment of neurological diseases." Frontiers in neuroscience, (2016), vol. 1 : 451, 16 pages.

Achat-Mendes, Cindy, et al. "Dopamine D3 and D2 receptor mechanisms in the abuse-related behavioral effects of cocaine: studies with preferential antagonists in squirrel monkeys." Journal of Pharmacology and Experimental Therapeutics, (2010), vol. 334, No. 2: 556-565.

Ananthan, Subramaniam, et al. "Design, synthesis, and structure-activity relationship studies of a series of [4-(4-carboxamidobutyl)]-1-arylpiperazines: Insights into structural features contributing to dopamine D3 versus D2 receptor subtype selectivity." Journal of medicinal chemistry, (2014), vol. 57, No. 16: 7042-7060.

Ashby, Charles R., et al. "Acute administration of the selective D3 receptor antagonist SB-277011A blocks the acquisition and expression of the conditioned place preference response to heroin in male rats." Synapse, (2003), vol. 48, No. 3: 154-156.

Azar, Marc R., et al. "Conditioned place aversion is a highly sensitive index of acute opioid dependence and withdrawal." Psychopharmacology, (2003), vol. 170, No. 1: 42-50.

Beaulieu, Jean-Martin, and Raul R. Gainetdinov. "The physiology, signaling, and pharmacology of dopamine receptors." Pharmacological reviews, (2011), vol. 63, No. 1: 182-217.

Brewer, Kori L., et al. "Dopamine D3 receptor dysfunction prevents anti-nociceptive effects of morphine in the spinal cord." Frontiers in Neural Circuits, (2014), 8: 62-64.

Chen, Jianyong, et al. "Tranylcypromine substituted cis-hydroxycyclobutylnaphthamides as potent and selective dopamine D3 receptor antagonists." Journal of medicinal chemistry, (2014), vol. 57, No. 11: 4962-4968.

Cummings, Jeffrey L., et al. "The role of dopaminergic imaging in patients with symptoms of dopaminergic system neurodegeneration." Brain, (2011), vol. 134, No. 11: 3146-3166.

Goldberg, Steven R. "Comparable behavior maintained under fixed-ratio and second-order schedules of food presentation, cocaine injection or d-amphetamine injection in the squirrel monkey." Journal of Pharmacology and Experimental Therapeutics, (1973), vol. 186, No. 1: 18-30.

Grundt, Peter, et al. "Novel heterocyclic trans olefin analogues of N-{4-[4-(2,3-dichlorophenyl)piperazin-1-yl]butyl} arylcarboxamides as selective probes with high affinity for the dopamine D3 receptor." Journal of medicinal chemistry, (2005), vol. 48, No. 3: 839-848.

Heidbreder, Christian A., et al. "The role of central dopamine D3 receptors in drug addiction: a review of pharmacological evidence." Brain Research Reviews, (2005), vol. 49, No. 1: 77-105.

International Search Report for International Application No. PCT/US2019/050165, International Filing Date Sep. 9, 2019, Date of Mailing Jan. 29, 2020, 7 pages.

Joyce, Jeffrey N., and Mark J. Millan. "Dopamine D3 receptor antagonists as therapeutic agents." Drug discovery today, (2005), vol. 10, No. 13: 917-925.

Justinova, Zuzana, et al. "Self-administration of delta9-tetrahydrocannabinol (THC) by drug naive squirrel monkeys." Psychopharmacology, (2003), vol. 169, No. 2: 135-140.

Kamal, Ahmed, et al. "Design and synthesis of pyrazole/isoxazole linked arylcinnamides as tubulin polymerization inhibitors and potential antiproliferative agents." Organic & Biomolecular Chemistry, (2015), vol. 13, No. 40: 10162-10178.

Keck, Thomas M., et al. "Identifying medication targets for psychostimulant addiction: unraveling the dopamine D3 receptor hypothesis." Journal of medicinal chemistry, (2015), vol. 58, No. 14: 5361-5380.

Koob, George F., and Barbara J. Mason. "Existing and future drugs for the treatment of the dark side of addiction." Annual Review of Pharmacology and Toxicology, (2016), vol. 56: pp. 299-322.

Koob, George F., and Nora D. Volkow. "Neurobiology of addiction: a neurocircuitry analysis." The Lancet Psychiatry, (2016), vol. 3, No. 8: 760-773.

Kumar, Vivek, et al. "Highly selective dopamine D3 receptor (D3R) antagonists and partial agonists based on eticlopride and the D3R crystal structure: new leads for opioid dependence treatment." Journal of medicinal chemistry , (2016), vol. 59, No. 16: 7634-7650.

Ledent, Catherine, et al. "Unresponsiveness to cannabinoids and reduced addictive effects of opiates in CB1 receptor knockout mice." Science, (1999), vol. 283, No. 5400: 401-404.

Lemberg, Kim, et al. "Morphine, oxycodone, methadone and its enantiomers in different models of nociception in the rat." Anesthesia & Analgesia, (2006), vol. 102, No. 6: 1768-1774.

Leri, Francesco, and Lindsay H. Burns. "Ultra-low-dose naltrexone reduces the rewarding potency of oxycodone and relapse vulnerability in rats." Pharmacology Biochemistry and Behavior, (2005), vol. 82, No. 2: 252-262.

Li, Tao, et al. "Role of dopamine D3 receptors in basal nociception regulation and in morphine-induced tolerance and withdrawal." Brain research, (2012), 1433: 80-84.

Mizuhara, Tsukasa, et al. "Structure-activity relationship study of phenylpyrazole derivatives as a novel class of anti-HIV agents." Bioorganic & medicinal chemistry letters, (2013), vol. 23, No. 16: 4557-4561.

Newman, Amy Hauck, et al. "Dopamine D3 receptor partial agonists and antagonists as potential drug abuse therapeutic agents." Journal of medicinal chemistry, (2005), vol. 48, No. 11: 3663-3679.

Newman et al., "N-{4-[4-(2,3-Dichlorophenyl)piperazin-1-yl]butyl, Butenyl and Butynyl}arylcarboxamides as Novel Dopamine D3 Receptor Antagonists", Bioorganic & Medicinal Chemistry Letters 13: pp. 2179-2183, (2003).

Olmstead, Mary C. et al.; "Ultra-low-dose naltrexone suppresses rewarding effects of opiates and aversive effects of opiate withdrawal in rats"; Psychopharmacology, 181: 2005; p. 576-581.

Poyhia, Reino et al.; "Antinociceptive effects and central nervous system depression caused by oxycodone and morphine in rats"; Pharmacology & Toxicology; 70(2): 125-130, 1992.

Remington's Pharmaceutical Sciences, 17th ed., Mack Publishing Company, Easton, Pa., p. 1418 (1985).

Rice, Onarae V. et al.; "The acute admin of the selective dopamine D(3) receptor antagonist SB-277011A reverses conditioned place aversion produced by naloxone precipitated withdrawal from acute morphine admin in rats", Synapse 66(1): 85-87, 2012.

Spangler, Rudolph et al.; "Elevated D3 dopamine receptor mRNA in dopaminergic and dopaminoceptive regions of the rat brain in response to morphine"; Mol Brain Res 111(1-2): 74-83, 2003.

Webster, Lynn R. et al.; "Oxytrex minimizes physical dependence while providing effective analgesia: a randomized controlled trial in low back pain" J Pain 7(12): 937-946, 2006.

Wislicenus, Johannes; "Adolph Strecker's Short Textbook of Organic Chemistry" 1881, Spottiswoode: London, p. 38-39.

Written Opinion for International Application No. PCT/US2019/050165, International Filing Date Sep. 9, 2019, Date of Mailing Jan. 29, 2020, 13 pages.

Xi, Zheng-Xiong et al.; "Blockade of mesolimbic dopamine D3 receptors inhibits stress-induced reinstatement of cocaine-seeking in rats"; Psychopharmacology, 176: 2004; pp. 57-65.

Xi, Zheng-Xiong et al; "Selective dopamine D3 receptor antagonism by SB-277011A attenuates cocaine reinforcement as assessed by progressive-ratio & variable-cost-variable-payoff fixed-ratio cocaine self-admin in rats"; Eur. J Neurosci, 21: 2005 p. 3427-3438.

You Zhi-Bing et al.; "The novel dopamine D3 receptor antagonists/partial agonists CAB2-015 and BAK4-54 inhibit oxycodone-taking and oxycodone-seeking behavior in rats"; Neuropharmacology 126: 190-199, 2017.

Yu, Hailei et al.; "Effects of Exogenous Cholecystokinin Octapeptide on Acquisition of Nalozone Precipitated Withdrawal Induced Conditioned Place Aversion in Rats"; Plos One, 7:7, Jul. 2012; pp. 1-8.

Hackling et al., "Dopamine D3 Receptor Ligands with Antagonist Properties," ChemBioChem, vol. 3, 2002, pp. 946-961.

Kumar et al., "Evaluation of the D3 dopamine receptor selective antagonist PG01037 on L-dopa-dependent abnormal involuntary movements in rats," Neuropharmacology, vol. 56, 2009. pp. 944-955.

(56) References Cited

OTHER PUBLICATIONS

Leggio et al., "Dopamine D3 receptor as a new pharmacological target for the treatment of depression," European Journal of Pharmacology, vol. 719, 2013, pp. 25-33.
Nathan et al., "The effects of the dopamine D3 receptor antagonist GSK598809 on attentional bias to palatable food cues in overweight and obese subjects," International Journal of Neuropsychopharmacology, vol. 15, 2012, pp. 149-161.
Oh et al., "Dopamine D3 receptor ligand suppresses the expression of levodopa-induced dyskinesia in nonhuman primate model of parkinson's disease," Experimental Neurology 347 (2022) 113920, pp. 1-12.
Pinto et al., "Cariprazine in the treatment of Bipolar Disorder: A systematic review and meta-analysis," Bipolar Disorders, vol. 00, 2019, pp. 1-12.
Riddle et al., "Evaluation of the D3 dopamine receptor selective agonist/partial agonist PG01042 on L-dopa dependent animal involuntary movements in rats," Neuropharmacology, vol. 60, 2011, pp. 284-294.

\* cited by examiner

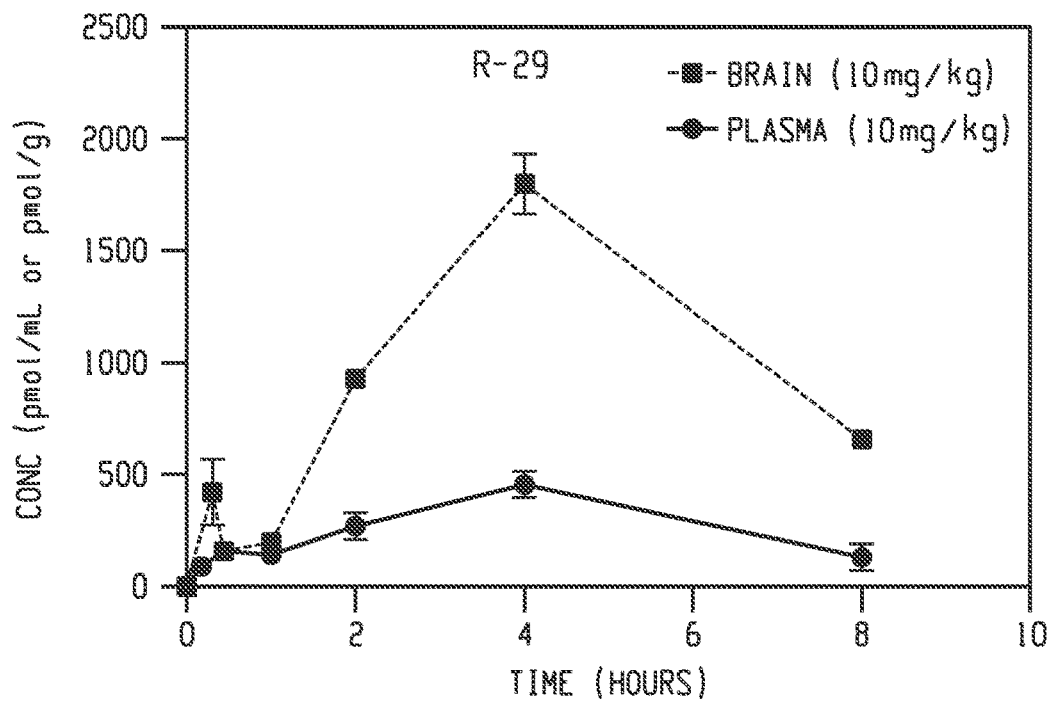
Fig. 5A1
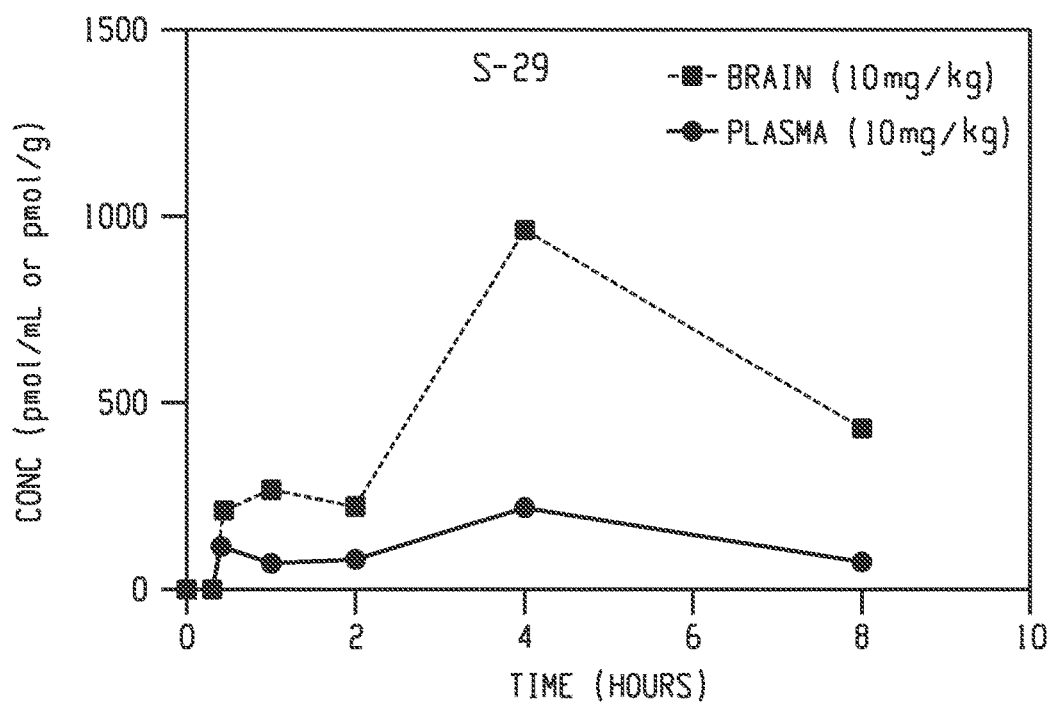
Fig. 5A2

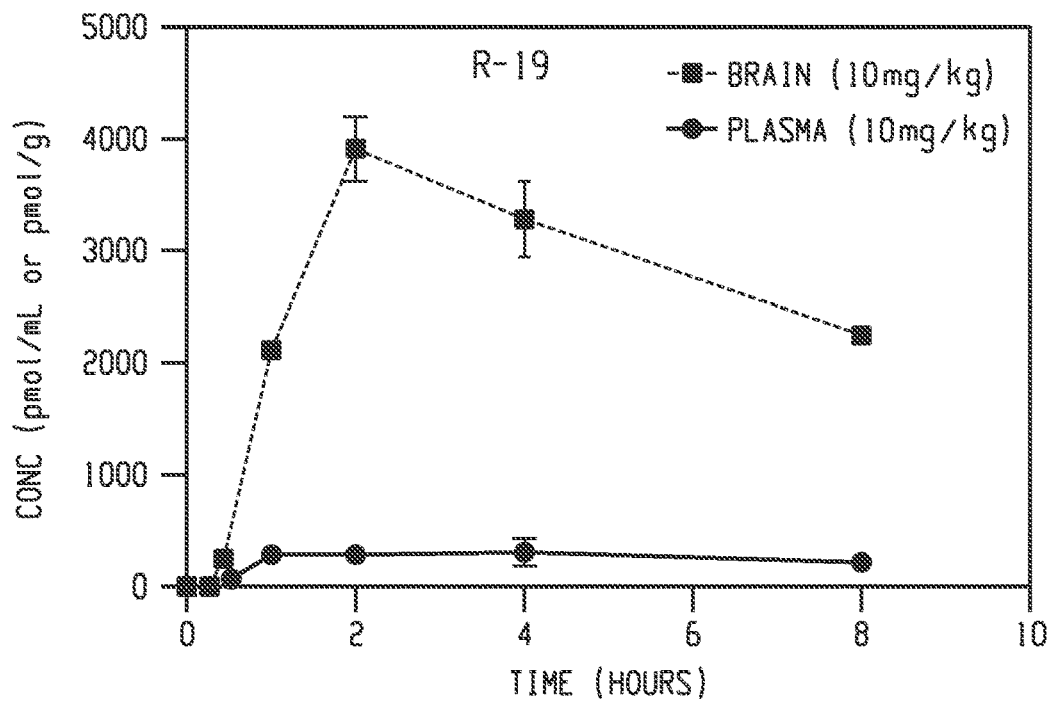
Fig. 5B1
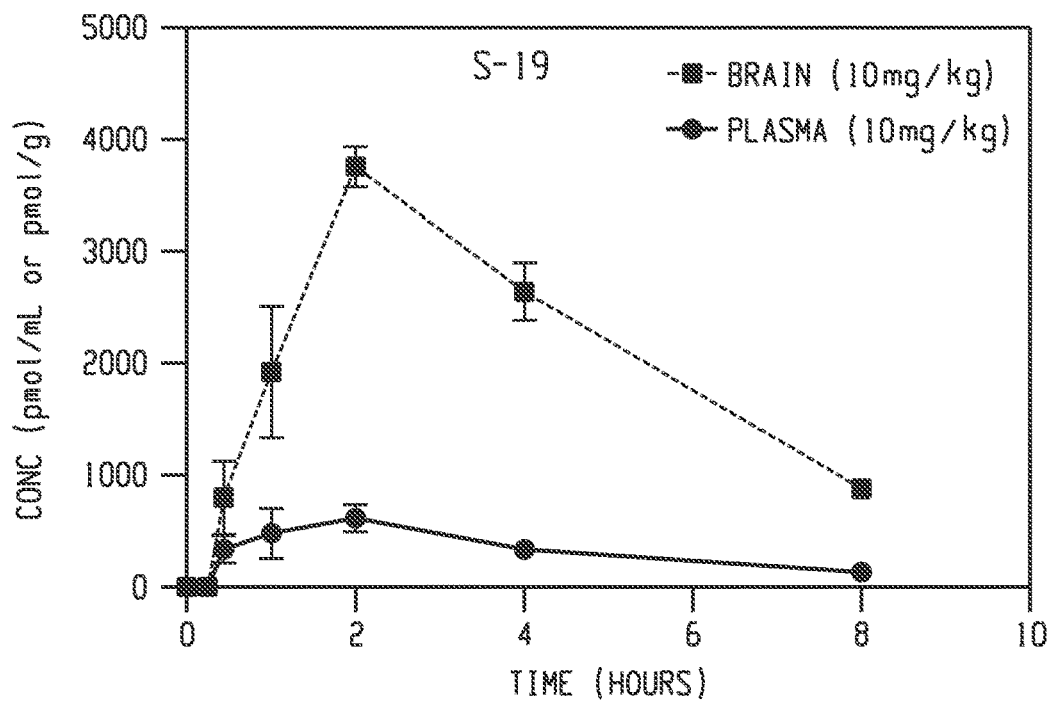
Fig. 5B2

DOPAMINE D3 RECEPTOR SELECTIVE ANTAGONISTS/PARTIAL AGONISTS AND USES THEREOF

CROSS-REFERENCE TO RELATED APPLICATIONS

This application is a Continuation application of U.S. patent application Ser. No. 17/265,150, filed 1 Feb. 2021, which is a U.S. National Stage application of International Application No. PCT/US2019/050165, filed 9 Sep. 2019, which claims the benefit of U.S. Provisional Application No. 62/729,709, filed 11 Sep. 2018, each of which is incorporated herein in its entirety for all purposes.

FIELD OF THE DISCLOSURE

The present disclosure is directed to the use of dopamine D3 receptor selective antagonist/partial agonist compounds with opioid analgesic compounds in the treatment of pain or with Medication Assisted Treatment agents to treat opioid use disorders (OUD).

BACKGROUND

Prescription opioids, such as oxycodone and morphine, are effective analgesics in clinical pain management. Nevertheless, in addition to the side effects of these drugs that include respiratory depression and constipation, one of the more serious adverse effects is the potential to develop tolerance and dependence. Indeed, the dramatic increase in prescription opioid use and abuse has led to significant increases in emergency room visits, drug-related deaths and admissions to substance-abuse treatment programs, each imposing significant impact on public health and economic welfare. It is estimated that 11.5 million Americans used prescription opioids non-medically in 2016 and 80% of the population suffering from opioid use disorders were prescription opioid abusers. This rise in prescription opioid misuse and abuse is also associated with an increased rate of transition to heroin, an illicit opioid sharing similar pharmacologic actions with prescription opioids.

Currently, Medication Assisted Treatment (MAT) with either oral methadone or various formulations of buprenorphine are the standard care for the treatment of opioid use disorders (OUD). Although significant improvement in abstinence is achieved in many patients with OUD, these medications are not always effective and have their own opioid-related side effects, which may not be well tolerated, including respiratory depression, constipation and dependence.

Dopamine is a major neurotransmitter in the central nervous system responsible for many neurological processes, including emotion, cognition, reward, motivation and fine motor control. Dopamine signaling is mediated by $D_1$-like ($D_1$ and $D_5$ receptor subtypes) and $D_2$-like ($D_2$, $D_3$ and $D_4$ receptor subtypes). Dopamine $D_3$ receptors ($D_3R$) have been implicated as potential pharmacotherapeutic targets for substance use disorders because of their restricted localization to limbic brain regions, effectiveness in animal models of drug abuse and upregulation in the brains of cocaine addicts. Blockade of D3R with selective D3R antagonists has been shown to significantly inhibit psychostimulant self-administration, conditioned place preference (CPP) to abused drugs, and reinstatement of drug-seeking behavior triggered by addictive drugs, stress or drug associated cues. D3R blockade also inhibits locomotor sensitization and the enhanced brain stimulation reward induced by drugs of abuse.

Chronic use of opioids can lead to dependence, which is behaviorally driven by disturbances in affective function involving dopaminergic neurocircuitry that promote a compensatory and compulsive drive to enhance hedonic tone and decrease negative affect.

Therefore, there is a need in the art for safer methods of pain management using dopamine D3 receptor selective antagonists/partial agonists in concert with opioid analgesics to balance hedonic tone, reduce dose escalation and prevent the development of opioid use disorders.

Further, there remains a need to enhance the effectiveness of current MAT for the treatment of OUD.

SUMMARY

In an embodiment, a method of treating an opioid use disorder, mitigating the development of opioid addiction, reducing the severity of opioid withdrawal symptoms, or reducing or preventing opioid relapse, comprises providing to a patient in need thereof a therapeutically effective amount of a Medication Assisted Treatment agent and a therapeutically effective amount of a selective dopamine D3 receptor antagonist/partial agonist.

In another embodiment, a method of treating an opioid use disorder, mitigating the development of opioid addiction, reducing the severity of opioid withdrawal symptoms, or reducing or preventing opioid relapse, comprises providing to a patient in need thereof a therapeutically effective amount of a Medication Assisted Treatment agent or a pharmaceutically acceptable salt thereof and a therapeutically effective amount of a compound of Formula (I) or (II), a stereoisomer thereof, or a pharmaceutically acceptable salt thereof

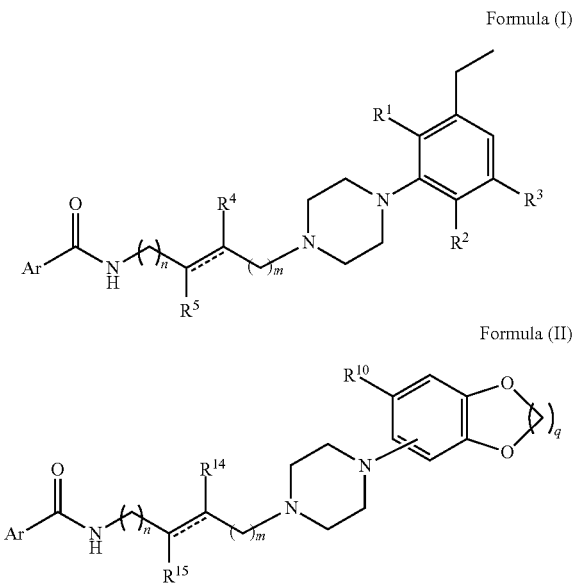

wherein

Ar is a heteroaryl which may be optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, mono- or di-$C_1$-$C_3$alkylamino, or halogen, or Ar is a 3,4-methylenedioxy-phenyl group;

n is 0, 1, 2, 3, or 4, specifically n is 1 or 2;
m is 0, 1, 2, 3, or 4, specifically m is 1 or 2;
q is 1 or 2;
$R^1$ is H or halogen;
$R^2$ is H, $C_1$-$C_3$alkoxy, or halogen;
$R^3$ is H, halogen or $C_1$-$C_3$alkoxy;
$R^4$ is H, —OH, or halogen;
$R^5$ is H, —OH, or halogen;
$R^{10}$ is $C_1$-$C_6$alkyl;
$R^{14}$ is H, —OH, or halogen;
$R^{15}$ is H, —OH, or halogen; and
--- is a single bond, a double bond, a $C_3$-$C_6$ cycloalkyl, or a $C_3$-$C_6$ cycloalkenyl,
with the provisos a) and b) for Formula (I)
a) when $R^1$ is H then at least one of $R^2$ and $R^3$ is not H; and
b) when one or both of $R^2$ and $R^3$ is H then $R^1$ is not H.

In an embodiment, a method for treating pain, comprises providing to a patient in need thereof a therapeutically effective amount of an opioid analgesic and a therapeutically effective amount of a selective dopamine D3 receptor antagonist/partial agonist.

In an embodiment, a method for treating pain, comprises providing to a patient in need thereof a therapeutically effective amount of an opioid analgesic or a pharmaceutically acceptable salt thereof and a therapeutically effective amount of a compound of Formula (I) or (II), a stereoisomer thereof, a radioisotope thereof, or a pharmaceutically acceptable salt thereof

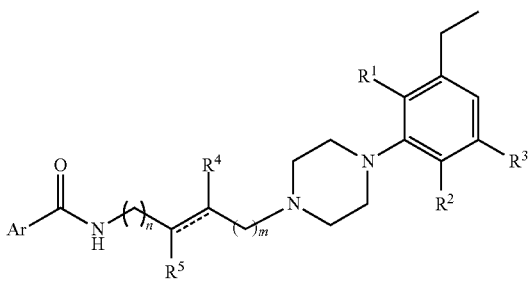

Formula (I)

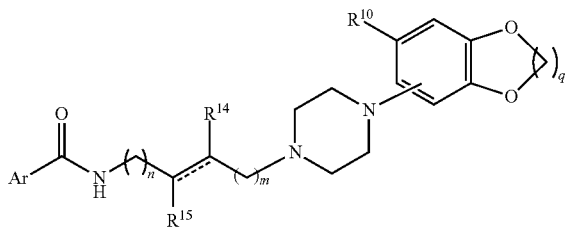

Formula (II)

wherein

Ar is a heteroaryl which may be optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, mono- or di-$C_1$-$C_3$alkylamino, or halogen, or Ar is a 3,4-methylenedioxy-phenyl group; n is 0, 1, 2, 3, or 4; m is 0, 1, 2, 3, or 4; q is 1 or 2; $R^1$ is H or halogen; $R^2$ is H, $C_1$-$C_3$alkoxy, or halogen; $R^3$ is H, halogen or $C_1$-$C_3$alkoxy; $R^4$ is H, —OH, or halogen; $R^5$ is H, —OH, or halogen; $R^{10}$ is $C_1$-$C_6$alkyl; $R^{14}$ is H, —OH, or halogen; $R^{15}$ is H, —OH, or halogen; and --- is a single bond, a double bond, a $C_3$-$C_6$ cycloalkyl, or a $C_3$-$C_6$ cycloalkenyl, with the provisos a) and b) for Formula (I): a) when $R^1$ is H then at least one of $R^2$ and $R^3$ is not H; and b) when one or both of $R^2$ and $R^3$ is H then $R^1$ is not H.

In another embodiment, a pharmaceutical composition comprises a combination of a therapeutically effective amount of an opioid analgesic or a pharmaceutically acceptable salt thereof, a therapeutically effective amount of Medication Assisted Treatment agent, or a combination thereof; and a therapeutically effective amount of a compound of Formula (I) or (II), a stereoisomer thereof, or a pharmaceutically acceptable salt thereof wherein Ar is a heteroaryl which may be optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, mono- or di-$C_1$-$C_3$alkylamino, or halogen, or Ar is a 3,4-methylenedioxy-phenyl group;

n is 0, 1, 2, 3, or 4, specifically n is 1 or 2;
m is 0, 1, 2, 3, or 4, specifically m is 1 or 2;
q is 1 or 2;
$R^1$ is H or halogen;
$R^2$ is H, $C_1$-$C_3$alkoxy, or halogen;
$R^3$ is H, halogen or $C_1$-$C_3$alkoxy;
$R^4$ is H, —OH, or halogen;
$R^5$ is H, —OH, or halogen;
$R^{10}$ is $C_1$-$C_6$alkyl;
$R^{14}$ is H, —OH, or halogen;
$R^{15}$ is H, —OH, or halogen; and
--- is a single bond, a double bond, a $C_3$-$C_6$ cycloalkyl, or a $C_3$-$C_6$ cycloalkenyl,
with the provisos a) and b) for Formula (I)
a) when $R^1$ is H then at least one of $R^2$ and $R^3$ is not H; and
b) when one or both of $R^2$ and $R^3$ is H then $R^1$ is not H; and optionally further comprises a pharmaceutically acceptable carrier. Pharmaceutical kits are also disclosed.

BRIEF DESCRIPTION OF DRAWINGS

FIG. 3A: Compound (±)-29 pretreatment produced a leftward shift in the dose-response curve of oxycodone in hot-plate test; data represent mean (±S.E.M) for n=8-9 in each group. FIG. 3B: Time courses of 2.0 mg/kg oxycodone-induced analgesia as assessed by hot-plate test in the absence or presence of compound (±)-29. Oxycodone dose-dependently increased MPE % and the highest dose of compound (±)-29 pretreatment significantly potentiated oxycodone's effect at the 1 and 2 mg/kg doses. Data represent mean (±SEM) for n=8-9 in each group. **$P<0.01$ versus corresponding values in vehicle pretreated group.

FIGS. 5A1, 5A2, 5B1, and 5B2: Pharmacokinetic studies on R-29 (FIG. 5A1) and S-29 (FIG. 5A2) and R-19 (FIG. 5B1) and S-19 (FIG. 5B2) in Long Evans rats after oral administration of 10 mg/kg demonstrating that all four enantiomers are highly brain penetrable.

DETAILED DESCRIPTION

Figure 1A:
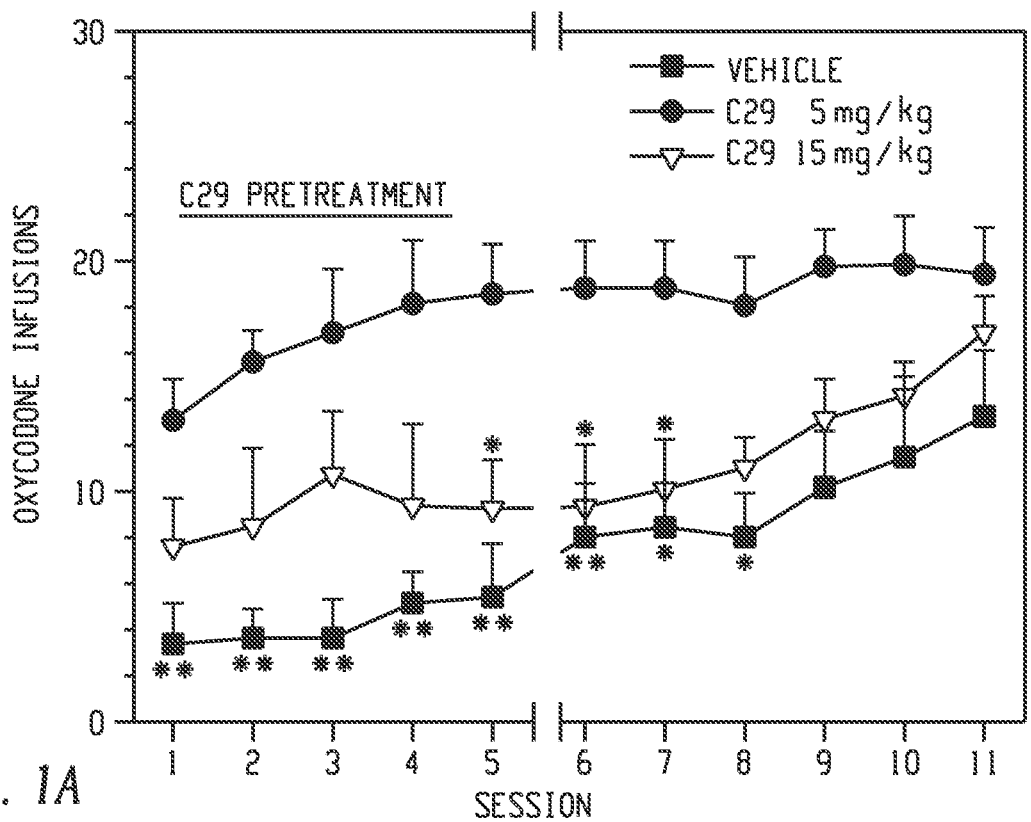
FIG. 1A, FIG. 1B, FIG. 1C, FIG. 1D, FIG. 1E, and FIG. 1F show effects of compound (±)-29 on oxycodone-taking and oxycodone-seeking behavior in rats; pretreatment with compound (±)-29 (5-15 mg/kg, i.p. for 5 consecutive days) dose-dependently inhibited the acquisition of oxycodone self-administration as assessed by oxycodone infusions (FIG. 1A) and active lever presses (FIG. 1B) (n=8); pretreatments with compound (±)-29 (5-25 mg/kg, i.p.) dose-dependently reduced oxycodone self-administration during the maintenance of self-administration (FIG. 1C) and oxycodone seeking when oxycodone was replaced by saline during self-administration (FIG. 1D) (n=6-7); compound (±)-29 dose-dependently lowered the PR break-point for oxycodone self-administration (FIG. 1E) (n=7), but had no effect on oral sucrose self-administration (FIG. 1F) (n=7). * $P<0.05$, $P<0.01$, *$P<0.001$, compared to vehicle group.
Figure 1B:
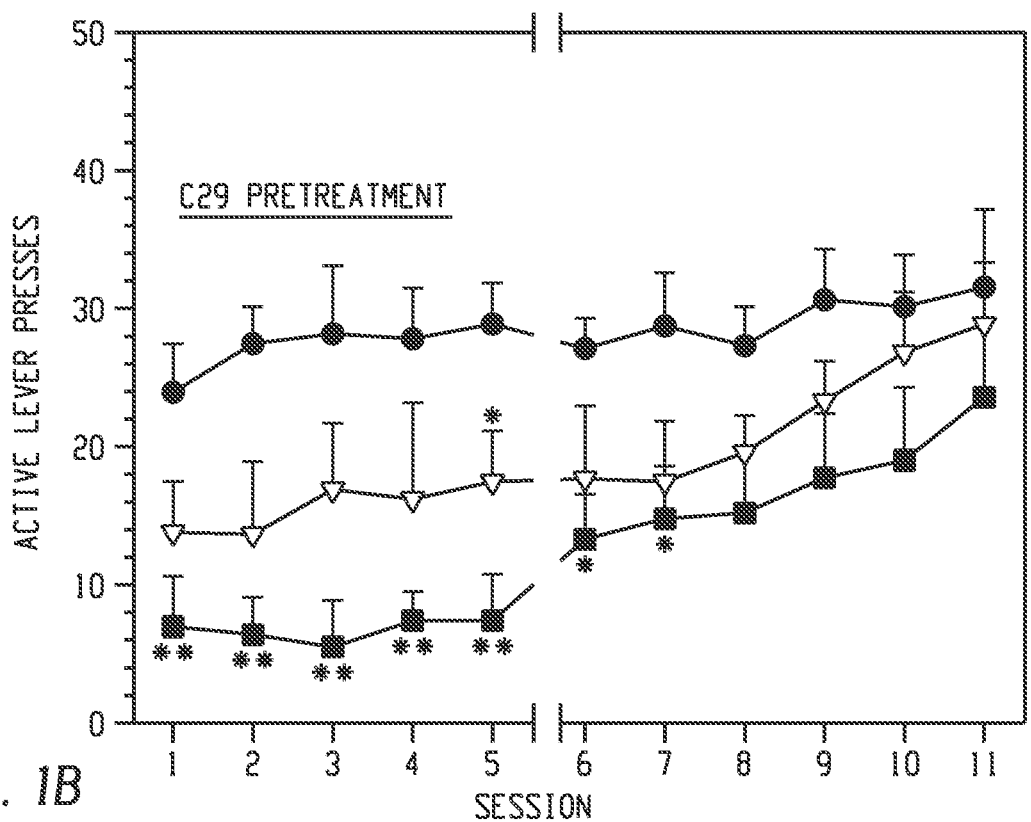

Disclosed are methods of treating opioid use disorders, mitigating the development of opioid addiction, reducing the severity of opioid withdrawal symptoms, or reducing or preventing opioid relapse comprises providing a Medication Assisted Treatment agent or a pharmaceutically acceptable salt thereof and a therapeutically effective amount of a selective dopamine D3 receptor antagonist/partial agonist or a pharmaceutically acceptable salt thereof to a patient in need of such treatment. The effectiveness of current Medication Assisted Treatment for the treatment of OUD may be enhanced with the addition of the dopamine D3 antagonist/partial agonist. Suitable selective dopamine D3 receptor antagonist/partial agonist compounds include those described herein according to Formula (I) and (II).

Also disclosed is a method of treating pain by providing a therapeutically effective amount of an opioid analgesic or a pharmaceutically acceptable salt thereof and a therapeutically effective amount of a selective dopamine D3 receptor antagonist/partial agonist or a pharmaceutically acceptable salt thereof to a patient in need of such treatment. The therapeutically effective amount of opioid analgesic may be lower than conventional amounts when used in the presence of the dopamine D3 antagonist/partial agonist as the D3 antagonist/partial agonist will potentiate the analgesic effect of the opioid analgesic and will prevent dose escalation for pain relief. Suitable selective dopamine D3 receptor antagonist/partial agonist compounds include those described herein according to Formula (I) and (II). The opioid analgesic provides the analgesic effect while the selective dopamine D3 receptor antagonist/partial agonist compound mitigates the development of opioid addiction by eliminating the need for dose escalation, reduces the severity of withdrawal symptoms, and prevents relapse of opioid misuse, if dependence does develop. In an additional embodiment, the selective dopamine D3 receptor antagonist/partial agonist compound of Formula (I) or (II) potentiates the analgesic effect of subtherapeutic doses of the opioid analgesic, oxycodone. This effect thereby provides a clinical advantage of using lower doses of the opioid for adequate pain management. Using lower doses and preventing dose escalation will significant decrease the chances of developing opioid dependence.

It has been found that pretreatment with a selective dopamine D3 receptor antagonist/partial agonist compound according to Formula (I) or (II) dose-dependently inhibits the acquisition and maintenance of oxycodone self-administration in animal models. The compound further lowers the break-point for oxycodone self-administration under a progressive-ratio (PR) schedule of reinforcement, and inhibits oxycodone extinction response and reinstatement of oxycodone-seeking behavior. Pretreatment with the compound shows a potentiation of a subthreshold dose of oxycodone's antinociceptive effects and these analgesic data have been replicated in rhesus monkeys.

As used herein, the term "Medication Assisted Treatment agent" means an active agent used in the treatment of opioid addiction, including opioid agonists and opioid partial agonists. Examples of suitable Medication Assisted Treatment agents included methadone, buprenorphine, naloxone, naltrexone, levo-alpha acetyl methadol, or a combination thereof.

As used herein, the term "opioid" means an active agent that combines with opioid receptors to produce a physiological effect specifically analgesia, and include opioid receptor agonists, partial agonists, agonist-antagonists, and antagonists. Opioid agonists, partial agonists, and mixed agonist-antagonists have been used in the treatment of pain. Exemplary opioid analgesics that can be used in combination with the dopamine D3 receptor selective antagonists/partial agonists compounds according to Formula (I) or (II) include bremazocine, buprenorphine, butorphanol, carfentanyl, codeine, cyclazocine, dezocine, diamorphine, dihydrocodeine, dihydromorphine, dihydromorphinone (aka hydromorphone), enadoline, eseroline, ethylmorphine, etonitazine, etorphine, fentanyl, hydrocodone, levophenacylmorphan, levorphanol, meperidine/pethidine, methadone, morphine, nalbuphine, nicomorphine, oxycodone, oxymorphone, pentazocine, phenazocine, picenadol, tramadol, tapentadol, or a combination thereof. In an embodiment, the opioid analgesic is oxycodone.

The selective dopamine D3 receptor antagonist/partial agonist compound can be administered to the patient concurrently with the opioid analgesic administration, prior to the opioid analgesic, after treatment with the opioid analgesic, or a combination thereof. In an embodiment, the dopamine D3 receptor antagonist/partial agonist compound is administered to the patient prior to administration of the opioid analgesic as a pretreatment, and then subsequently administered concurrently with the opioid analgesic to provide effective pain management as well as to reduce or prevent the development of opioid dependence. Further dosing regimens are described herein.

The selective dopamine D3 receptor antagonist/partial agonist compound can be administered to the patient concurrently with a Medication Assisted Treatment agent alone. The combination can be administered to the patient with the opioid analgesic administration, prior to the opioid analgesic, after treatment with the opioid analgesic, or a combination thereof. In an embodiment, the dopamine D3 receptor antagonist/partial agonist compound and Medication Assisted Treatment agent are administered to the patient prior to administration of the opioid analgesic as a pretreatment, and then subsequently administered concurrently with the opioid analgesic to provide effective pain management as well as to reduce or prevent the development of opioid dependence. Further dosing regimens are described herein.

The term "patient", as used herein, is a human in need of medical treatment. Medical treatment can include treatment of an existing condition, such as a disease or disorder, prophylactic or preventative treatment, or diagnostic treatment.

The term "providing", as used herein, means giving, administering, selling, distributing, transferring (for profit or not), manufacturing, compounding, or dispensing.

The term "concurrently providing a compound of Formula (I) or (II) with a Medication Assisted Treatment agent", as used herein, means the compound of Formula (I) or (II) and the Medication Assisted Treatment agent are provided simultaneously in a single dosage form, provided concomitantly in separate dosage forms, or provided in separate dosage forms for administration separated by some amount of time that is within the time in which both the compound of Formula (I) or (II) and the Medication Assisted Treatment agent are within the blood stream of a patient. The compound of Formula (I) or (II) and the Medication Assisted Treatment agent need not be prescribed for a patient by the Medication Assisted Treatment agent can occur together or individually via any appropriate route, for example, oral tablets, oral capsules, oral liquids, inhalation, injection, suppositories, topical contact, or a combination thereof (e.g. the compound of Formula (I) or (II) is administered orally and the Medication Assisted Treatment agent is administered parenterally, or the compound of Formula (I) or (II) is administered via a patch and the Medication Assisted Treatment agent is administered subcutaneously).

The term "concurrently providing a compound of Formula (I) or (II) with an opioid analgesic", as used herein, means the compound of Formula (I) or (II) and the opioid analgesic are provided simultaneously in a single dosage form, provided concomitantly in separate dosage forms, or provided in separate dosage forms for administration separated by some amount of time that is within the time in which both the compound of Formula (I) or (II) and the opioid analgesic are within the blood stream of a patient. The compound of Formula (I) or (II) and the opioid analgesic need not be prescribed for a patient by the same medical care worker. Administration of the compound of Formula (I) or (II) or the opioid analgesic can occur together or individually via any appropriate route, for example, oral tablets, oral capsules, oral liquids, inhalation, injection, suppositories, topical contact, or a combination thereof (e.g. the compound of Formula (I) or (II) is administered orally and the opioid analgesic is administered parenterally, or the compound of Formula (I) or (II) is administered via a patch and the opioid analgesic is administered orally).

The term "treatment", as used herein, includes providing a compound of Formula (I), either as the only active agent or together with at least one additional active agent such as an opioid analgesic sufficient to prevent or inhibit or relieve pain, or a Medication Assisted Treatment agent; provide analgesia; to mitigate the development of opioid addiction, to reduce the severity of opioid withdrawal symptoms, to reduce or prevent opioid relapse, and the like. "Treating" and "treatment" also means providing a therapeutically effective amount of a compound of Formula (I) or (II), as the only active agent or together with at least one additional active agent to a patient receiving opioid analgesic therapy.

The term "therapeutically effective amount" as used herein, means an amount effective, when administered to a patient, to provide a therapeutic benefit, such as an amelioration of symptoms, e.g., to treat a patient suffering from pain, to provide analgesia, to mitigate the development of opioid addiction, to reduce the severity of opioid withdrawal symptoms, to reduce or prevent opioid relapse, and the like.

As used herein the pain to be treated by the methods is not particularly limiting and can include chronic pain, acute pain, breakthrough pain, post-operative pain, perioperative pain, mild pain, moderate pain, severe pain, bone and joint pain, soft tissue pain, nerve pain, pain due to a disease or disorder, pain due to trauma, and the like, and a combination thereof.

In addition to methods of treating pain comprising providing an opioid analgesic and a selective dopamine D3 receptor antagonist/partial agonist compound to a patient in need thereof, other embodiments include a method for reducing or preventing opioid addiction in combination with a Medication Assisted Treatment agent, reducing the severity of opioid withdrawal symptoms, and/or reducing or preventing opioid relapse are provided.

The dopamine D3 receptor selective antagonists/partial agonists compounds according to Formula (I) unexpectedly have both high affinity for the D3 receptor and excellent metabolic stability not achieved by prior dopamine D3 receptor selective antagonists/partial agonists. Many of the compounds of Formula (I) exhibit high selectivity over the homologous D2 receptor family members e.g. D2 and D4 receptors. The compounds of Formula (I) disclosed herein exhibit improved pharmacological properties, bioavailability, and metabolic stability in vivo over prior 4-phenylpiperazine derivative D3 receptor ligands. Due to their high potency and D3 receptor selectivity, lower doses of the compounds of Formula (I) may be effective and thus side effect potential is limited.

A compound of Formula (I) or a pharmaceutically acceptable salt thereof, a radioisotope thereof, or a stereoisomer thereof:

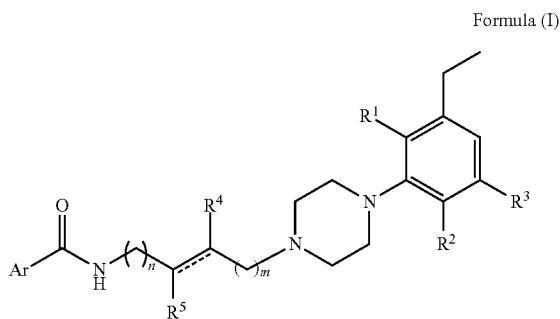

Formula (I)

wherein Ar is a heteroaryl which may be optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, mono- or di-$C_1$-$C_3$alkylamino, or halogen, or Ar is a 3,4-methylenedioxy-phenyl group; specifically Ar is benzofuranyl, benzothienyl, imidazolyl, imidazo[1,2-a]pyridinyl, imidazo[2,1-b]thiazolyl, or indolyl; and more specifically Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl;

n is 0, 1, 2, 3, or 4, specifically n is 1 or 2;

m is 0, 1, 2, 3, or 4, specifically m is 1 or 2;

$R^1$ is H or halogen (Cl, F, Br, I), specifically H or Cl;

$R^2$ is H, $C_1$-$C_3$alkoxy, or halogen (Cl, F, Br, I), specifically H or —OMe;

$R^3$ is H, halogen (Cl, F, Br, I), or $C_1$-$C_3$alkoxy, specifically H or Cl;

$R^4$ is H, —OH, or halogen, specifically H, —OH or —F;

$R^5$ is H, —OH, or halogen, specifically H, —OH or —F; and

⚌ is a single bond, a double bond (e.g. trans or cis double bond, specifically trans), a cycloalkyl, specifically a $C_3$-$C_6$ cycloalkyl such as a cyclopropyl or cyclohexyl (e.g. trans or cis, specifically trans), or a cycloalkenyl, specifically a $C_3$-$C_6$ cycloalkenyl, with the provisos a) and b):

a) when $R^1$ is H then at least one of $R^2$ and $R^3$ is not H, specifically $R^2$ is $C_1$-$C_3$alkoxy (e.g. —OMe) and $R^3$ is halogen (e.g. Cl); and b) when one or both of $R^2$ and $R^3$ is H then $R^1$ is not H, specifically $R^1$ is halogen (e.g. Cl).

In an embodiment, a compound of Formula (I) or a pharmaceutically acceptable salt thereof wherein $R^1$ is H, $R^2$ is —OMe, and $R^3$ is Cl.

In an embodiment, a compound of Formula (I) or a pharmaceutically acceptable salt thereof wherein $R^1$ is Cl, $R^2$ is H, and $R^3$ is H.

In an embodiment, a compound of Formula (I) or a pharmaceutically acceptable salt thereof wherein $R^1$ is H, $R^2$ is —OMe, $R^3$ is Cl, and Ar is benzofuranyl, benzothienyl, imidazolyl, imidazo[1,2-a]pyridinyl, imidazo[2,1-b]thiazolyl, or indolyl, where Ar is further optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, or halogen.

In an embodiment, a compound of Formula (I) or a pharmaceutically acceptable salt thereof wherein $R^1$ is Cl, $R^2$ is H, $R^3$ is H, and Ar is benzofuranyl, benzothienyl, imidazolyl, imidazo[1,2-a]pyridinyl, imidazo[2,1-b]thiazolyl, or indolyl, where Ar is further optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, or halogen.

In an embodiment, a compound of Formula (I) or a pharmaceutically acceptable salt thereof wherein $R^1$ is H, $R^2$ is —OMe, $R^3$ is Cl, and Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl. Further within this embodiment, m is 1 and n is 1.

In an embodiment, a compound of Formula (I) or a pharmaceutically acceptable salt thereof wherein $R^1$ is Cl, $R^2$ is H, $R^3$ is H, and Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl. Further within this embodiment, m is 1 and n is 1.

In an embodiment, a compound of Formula (I) or a pharmaceutically acceptable salt thereof wherein $R^1$ is H, $R^2$ is —OMe, $R^3$ is Cl, and Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl. Further within this embodiment one of $R^4$ and $R^5$ is H and the other is —OH or —F.

In an embodiment, a compound of Formula (I) or a pharmaceutically acceptable salt thereof wherein $R^1$ is Cl, $R^2$ is H, $R^3$ is H, and Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl. Further within this embodiment one of $R^4$ and $R^5$ is H and the other is —OH or —F.

In an embodiment, a compound of Formula (I) or a pharmaceutically acceptable salt thereof wherein $R^1$ is H; $R^2$ is —OMe; $R^3$ is Cl; Ar is benzofuranyl or indolyl; n is 1 or 2; m is 1 or 2; $R^4$ is H, —OH, or halogen, specifically H, —OH, or F; $R^5$ is H, —OH, or halogen, specifically H, —OH or F; and ⚌ is a single bond, a double bond (e.g. trans or cis double bond, specifically trans), a $C_3$-$C_6$ cycloalkyl such as a cyclopropyl or cyclohexyl (e.g. trans or cis, specifically trans), or a $C_3$-$C_6$ cycloalkenyl.

In an embodiment, a compound of Formula (I) or a pharmaceutically acceptable salt thereof wherein $R^1$ is Cl; $R^2$ is H; $R^3$ is H; Ar is benzofuranyl or indolyl; n is 1 or 2; m is 1 or 2; $R^4$ is H, —OH, or halogen, specifically H, —OH, or F; $R^5$ is H, OH, or halogen, specifically H, —OH, or F; and ⚌ is a single bond, a double bond (e.g. trans or cis double bond, specifically trans), a $C_3$-$C_6$ cycloalkyl such as a cyclopropyl or cyclohexyl (e.g. trans or cis, specifically trans), or a $C_3$-$C_6$ cycloalkenyl.

Also included in this disclosure are compounds of Formula (I) having specific structures as set out in Tables 1A and 1B herein and set out in the table below.

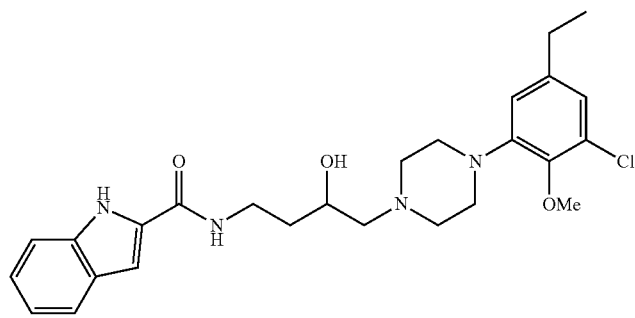
N-(4-(4-(3-chloro-5-ethyl-2-methoxyphenyl)piperazin-1-yl)-3-hydroxybutyl)-1H-indole-2-carboxamide ((±)-29)
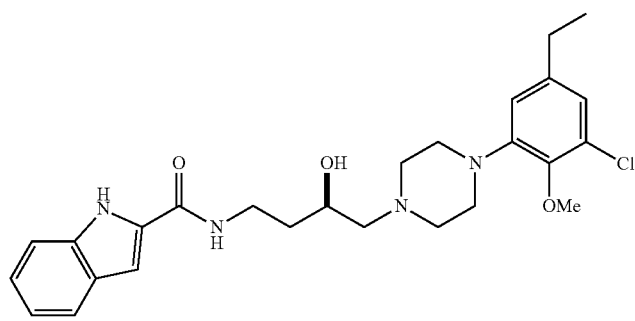 [SMILES: CCc1cc(Cl)c(OC)c(N2CCN(C[C@H](O)CCNC(=O)c3cc4ccccc4[nH]3)CC2)c1]
(R)-N-(4-(4-(3-chloro-5-ethyl-2-methoxyphenyl)piperazin-1-yl)-3-hydroxybutyl)-1H-indole-2-carboxamide ((R)-29)
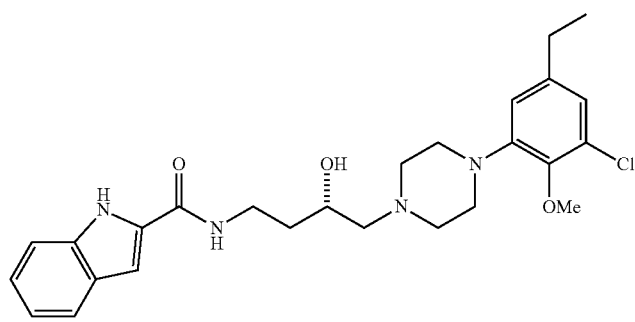 [SMILES: CCc1cc(Cl)c(OC)c(N2CCN(C[C@@H](O)CCNC(=O)c3cc4ccccc4[nH]3)CC2)c1]
(S)-N-(4-(4-(3-chloro-5-ethyl-2-methoxyphenyl)piperazin-1-yl)-3-hydroxybutyl)-1H-indole-2-carboxamide ((S)-29)
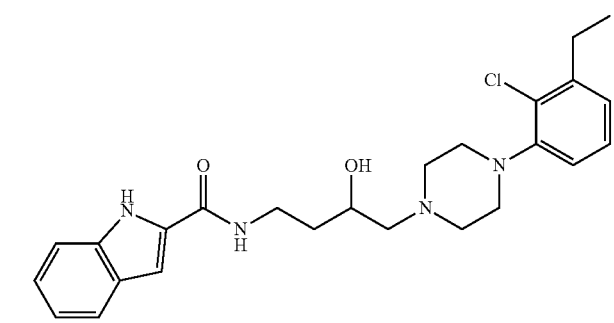 [SMILES: CCc1cccc(N2CCN(CC(O)CCNC(=O)c3cc4ccccc4[nH]3)CC2)c1Cl]
N-(4-(4-(2-chloro-3-ethylphenyl)piperazin-1-yl)-3-hydroxybutyl)-1H-indole-2-carboxamide ((±)-19)

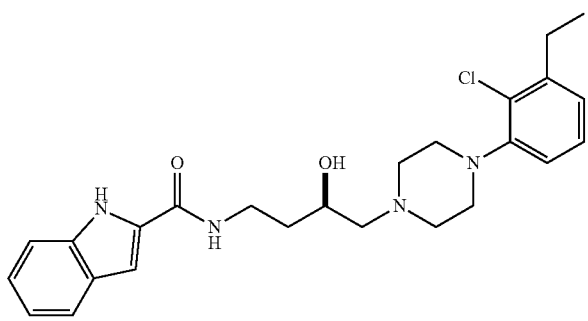 [SMILES: CCc1cccc(N2CCN(C[C@H](O)CCNC(=O)c3cc4ccccc4[nH]3)CC2)c1Cl]

(R)-N-(4-(4-(2-chloro-3-ethylphenyl)piperazin-1-yl)-3-hydroxybutyl)-1H-indole-2-carboxamide ((R-19)

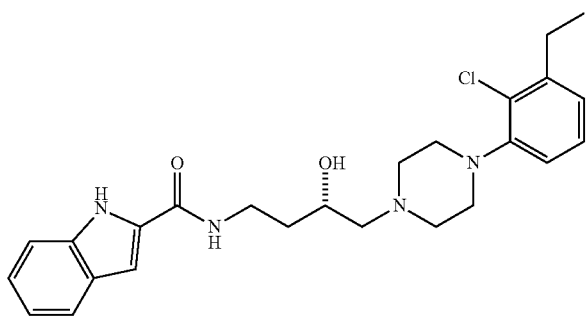 [SMILES: CCc1cccc(N2CCN(C[C@@H](O)CCNC(=O)c3cc4ccccc4[nH]3)CC2)c1Cl]

(S)-N-(4-(4-(2-chloro-3-ethylphenyl)piperazin-1-yl)-3-hydroxybutyl)-1H-indole-2-carboxamide ((S)-19)
N-(4-(4-(3-chloro-5-ethyl-2-methoxyphenyl)piperazin-1-yl)-3-fluorobutyl)-1H-indole-2-carboxamide ((±)-C4a)

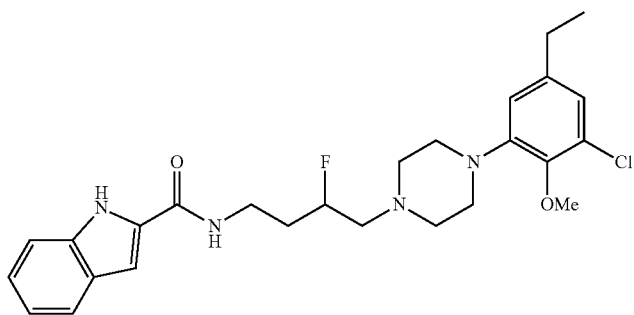 [SMILES: CCc1cc(Cl)c(OC)c(N2CCN(CC(F)CCNC(=O)c3cc4ccccc4[nH]3)CC2)c1]

(R)-N-(4-(4-(3-chloro-5-ethyl-2-methoxyphenyl)piperazin-1-yl)-3-fluorobutyl)-1H-indole-2-carboxamide ((R)-C4a)

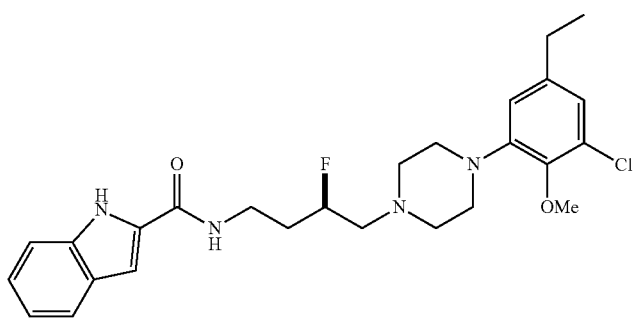 [SMILES: CCc1cc(Cl)c(OC)c(N2CCN(C[C@H](F)CCNC(=O)c3cc4ccccc4[nH]3)CC2)c1]

(S)-N-(4-(4-(3-chloro-5-ethyl-2-methoxyphenyl)piperazin-1-yl)-3-fluorobutyl)-1H-indole-2-carboxamidec((S)-C4a)

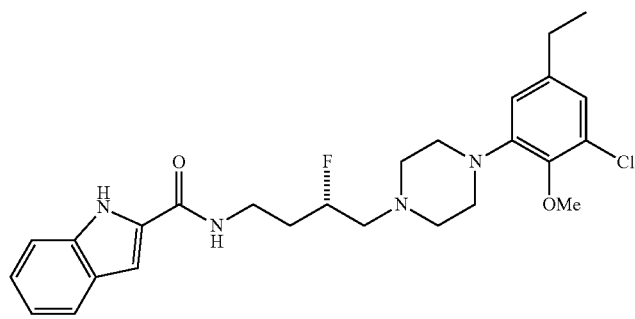 [SMILES: CCc1cc(Cl)c(OC)c(N2CCN(C[C@@H](F)CCNC(=O)c3cc4ccccc4[nH]3)CC2)c1]
N-(4-(4-(3-chloro-5-ethyl-2-methoxyphenyl)piperazin-1-yl)-3-
fluorobutyl)benzofuran-2-carboxamide ((±)-C4b)
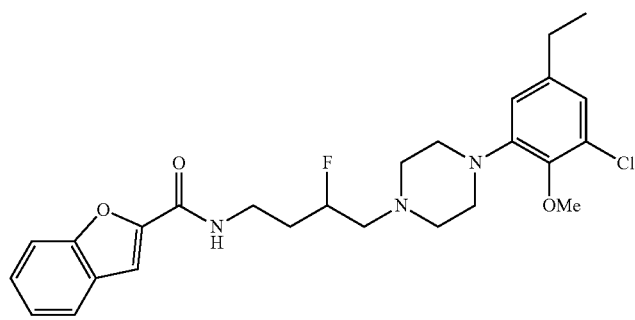 [SMILES: CCc1cc(Cl)c(OC)c(N2CCN(CC(F)CCNC(=O)c3cc4ccccc4o3)CC2)c1]
(R)-N-(4-(4-(3-chloro-5-ethyl-2-methoxyphenyl)piperazin-1-
yl)-3-fluorobutyl)benzofuran-2-carboxamide ((R)-C4b)
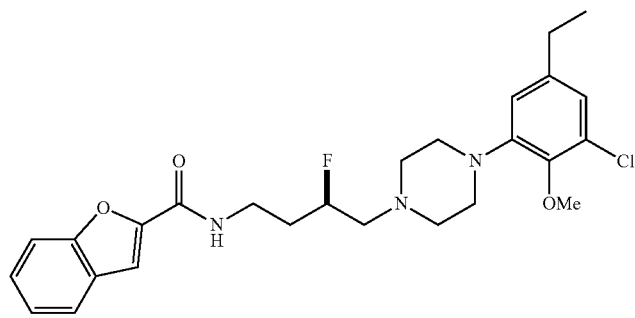 [SMILES: CCc1cc(Cl)c(OC)c(N2CCN(C[C@H](F)CCNC(=O)c3cc4ccccc4o3)CC2)c1]
(S)-N-(4-(4-(3-chloro-5-ethyl-2-methoxyphenyl)piperazin-1-
yl)-3-fluorobutyl)benzofuran-2-carboxamide ((S)-C4b)
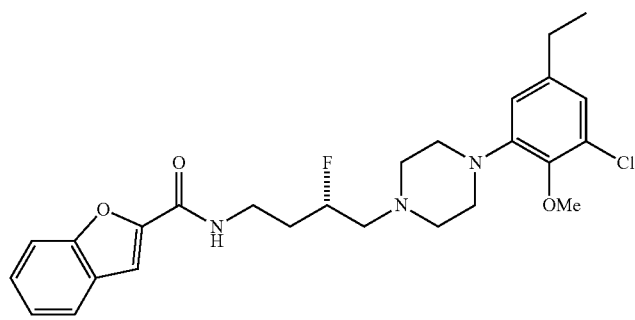 [SMILES: CCc1cc(Cl)c(OC)c(N2CCN(C[C@@H](F)CCNC(=O)c3cc4ccccc4o3)CC2)c1]
N-(4-(4-(2-chloro-3-ethylphenyl)piperazin-1-yl)-3-
fluorobutyl)-1H-indole-2-carboxamide ((±)-C5a)

-continued
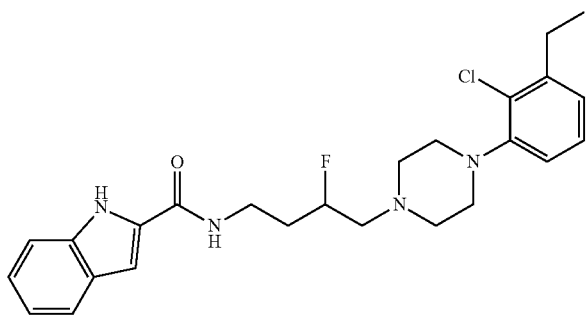 [SMILES: CCc1cccc(N2CCN(CC(F)CCNC(=O)c3cc4ccccc4[nH]3)CC2)c1Cl]
(R)-N-(4-(4-(2-chloro-3-ethylphenyl)piperazin-1-yl)-3-
fluorobutyl)-1H-indole-2-carboxamide ((R)-C5a)
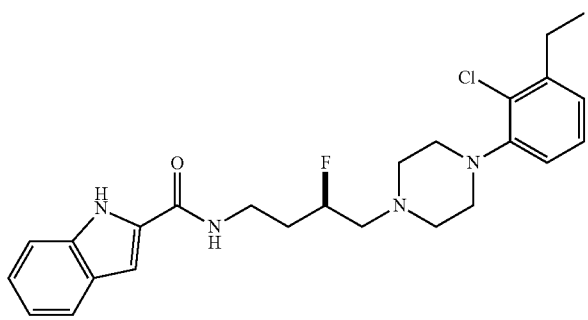 [SMILES: CCc1cccc(N2CCN(C[C@H](F)CCNC(=O)c3cc4ccccc4[nH]3)CC2)c1Cl]
(S)-N-(4-(4-(2-chloro-3-ethylphenyl)piperazin-1-yl)-3-
fluorobutyl)-1H-indole-2-carboxamide ((S)-C5a)
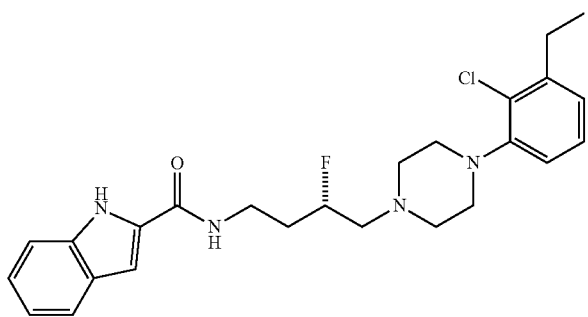 [SMILES: CCc1cccc(N2CCN(C[C@@H](F)CCNC(=O)c3cc4ccccc4[nH]3)CC2)c1Cl]
N-(4-(4-(2-chloro-3-ethylphenyl)piperazin-1-yl)-3-
fluorobutyl)benzofuran-2-carboxamide ((±)-C5b)
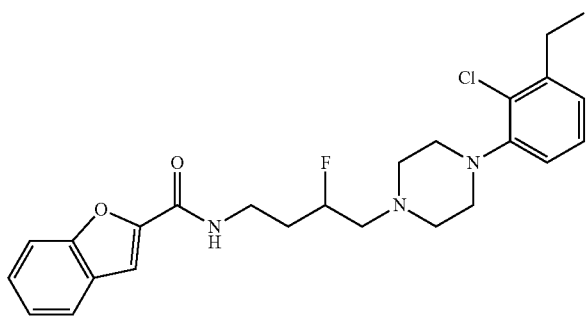 [SMILES: CCc1cccc(N2CCN(CC(F)CCNC(=O)c3cc4ccccc4o3)CC2)c1Cl]
(R)-N-(4-(4-(2-chloro-3-ethylphenyl)piperazin-1-yl)-3-
fluorobutyl)benzofuran-2-carboxamide ((R)-C5b)

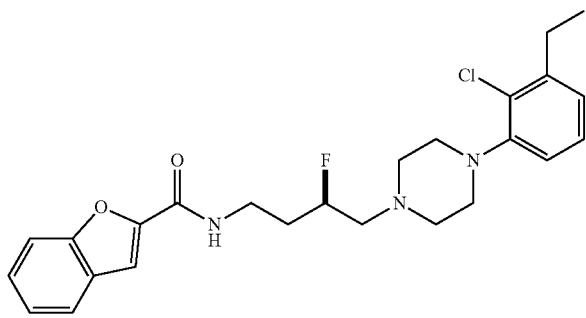 [SMILES: CCc1cccc(N2CCN(C[C@H](F)CCNC(=O)c3cc4ccccc4o3)CC2)c1Cl]

(S)-N-(4-(4-(2-chloro-3-ethylphenyl)piperazin-1-yl)-3-fluorobutyl)benzofuran-2-carboxamide ((S)-C5b)

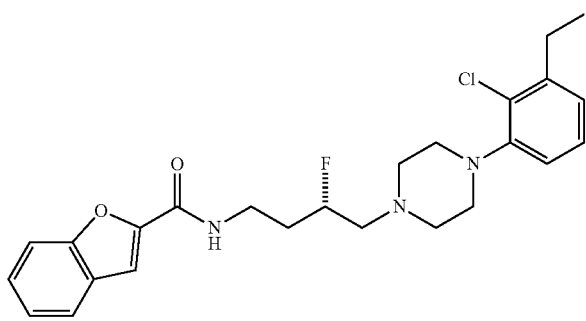 [SMILES: CCc1cccc(N2CCN(C[C@@H](F)CCNC(=O)c3cc4ccccc4o3)CC2)c1Cl]

A compound of Formula (II) or a pharmaceutically acceptable salt thereof, a radioisotope thereof, or a stereoisomer thereof:

Formula (II)

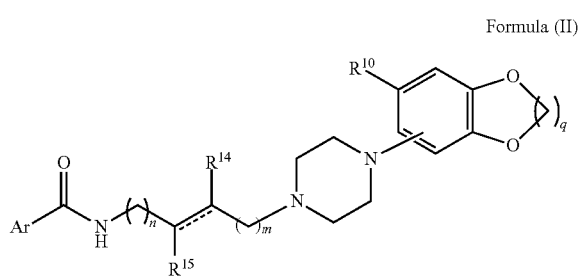

wherein Ar is a heteroaryl which may be optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, mono- ordi- $C_1$-$C_3$alkylamino, or halogen, or Ar is a 3,4-melhylenedioxy-phenyl group; specifically Ar is benzofuranyl, benzolhienyl, imidazolyl, imidazo[1,2-a]pyridinyl, imidazo[2,1-b]thiazolyl, or indolyl; and more specifically Ar is benzofuranyl, benzothienyl, 4-ethyl-1H-imidazolyl, 4-methyl-1H-intidazolyl, imidazo[1,2-a]pyridinyl, 6-methylimidazo[2,1-b]thiazolyl, or indolyl; n is 0, 1, 2, 3, or 4, specifically n is 1 or 2;
m is 0, 1, 2, 3, or 4, specifically m is 1 or 2;
q is 1 or 2;
$R^{10}$ is $C_1$-$C_6$alkyl, specifically $C_2$ alkyl;
$R^{14}$ is H, —OH, or halogen;
$R^{15}$ is H, —OH, or halogen; and
⸺ is a single bond, a double bond (e.g. trans or cis double bond, specifically trans), a cycloalkyl, specifically a $C_3$-$C_6$ cycloalkyl such as a cyclopropyl or cyclohexyl (e.g. trans or cis, specifically trans), or a cycloalkenyl, specifically a $C_3$-$C_6$ cycloalkenyl. In an embodiment, a compound of Formula (I) or a pharmaceutically acceptable salt thereof wherein $R^1$ is H, $R^2$ is —OMe, and $R^3$ is Cl.

In an embodiment, a compound of Formula (II) or a pharmaceutically acceptable salt thereof wherein $R^{10}$ is $C_2$ alkyl.

In an embodiment, a compound of Formula (II) or a pharmaceutically acceptable salt thereof wherein Ar is benzofuranyl, benzothienyl, imidazolyl, imidazo[1,2-a]pyridinyl, imidazo[2,1-b]thiazolyl, or indolyl, where Ar is further optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, or halogen.

In an embodiment, a compound of Formula (II) or a pharmaceutically acceptable salt thereof wherein $R^{10}$ is $C_2$ alkyl, and Ar is benzofuranyl, benzothienyl, imidazolyl, imidazo[1,2-a]pyridinyl, imidazo[2,1-b]thiazolyl, or indolyl, where Ar is further optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, or halogen.

In an embodiment, a compound of Formula (II) or a pharmaceutically acceptable salt thereof wherein $R^{10}$ is $C_2$ alkyl, Ar is benzofuranyl, benzothienyl, imidazolyl, imidazo[1,2-a]pyridinyl, imidazo[2,1-b]thiazolyl, or indolyl, where Ar is further optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, or halogen, m is 1 and n is 1.

In an embodiment, a compound of Formula (II) or a pharmaceutically acceptable salt thereof wherein one of $R^{14}$ and $R^{15}$ is H and the other is —OH or —F.

In an embodiment, a compound of Formula (II) or a pharmaceutically acceptable salt thereof wherein $R^{10}$ is $C_2$ alkyl, and Ar is benzofuranyl, benzothienyl, 4-ethyl-1H-imidazolyl, 4-methyl-1H-imidazolyl, imidazo[1,2-a]pyridinyl, 6-methylimidazo[2,1-b]thiazolyl, or indolyl. Further within this embodiment one of $R^{14}$ and $R^{15}$ is H and the other is —OH or —F.

In an embodiment, a compound of Formula (II) or a pharmaceutically acceptable salt thereof wherein $R^{10}$ is $C_2$ alkyl; Ar is benzofuranyl or indolyl; n is 1 or 2; m is 1 or 2; $R^{14}$ is H, —OH, or halogen, specifically H, —OH, or F; $R^{15}$ is H, —OH, or halogen, specifically H, —OH or F; and ═ is a single bond, a double bond (e.g. trans or cis double bond, specifically trans), a $C_3$-$C_6$ cycloalkyl such as a cyclopropyl or cyclohexyl (e.g. trans or cis, specifically trans), or a $C_3$-$C_6$ cycloalkenyl.

The compounds are described using standard nomenclature. Unless defined otherwise, all technical and scientific terms used herein have the same meaning as is commonly understood by one of ordinary skill in the art to which this disclosure belongs. Unless clearly contraindicated by the context each compound name includes the free acid or free base form of the compound as well hydrates of the compound and all pharmaceutically acceptable salts of the compound.

The term "Formula (I) or (II)", as used herein, encompasses all compounds that satisfy Formula (I) or (II), including any enantiomers, racemates and stereoisomers, as well as all pharmaceutically acceptable salts and radioisotopes of such compounds. The phrase "a compound of Formula (I) or (II)" includes all subgeneric groups of Formula (I) or (II), and so forth, as well as all forms of such compounds, including salts and hydrates, unless clearly contraindicated by the context in which this phrase is used.

Formula (I) or (II) includes all subformulae thereof. In certain situations, the compounds of Formula (I) or (II) may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example, a chiral high performance liquid chromatography (HPLC) column.

Where a compound exists in various tautomeric forms, the compound is not limited to any one of the specific tautomers, but rather includes all tautomeric forms. All isotopes of atoms occurring in the present compounds are contemplated. Isotopes include those atoms having the same atomic number but different mass numbers. By way of general example, and without limitation, isotopes of hydrogen include tritium and deuterium; isotopes of carbon include $^{11}C$, $^{13}C$, and $^{14}C$; and an isotope of fluorine includes $^{18}F$.

The term "active agent", as used herein, means a compound of Formula (I) or (II) that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. All forms are contemplated herein regardless of the methods used to obtain them.

A dash ("—") that is not between two letters or symbols is used to indicate a point of attachment for a substituent. For example, —(CH$_2$)$C_3$-$C_8$cycloalkyl is attached through carbon of the methylene (CH$_2$) group.

"Alkanoyl" is an alkyl group as defined herein, covalently bound to the group it substitutes by a keto (—(C═O)—) bridge. Alkanoyl groups have the indicated number of carbon atoms, with the carbon of the keto group being included in the numbered carbon atoms. For example a $C_2$alkanoyl group is an acetyl group having the formula CH$_3$(C═O)—.

The term "alkyl", as used herein, means a branched or straight chain saturated aliphatic hydrocarbon group having the specified number of carbon atoms, generally from 1 to about 12 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_6$alkyl, $C_1$-$C_4$alkyl, and $C_1$-$C_2$alkyl. When $C_0$-$C_n$ alkyl is used herein in conjunction with another group, for example, (cycloalkyl)$C_0$-$C_4$alkyl, the indicated group, in this case cycloalkyl, is either directly bound by a single covalent bond ($C_0$), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

The term "alkoxy" represents an alkyl group as defined above with the indicated number of carbon atoms attached through an oxygen bridge. Examples of alkoxy include methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

The term "aryl", as used herein, means aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Bicyclic aryl groups may be further substituted with carbon or non-carbon atoms or groups. Bicyclic aryl groups may contain two fused aromatic rings (naphthyl) or an aromatic ring fused to a 5- to 7-membered non-aromatic cyclic group that optionally contains 1 or 2 heteroatoms independently chosen from N, O, and S, for example, a 3,4-methylenedioxy-phenyl group (e.g., a benzo[d][1,3]dioxole). Aryl groups include, for example, phenyl, naphthyl, including 1-naphthyl and 2-naphthyl, and bi-phenyl.

The term "cycloalkyl", as used herein, indicates a saturated hydrocarbon ring group, having only carbon ring atoms and having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

The term "cycloalkenyl", as used herein, means a saturated hydrocarbon ring group, comprising one or more unsaturated carbon-carbon bonds, which may occur in any stable point of the ring, and having the specified number of carbon atoms. Monocyclic cycloalkenyl groups typically have from 3 to about 8 carbon ring atoms or from 3 to 7 (3, 4, 5, 6, or 7) carbon ring atoms. Cycloalkenyl substituents may be pendant from a substituted nitrogen or carbon atom, or a substituted carbon atom that may have two substituents may have a cycloalkenyl group, which is attached as a spiro group. Examples of cycloalkenyl groups include cyclopropenyl, cyclobutenyl, cyclopentenyl, or cyclohexenyl as well as bridged or caged saturated ring groups such as norbornene.

The term "heteroaryl", as used herein, indicates a stable 5- to 7-membered monocyclic or 7- to 10-membered bicyclic heterocyclic ring which contains at least 1 aromatic ring that contains from 1 to 4, or specifically from 1 to 3, heteroatoms chosen from N, O, and S, with remaining ring atoms being carbon. When the total number of S and O atoms in the heteroaryl group exceeds 1, theses heteroatoms are not adjacent to one another. Specifically, the total number of S and O atoms in the heteroaryl group is not more than 2, more specifically the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. In certain embodiments 5- to 6-membered heteroaryl groups are used. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Haloalkyl" includes both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined herein attached through an oxygen bridge (oxygen of an alcohol radical).

"Halo" or "halogen" is any of fluoro, chloro, bromo, and iodo.

"Mono- and/or di-alkylamino" is a secondary or tertiary alkyl amino group, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example, a pyridyl group substituted by oxo is a pyridone. A stable compound or stable structure is meant to imply a compound that is sufficiently robust to survive isolation from a reaction mixture, and subsequent formulation into an effective therapeutic agent.

Unless otherwise specified substituents are named into the core structure. For example, it is to be understood that when (cycloalkyl)alkyl is listed as a possible substituent the point of attachment of this substituent to the core structure is in the alkyl portion, or when arylalkyl is listed as a possible substituent the point attachment to the core structure is the alkyl portion.

Suitable groups that may be present on a "substituted" or "optionally substituted" position include, but are not limited to, halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothienyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

The term "dosage form", as used herein, means a unit of administration of an active agent. Examples of dosage forms include tablets, capsules, injections, suspensions, liquids, emulsions, creams, ointments, suppositories, inhalable forms, transdermal forms, and the like. An exemplary dosage form is a solid oral dosage form.

The term "pharmaceutical compositions", as used herein, are compositions comprising at least one active agent, such as a compound or salt of Formula (I) or (II), and at least one other substance, such as a carrier. Pharmaceutical compositions meet the U.S. FDA's GMP (good manufacturing practice) standards for human or non-human drugs. The pharmaceutical compositions can be formulated into a dosage form.

The term "pharmaceutically acceptable salt", as used herein, includes derivatives of the disclosed compounds in which the parent compound is modified by making inorganic and organic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in Remington's Pharmaceutical Sciences, 17th ed., Mack Publishing Company, Easton, Pa., p. 1418 (1985).

In an embodiment, a pharmaceutical composition for the use in the methods described herein comprises i) an opioid analgesic or a pharmaceutically acceptable salt thereof, a Medication Assisted Treatment agent or a pharmaceutically acceptable salt thereof, or a combination thereof; and further comprises a selective dopamine D3 receptor antagonist/partial agonist compound or a pharmaceutically acceptable salt thereof, optionally further comprising a pharmaceutically acceptable carrier. Also provided are pharmaceutical compositions comprising a compound of Formula (I), (II), or a pharmaceutically acceptable salt thereof and a pharmaceutically acceptable carrier. Further provided are pharmaceutical compositions comprising an opioid analgesic or a pharmaceutically acceptable salt thereof, a Medication Assisted Treatment agent and a pharmaceutically acceptable salt thereof, or a combination thereof; and a pharmaceutically acceptable carrier.

The term "carrier", as used herein, applied to pharmaceutical compositions refers to a diluent, excipient, or vehicle with which an active compound is provided.

The compounds can be administered as the neat chemical, or administered as a pharmaceutical composition. Accordingly, an embodiment provides pharmaceutical compositions comprising a compound or pharmaceutically acceptable salt of Formula (I) or (II), together with a pharmaceutically acceptable carrier. The pharmaceutical composition may contain a compound or salt of Formula (I) or (II) as the only active agent, or may contain one or more additional active agents including the opioid analgesic and/or Medication Assisted Treatment agent. Another embodiment provides pharmaceutical compositions comprising an opioid analgesic or pharmaceutically acceptable salt thereof, a Medication Assisted Treatment agent or a pharmaceutically acceptable salt thereof, or a combination thereof, together with a pharmaceutically acceptable carrier.

The compound of Formula (I) or (II), the opioid analgesic, and the Medication Assisted Treatment agent, independently may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, a subcutaneous formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, for example, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils.

The pharmaceutical compositions can include oral dosage forms having "controlled-release" meaning release of the active agent (compound of Formula (I), (II), opioid analgesic, MAT agent) is controlled or modified over a period of time. Controlled can mean, for example, sustained-, delayed- or pulsed-release at a particular time. Alternatively, controlled can mean that the release of the active agent is extended for longer than it would be in an immediate-release dosage form, e.g., at least over several hours. "Sustained-release" or "extended-release" include the release of the active agent at such a rate that blood (e.g., plasma) levels are maintained within a therapeutic range for at least about 8 hours, specifically at least about 12 hours, and more specifically at least about 24 hours after administration at steady-state. The term steady-state means that a plasma level for a given active agent has been achieved and which is maintained with subsequent doses of the drug at a level which is at or above the minimum effective therapeutic level for a given active agent. By "delayed-release", it is meant that there is a time-delay before significant plasma levels of the active agent are achieved. A delayed-release formulation of the active agent can avoid an initial burst of the active agent, or can be formulated so that release of the active agent in the stomach is avoided and absorption occurs in the small intestine.

Controlled-release oral dosage forms, specifically sustained-release dosage forms, can include wax or polymer coated tablets, caplets, or drug cores; time-release matrices; or a combination thereof. Release rate controlling materials suitable for the time-release matrices include, e.g., acrylic polymers such as acrylic acid and methacrylic acid copolymers, methyl methacrylate copolymers, poly(methyl)methacrylates, and the like; alkylcelluloses, hydroxyalkylcelluloses, and hydroxylalkyl alkylcelluloses such as methyl cellulose, ethylcellulose, hydroxypropylcellulose, hydroxypropyl methylcellulose, and the like; shellac; zein; hydrogenated vegetable oil; polyvinylpyrrolidine; vinyl acetate copolymers; polyethylene oxide; and a combination thereof, wherein the release rate controlling matrix material is used in amounts of about 1 wt % and about 80 wt % based on the total weight of the oral dosage form, specifically about 5 wt % to about 50 wt %. Release rate controlling coating materials include polymer such as alkylcelluloses hydroxyalkylcelluloses, and hydroxylalkyl alkylcelloses such as methyl cellulose, ethylcellulose, hydroxypropylcellulose, hydroxypropyl methylcellulose, and the like; poly(meth)acrylates having pH-dependent or pH-independent release, and the like; wax; and a combination thereof. The coatings can optionally include a plasticizer, a pore forming agent, a colorant, or a combination thereof.

In an embodiment, the Medication Assisted Treatment agent, e.g., buprenorphine, is provided in an extended release formulation as a subcutaneous injection for once or more weekly, once or more monthly, etc.

The pharmaceutical compositions can be formulated for oral administration. These compositions can contain between 0.1 and 99 weight percent ("wt. %") of a compound of Formula (I), (II), or opioid analgesic or Medication Assisted Treatment agent, and usually at least about 5 wt. %. Some embodiments contain from about 25 wt. % to about 50 wt. % or from about 5 wt. % to about 75 wt. % of a compound of Formula (I) or (II).

The selective dopamine D3 receptor antagonist/partial agonist compound of Formula (I) or (II) may be administered to the patient as a daily dosage regimen in unit dosage form one, two, three, or more times daily, specifically once daily. Unit dosage forms for oral administration can contain about 0.5 mg to about 500 mg, specifically about 1 mg to about 400 mg, more specifically about 3 mg to about 200 mg, and yet more specifically about 5 mg to about 100 mg of the compound of Formula (I) or (II). Unit dosage amounts for parenteral administration can contain about 0.1 mg to about 200 mg, specifically about 1 mg to about 100 mg, and more specifically about 2 to about 50 mg of the compound of Formula (I) or (II).

The compound of Formula (I) or (II) can be administered to the patient for a period of time for continuous therapy, for example one or more weeks, two or more weeks, three or more weeks, a month, two or more months, and the like, optionally in combination with the Medication Assisted Treatment agent. The compound of Formula (I) or (II) can be administered to the patient for a period of time prior to the start of the administration of the opioid analgesic, e.g. 1, 2, 3, 4, 5, 6, 7, 8, 9, 10, or more days prior to the initiation of opioid analgesic administration, optionally in combination with the Medication Assisted Treatment agent. The compound of Formula (I) or (II) can be administered to the patient for the duration of time of the opioid analgesic therapy, and further optionally administered for a period of time after discontinuation of the opioid analgesic therapy, e.g. 1, 2, 3, 4, 5, 6, 7, 8, 9, 10, or more days. In one embodiment, the compound of Formula (I) or (II) is administered to the patient 1, 2, 3, 4, 5, 6, 7, 8, 9, 10, or more days prior to the initiation of opioid analgesic administration, further administered for the duration of time of the opioid analgesic therapy, and optionally administered for 1, 2, 3, 4, 5, 6, 7, 8, 9, 10, or more days after discontinuation of the opioid analgesic therapy, optionally in combination with the Medication Assisted Treatment agent.

The pharmaceutical composition can be formulated in a package or kit comprising the pharmaceutical composition containing a compound of Formula (I), (II), or a salt thereof in a container and further comprising instructions for using the composition in order to elicit a therapeutic effect in a patient.

The pharmaceutical composition can also be formulated in a package or kit comprising the pharmaceutical composition of Formula (I), (II), or a salt thereof and optionally the opioid analgesic, the Medication Assisted Treatment agent, or a combination thereof in a container and further comprising instructions for using the composition in combination with an opioid analgesic to treat a patient suffering from pain or to treat an opioid use disorder, mitigate the development of opioid addiction, reduce the severity of opioid withdrawal symptoms, or reduce or prevent opioid relapse.

In an embodiment, a package or kit for the treatment of pain comprises a container comprising at least one formulation comprising a therapeutically effective amount of an opioid analgesic (e.g. about 10 to about 40 mg oxycodone) or a pharmaceutically acceptable salt thereof and a selective dopamine D3 receptor antagonist/partial agonist compound or a pharmaceutically acceptable salt thereof; the kit further comprising instructions for the use of the at least one formulation, including a dosing regimen, wherein the oxycodone and the selective dopamine D3 receptor antagonist/partial agonist compound are in the same formulation or in separate formulations.

In another embodiment, a package or kit for the treatment of pain comprises a container comprising at least one formulation comprising a therapeutically effective amount of a selective dopamine D3 receptor antagonist/partial agonist compound or a pharmaceutically acceptable salt thereof; the kit further comprising instructions for the use of the at least one formulation in the treatment of pain using an opioid analgesic, including a dosing regimen of when to administer the selective dopamine D3 receptor antagonist/partial agonist compound formulation and optionally when to administer the opioid analgesic. Within this embodiment, the opioid analgesic may be separate from the package or kit. In another embodiment, the package or kit comprises both the at least one formulation comprising a therapeutically effective amount of a selective dopamine D3 receptor antagonist/partial agonist compound and at least one formulation comprising a therapeutically effective amount of the opioid analgesic.

In an embodiment, a method for treating substance use disorders (e.g. stimulants including cocaine, heroin, methamphetamine, and the like), opioids (including hydromorphone, hydrocodone, oxycodone, oxymorphone, ethylmorphine buprenorphine, morphine, codeine, etc.), cannabis, alcohol, nicotine, and the like), schizophrenia and related mental disorders, cognitive disorders, impulsivity, obesity, depression, a bipolar disorder, or dyskinesias associated with Parkinson's disease (PD) or treatment of PD with L-DOPA comprises providing an effective amount of a compound or salt of Formula (I) or (II) to a patient in need of such treatment. Alternatively, the compound or salt of Formula (I) or (II) may be provided in the form of a pharmaceutical composition.

This invention is further illustrated by the following examples that should not be construed as limiting.

EXAMPLES

Example 1: Synthesis of Piperazine Butandiyl/2-butendiyl Arylcarboxamide Derivatives Anhydrous solvents were purchased from Aldrich and were used without further purification except for tetrahydrofuran, which was freshly distilled from sodium-benzophenone ketyl. All other chemicals and reagents were purchased from Sigma-Aldrich Co. LLC, Combi-Blocks, TCI America, Acros Organics, Maybridge, and Alfa Aesar. All amine final products were converted into the oxalate salt. Spectroscopic data and yields refer to the free base form of compounds. Teledyne ISCO CombiFlash Rf or glass flash column chromatography was performed using silica gel (EMD Chemicals, Inc.; 230-400 mesh, 60 Å). $^1$H and $^{13}$C NMR spectra were acquired using a Varian Mercury Plus 400 spectrometer at 400 MHz and 100 MHz, respectively.

Chemical shifts are reported in parts-per-million (ppm) and referenced according to deuterated solvent for $^1$H spectra (CDCl$_3$, 7.26, CD$_3$OD, 3.31 or DMSO-d$_6$, 2.50) and $^{13}$C spectra (CDCl$_3$, 77.2, CD$_3$OD, 49.0 or DMSO-d$_6$, 39.5). Gas chromatography-mass spectrometry (GC/MS) data were acquired (where obtainable) using an Agilent Technologies (Santa Clara, CA) 6890N GC equipped with an HP-5MS column (cross-linked 5% PH ME siloxane, 30 m×0.25 mm i.d.×0.25 µm film thickness) and a 5973 mass-selective ion detector in electron-impact mode. Ultrapure grade helium was used as the carrier gas at a flow rate of 1.2 mL/minute (min). The injection port and transfer line temperatures were 250 and 280° C., respectively, and the oven temperature gradient used was as follows: the initial temperature (100° C.) was held for 3 min and then increased to 295° C. at 15° C./min over 13 min, and finally maintained at 295° C. for 10 min. Combustion analysis was performed by Atlantic Microlab, Inc. (Norcross, GA) and the results agree within ±0.4% of calculated values. cLogP and polar surface area (PSA) values were calculated using ChemDraw Professional Ultra 15.0. Melting point determination was conducted using a Thomas-Hoover melting point apparatus or an OptiMelt automated melting point system and are uncorrected. On the basis of NMR and combustion data, all final compounds are ≥95% pure. Optical rotations were determined using a Jasco DIP-370 polarimeter.

Abbreviations used: CDI, 1,1'-carbonyldiimidazole; DMF, dimethylformamide; h, hour; min, minute; RT, room temperature; THF, tetrahydrofuran.

Generalized synthetic strategies used for the piperazine butandiyl/2-butendiyl arylcarboxamide derivatives are shown in Schemes 1-5.

Scheme 1. Synthesis of (±), (R), and (S)-29

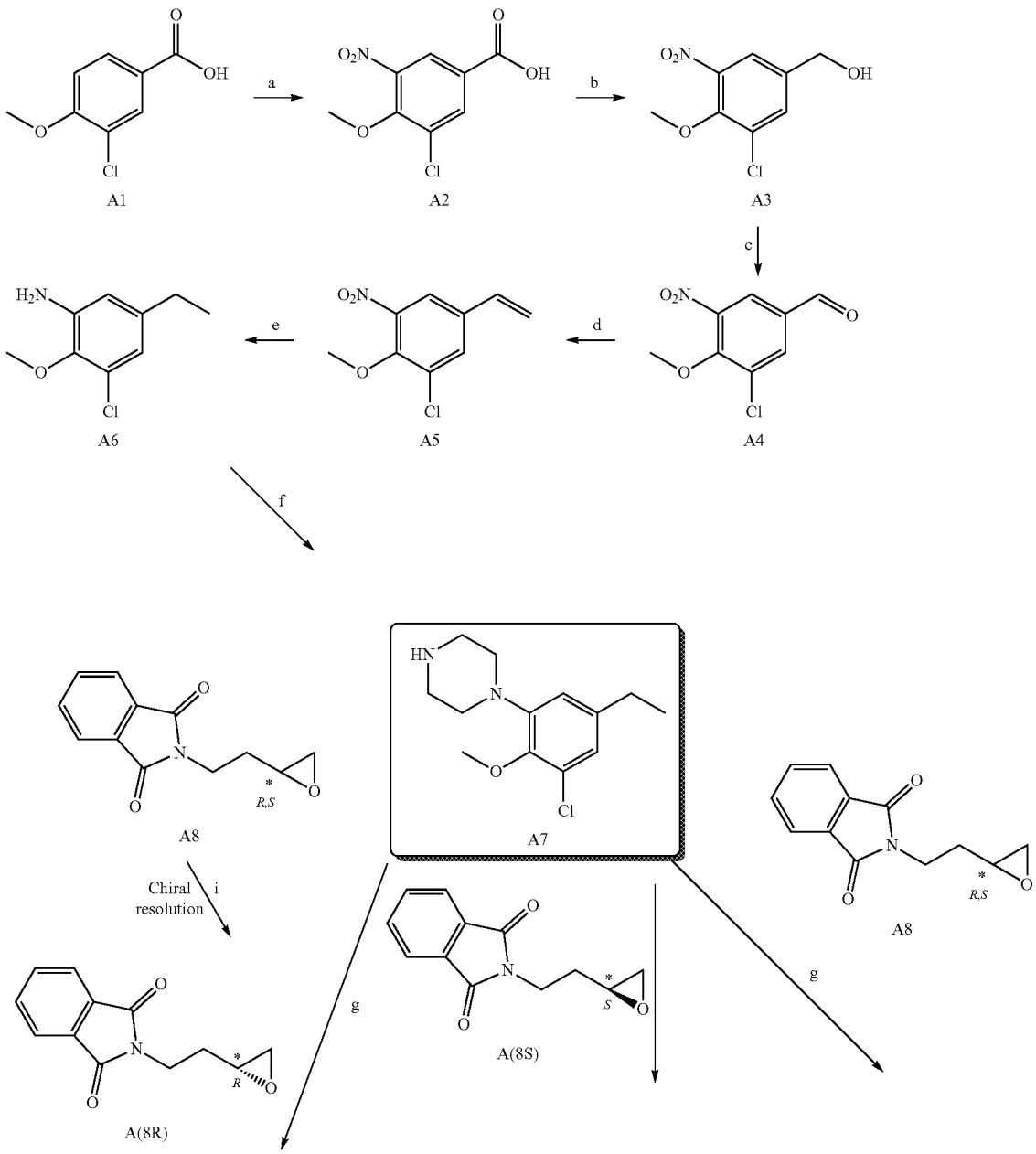

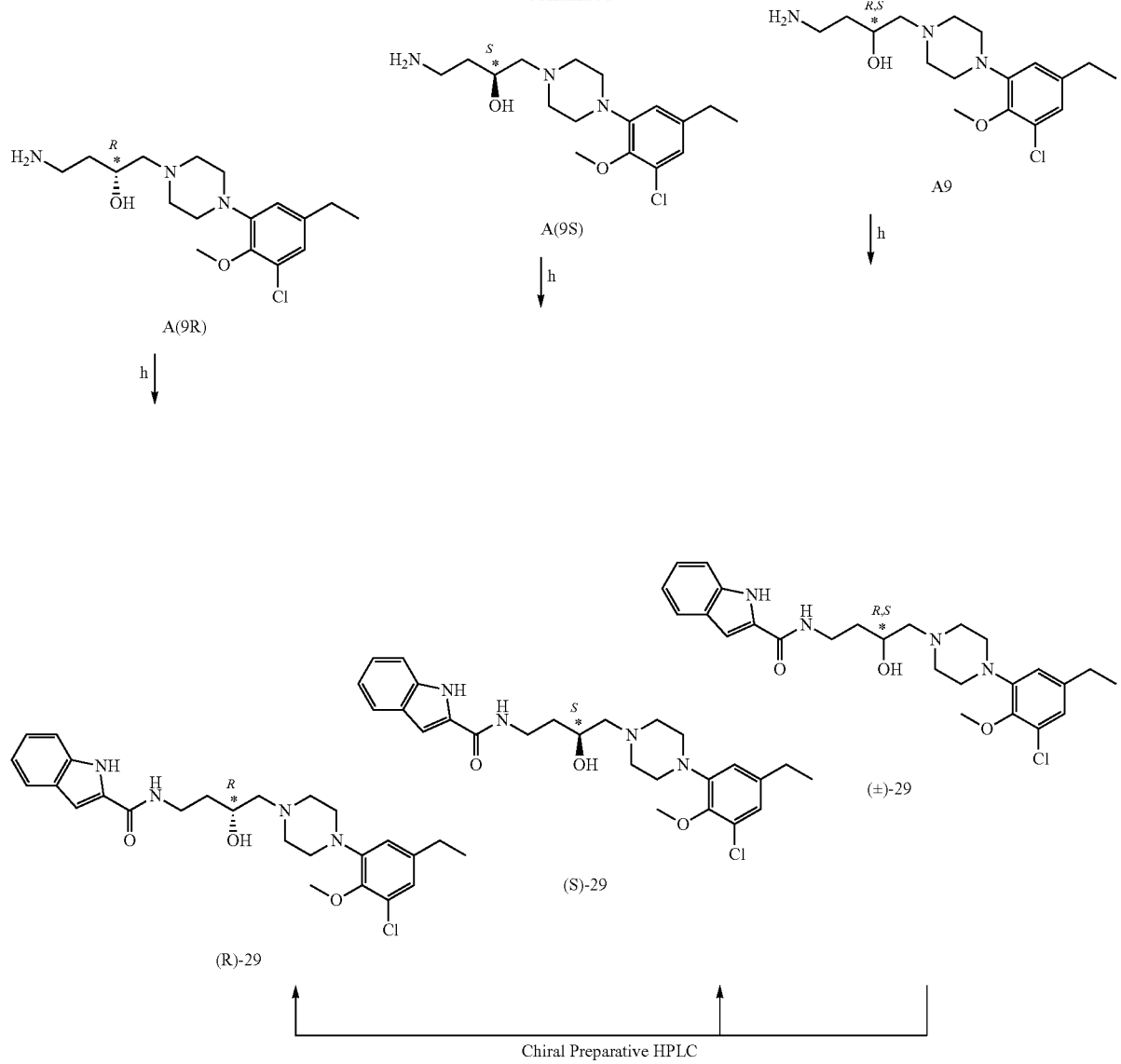

Reagents and conditions: (a) fuming HNO₃, 0° C. to room temperature, 2 h; (b) BH₃•CS₂, 12 h; (c) PCC, CH₂Cl₂, overnight; (d) Ph₃P + CH₃Br, Lithium tert-butoxide, THF-78 to 0 then room temperature, 8 h; (e) 10% Pd/C, H₂, 50 psi, EtOAc, 45 mins; (f) bis(2-chloroethyl)amine•HCl, diethyleneglycol monoethylether, 150° C., 7 h; (g) 1) IPA, reflux, 3 h 2) hydrazine, EtOH, reflux, overnight; (h) ArCOOH, EDC/HoBt, DIPEA, DCM/DMF, 0° C. to rt; (i) (Salen)Co(III)(OAc) complex, H₂O, THF, 72 h.

Scheme 2. Synthesis of (±), (R), and (S)-19

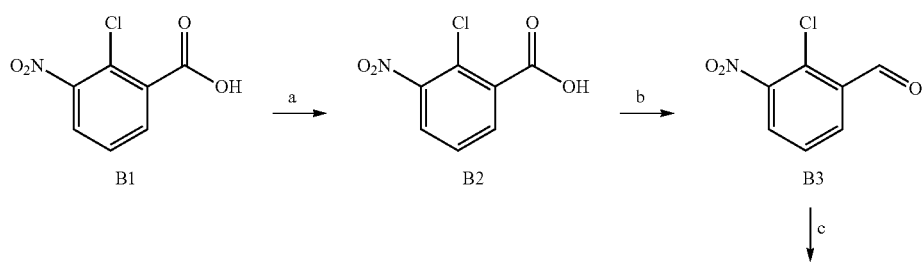

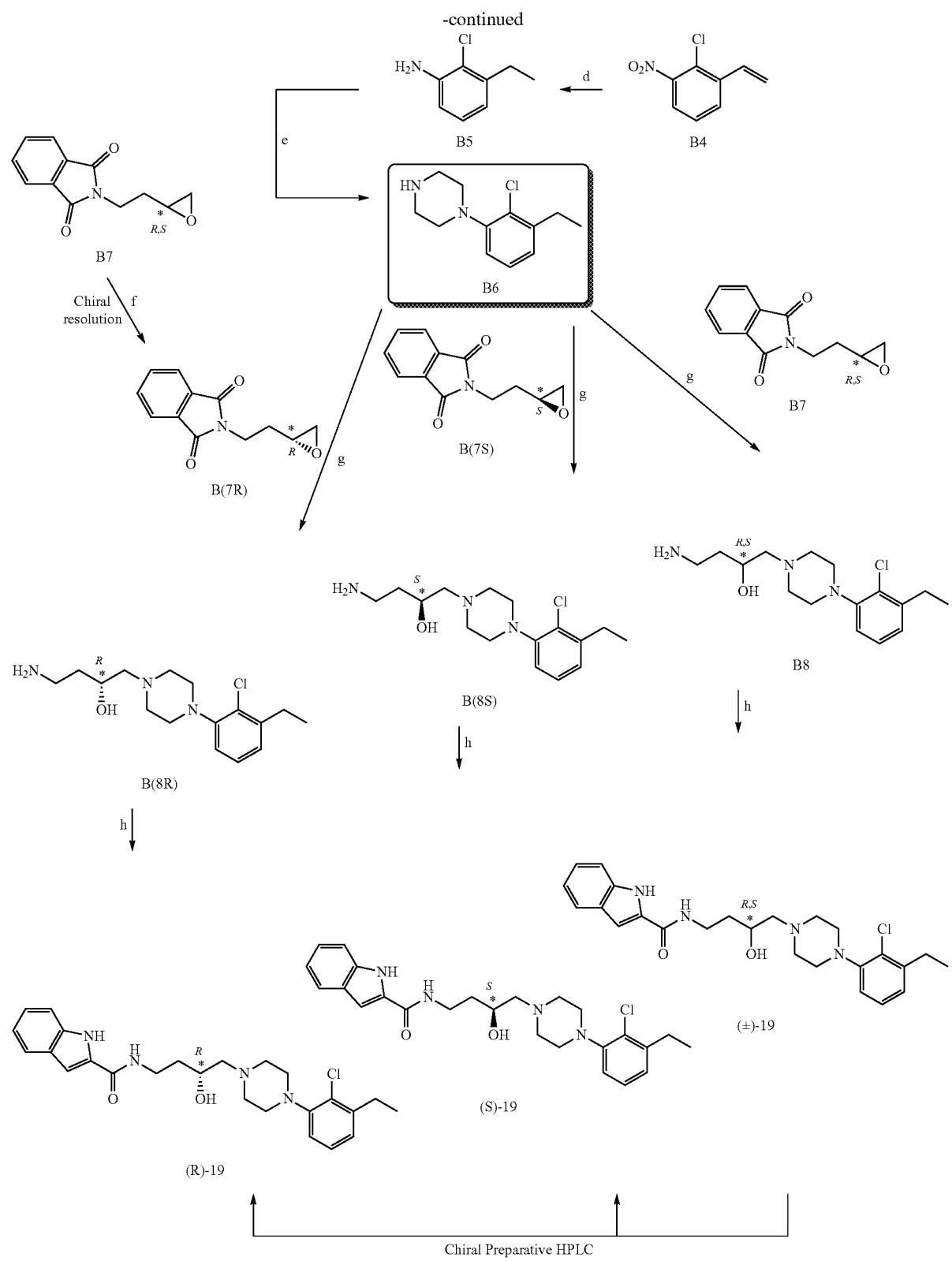
Reagents and conditions: (a) BH₃•CS₂, 12 h; (b) PCC, CH₂Cl₂, overnight; (c) Ph₃P + CH₃Br, Lithium tert-butoxide, THF-78 to 0 then room temperature, 8 h; (d) 10% Pd/C, H₂, 50 psi, EtOAc, 45 mins; (e) bis(2-chloroethyl)amine•HCl, diethyleneglycol monoethylether, 150° C., 7 h; (f) 1) IPA, reflux, 3 h 2) hydrazine, EtOH, reflux, overnight; (g) ArCOOH, EDC/HoBt, DIPEA, DCM/DMF, 0° C. to rt; (h) (Salen)Co(III)(OAc) complex, H₂O, THF, 72 h.

Scheme 3a. Synthesis of C4a-b and C5a-b
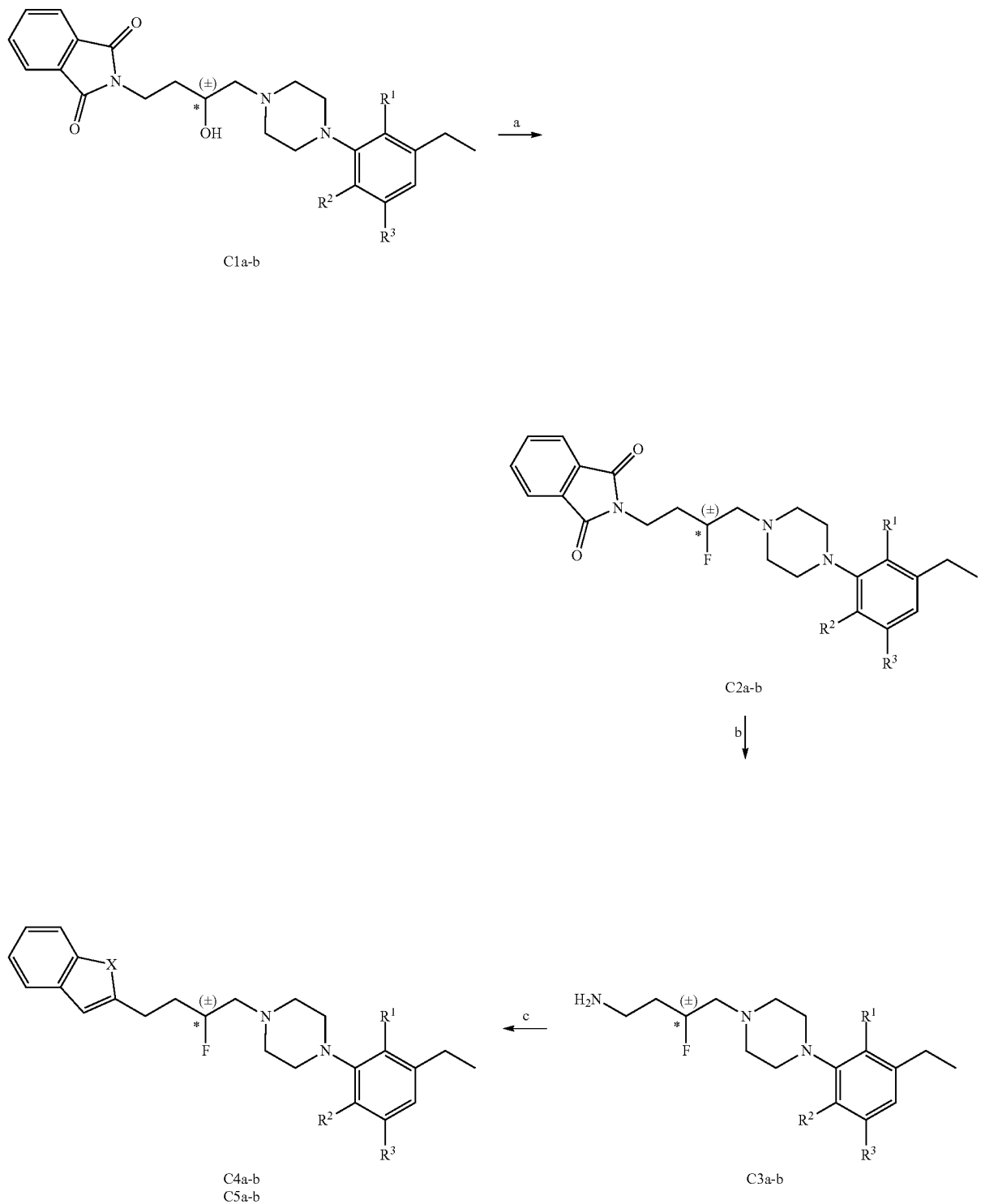
C4a R¹ = H, R² = OMe, R³ = Cl, X = NH
C4b R¹ = H, R² = OMe, R³ = Cl, X = O
C5a R¹ = Cl, R² = H, R³ = H, X = NH
C5b R¹ = Cl, R² = H, R³ = H, X = O
C1a-3a R¹ = H, R² = OMe, R³ = Cl
C1b-3b R¹ = Cl, R² = H, R³ = H
Reagents and conditions: (a) DAST, Dry DCM, -78° C., overnight; (b) hydrazine, EtOH, reflux, overnight; (c) ArCOOH, EDC.Hobt, DIPEA, DCM/DMF, 0° C. to room temperature.

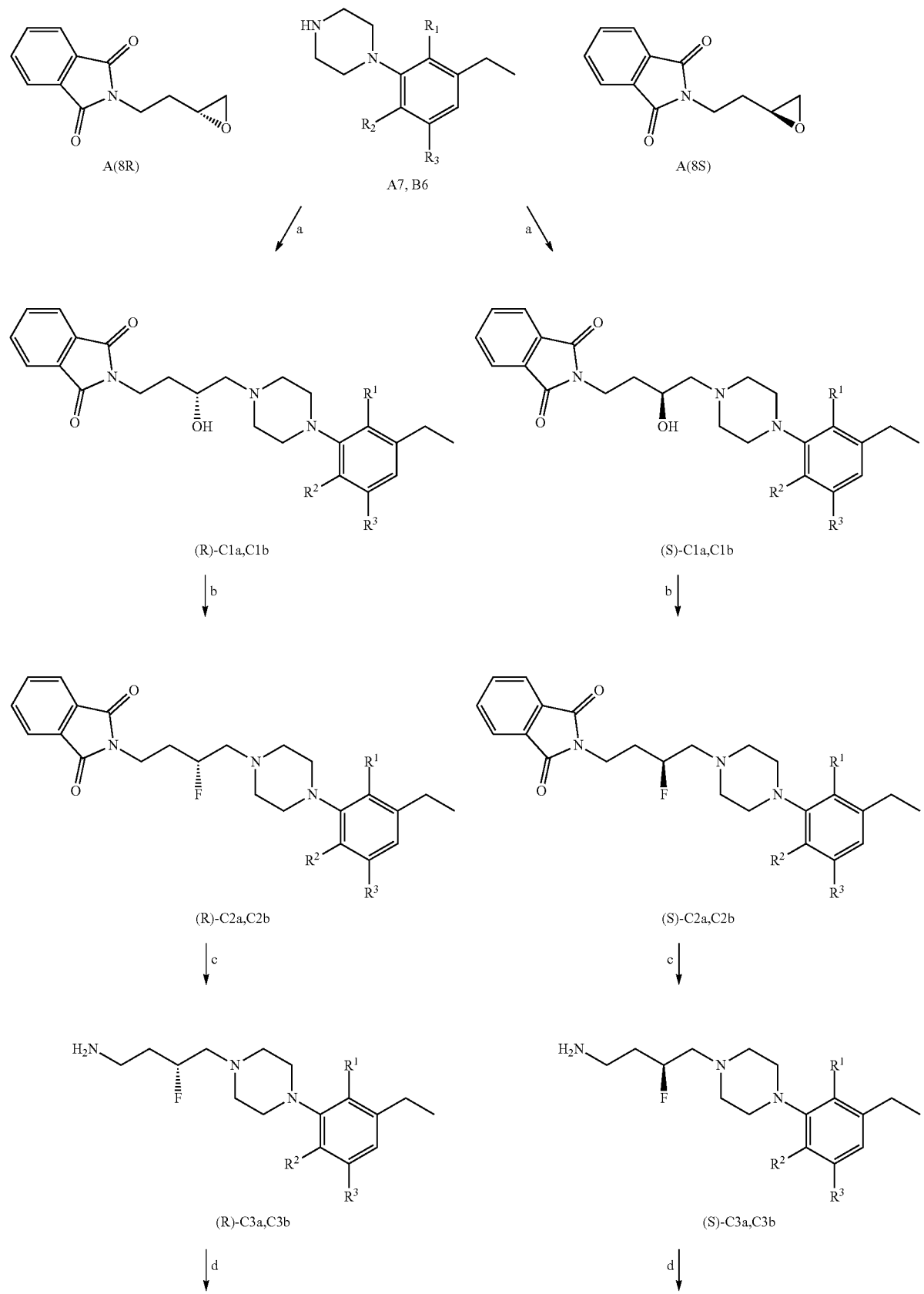
Scheme 3b. Synthesis of (R)- and (S)-3-Fluoro analogues<sup>a</sup>

39 40

-continued

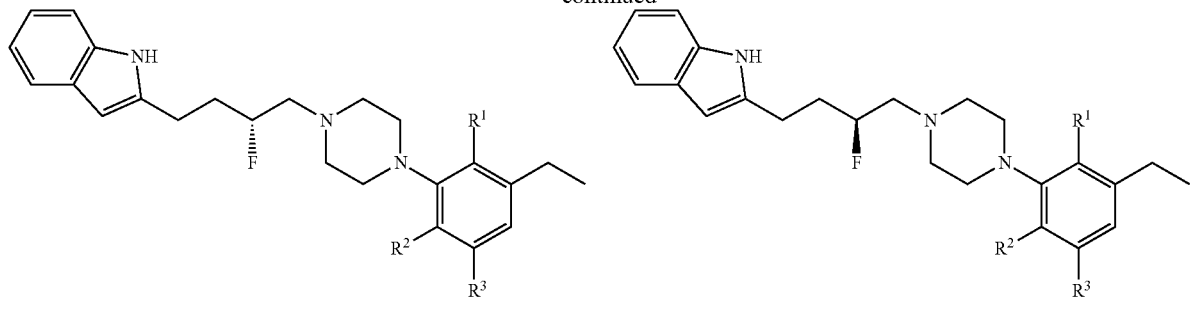

(R)-C4a,C5a  (S)-C4a,C5a (R)-C1a, (R)-C2a, (R)-C3a, (R)-C4a, (S)-C1a, (S)-C2a, (S)-C3a, (S)-C4a
$R^1$ = H, $R^2$ = OMe, $R^3$ = Cl
(R)-C1b, (R)-C2b, (R)-C3b, (R)-C5a, (S)-C1b, (S)-C2b, (S)-C3b, (S)-C5a
$R^1$ = Cl, $R^2$ = H, $R^3$ = H

[a]Reagents and conditions: (a) 2-PrOH, reflux, 3 h; (b) DAST, anhydrous DCM, -78° C. to rt, overnight; (c) hydrazine, EtOH, reflux, overnight; (d) Indole-2-carboxylic acid, EDC/HOBt, DIPEA, CHCl3/DMF, 0° C. to rt 8 h.

Scheme 4. Synthesis 35

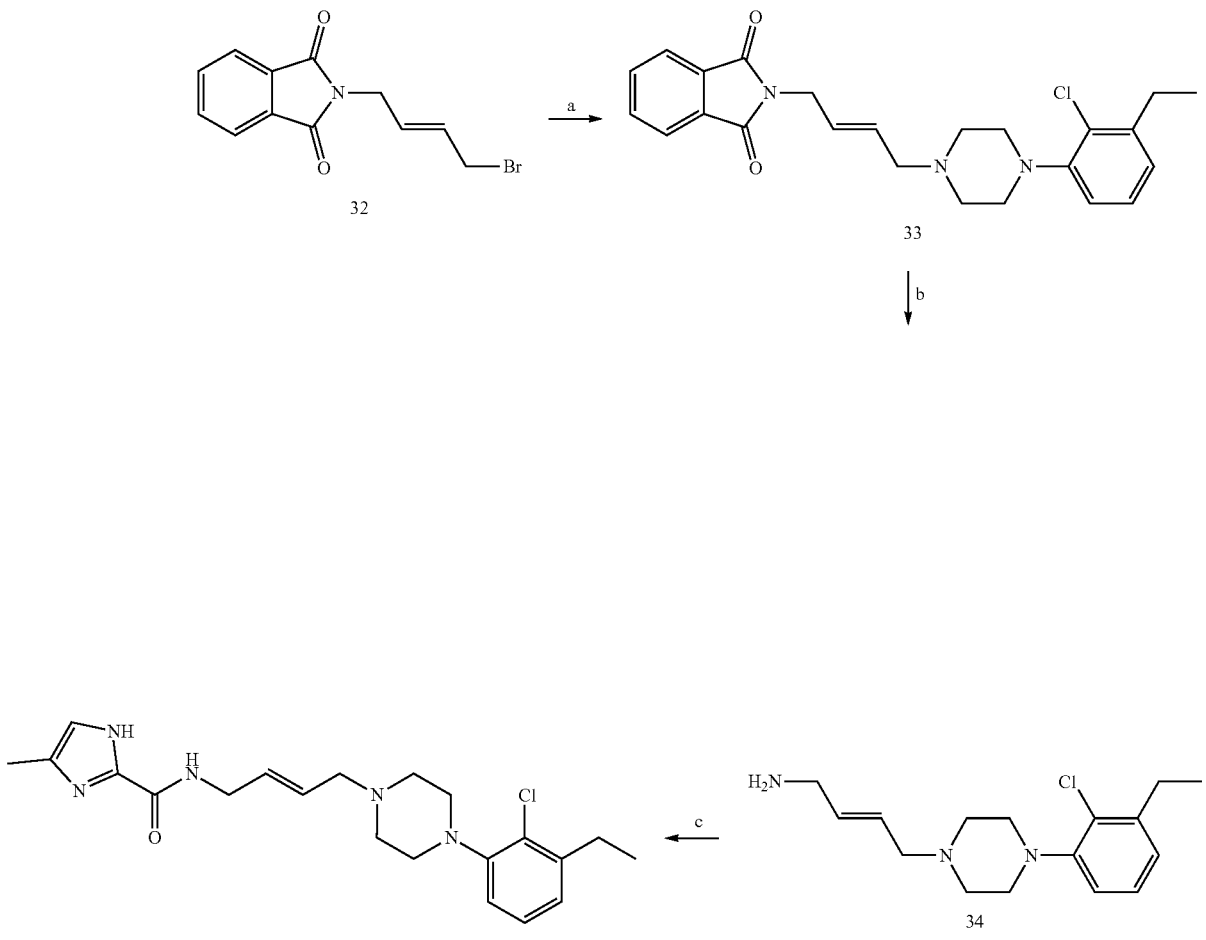

Reagents and conditions: (a) B6, K2CO3, acetone, reflux, overnight; (b) hydrazine, EtOH, reflux, overnight; (c) 4-methyl-1H-imidazole-2-carboxylic acid, CDI, THF, 0° C. to RT, overnight.

Scheme 5. Synthesis of 40

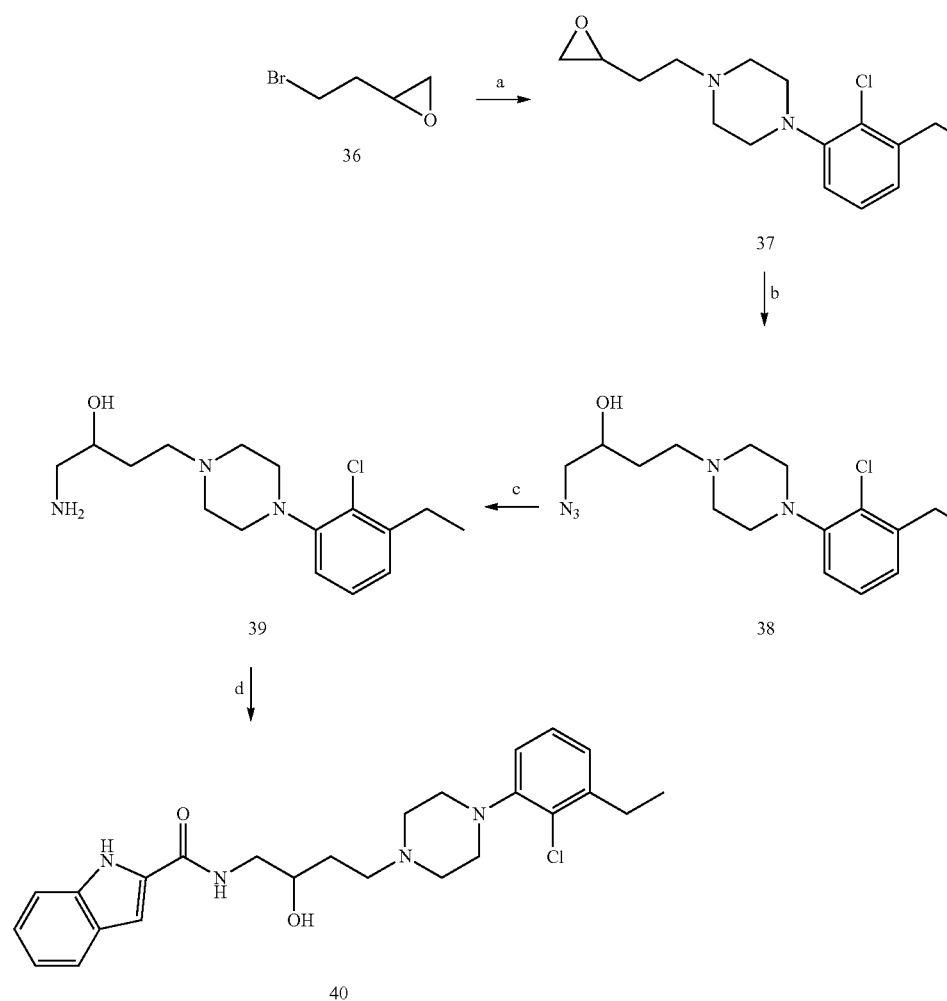

Reagents and conditions: (a) B6, K₂CO₃, acetone, reflux, overnight; (b) NaN₃, NH₄Cl, DMF, 100° C., 6 h; (c) 10% Pd/C, H₂, 50 psi, (d) Indole-2-COOH, CDI, THF, 0° C. to RT.

Scheme 6. Synthesis of 3,4-(methylenedioxy) analogues[a]

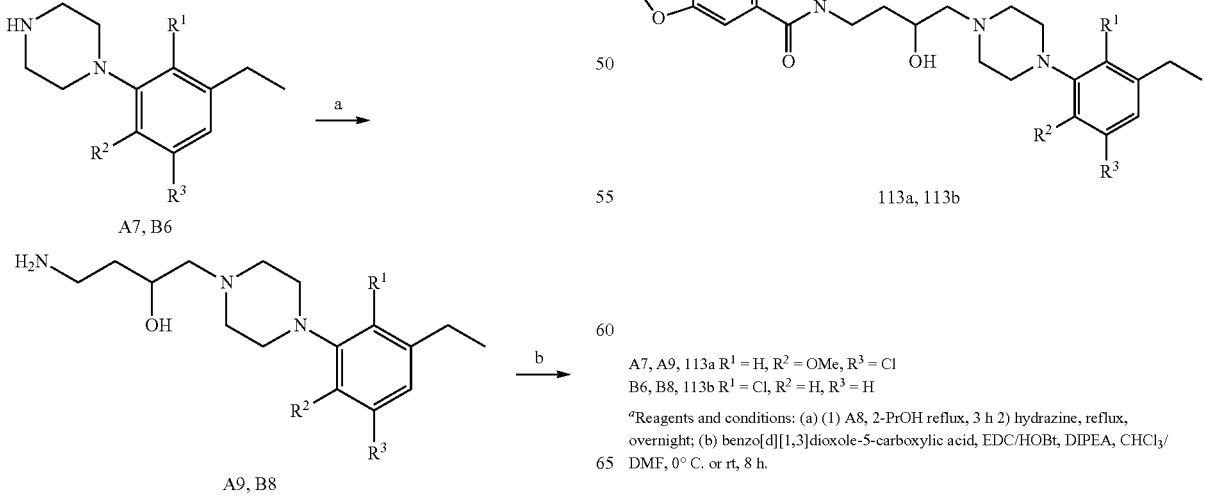

A7, A9, 113a R¹ = H, R² = OMe, R³ = Cl
B6, B8, 113b R¹ = Cl, R² = H, R³ = H

[a]Reagents and conditions: (a) (1) A8, 2-PrOH reflux, 3 h 2) hydrazine, reflux, overnight; (b) benzo[d][1,3]dioxole-5-carboxylic acid, EDC/HOBt, DIPEA, CHCl₃/DMF, 0° C. or rt, 8 h.

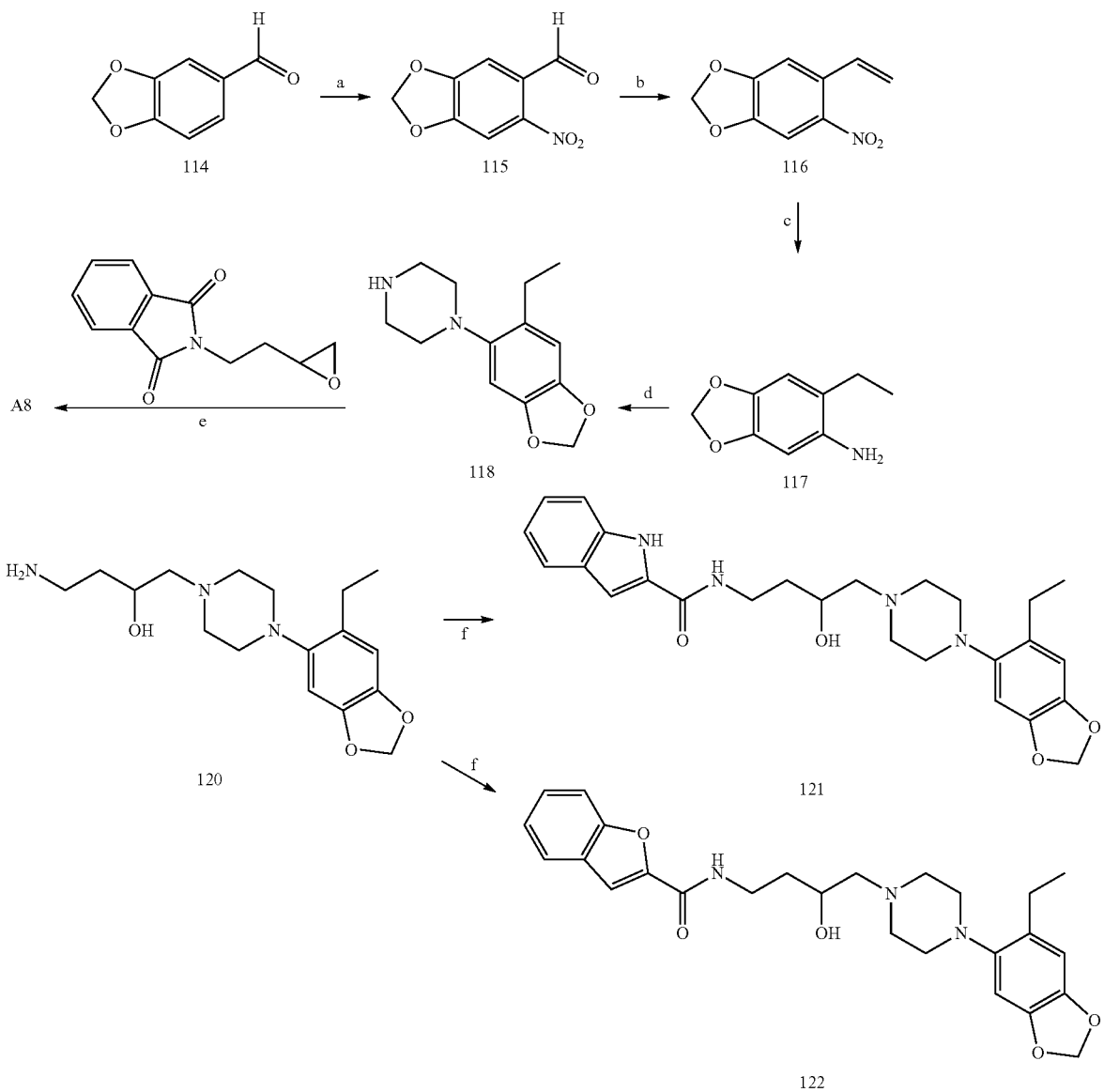

Scheme 7. Synthesis of 3,4-(methylenedioxy) analogues[a]

[a]Reagents and conditions: (a) Fuming HNO₃, 0° C. to rt, 2 h; (b) Methyltriphenylphosphonium bromide, lithium tert-butoxide, THF -78 to 0° C. to rt, 8 h; (c) 10% Pd/C, H₂, 50 psi, EtOAc, 45 min; (d) bis(2-chloroethyl)amine•HCl, diethyleneglycol monoethylether, 150° C., 7 h; (e) 1) 2-PrOH, reflux, 3 h, 2) hydrazine, reflux, overnight; (f) Indole-2-carboxylic acid for 121; benzfuran-2-carboxylic acid for 22, EDC/HOBt, DIPEA, CHCl₃/DMF, 0° C. to rt 8 h.

3-Chloro-4-methoxy-5-nitrobenzoic acid (A2): 3-chloro-4-methoxybenzoic acid (5.0 g, 26.79 mmol) was added in small portions to cold fuming HNO$_3$ (90%, 25 mL) at 0-5° C. The reaction mixture was allowed to warm to 20° C. and stirred for an additional 2 h. Cold water (50 mL) was added, and the precipitated product was extracted in CHCl$_3$ and washed with brine solution and concentrated. The product was purified by flash chromatography using 8% MeOH/CHCl$_3$ as eluent to provide 5.28 g (85%) of product. $^1$H NMR (400 MHz, CD$_3$OD) 8.27 (s, 1H), 8.22 (s, 1H), 4.02 (s, 3H); $^{13}$C NMR (100 MHz, CD$_3$OD) δ 165.9, 153.9, 146.4, 136.3, 131.56, 125.9, 63.2; GC-MS (EI) m/z 231 (M$^+$).

(3-Chloro-4-methoxy-5-nitrophenyl)methanol (A3): Borane dimethyl sulfide complex (10 M, 3.072 g, 40.44 mmol) was added dropwise to a solution of A2 (5.28 g, 22.85 mmol) in THF (60 mL) at 0-5° C. The mixture was allowed to come to RT and stirred overnight. The reaction mixture was cooled to 0-5° C. and quenched carefully by dropwise addition of MeOH. The reaction mixture was evaporated to give 4.7 g of crude product and used directly in the next step without further purification. $^1$H NMR (400 MHz, CDCl$_3$) 8.49-8.38 (m, 2H), 5.50 (s, 2H), 4.82 (m, 3H), 3.70 (bs, 1H); $^{13}$C NMR (100 MHz, CDCl$_3$) δ 148.9, 145.2, 137.9, 132.5, 130.6, 121.3, 63.1, 62.5; GC-MS (EI) m/z 217 (M$^+$).

3-Chloro-4-methoxy-5-nitrobenzaldehyde (A4) (Mizuhara et al. Structure-activity relationship study of phenylpyrazole derivatives as a novel class of anti-HIV agents. *Bioorg. Med. Chem. Lett.* 2013, 23, 4557-61): Pyridinium chlorochromate (PCC, 9.31 g, 43.20 mmol) was added to a solution of A3 (4.7 g, 21.60 mmol) in $CH_2Cl_2$ (100 mL). The reaction mixture was stirred overnight and filtered through a Celite pad. The product was purified by flash chromatography using 20% EtOAc/hexanes as eluent to provide 4.0 g (85%) of the product as a yellow solid. $^1$H NMR (400 MHz, $CDCl_3$) 9.94 (s, 1H), 8.19 (d, J=2.0 Hz, 1H), 8.13 (d, J=2.0 Hz, 1H), 4.10 (s, 3H); $^{13}$C NMR (100 MHz, $CDCl_3$) δ 187.8, 154.4, 145.7, 134.5, 132.2, 131.9, 124.8, 63.0; GC-MS (EI) m/z 215 (M$^+$).

1-Chloro-2-methoxy-3-nitro-5-vinylbenzene (A5): Lithium tert-butoxide (4.46 g, 55.81 mmol) was added dropwise to a suspension of methylitriphenylphosphonium bromide (7.90 g, 22.32 mmol) in dry THF (100 mL) at −78° C. under argon. The reaction mixture was allowed to warm to 0-20° C. and stirred for 3 h and noticed that the formation of yellow precipitate. The solution of A4 (4.0 g, 18.60 mmol) in THF (50 mL) was added dropwise over 30 min. The reaction mixture was maintained at 20° C. and stirred for 8 h. The reaction mixture was quenched with sat. $NH_4Cl$ solution (50 mL) and the THF was removed under vacuum. The crude product was extracted with EtOAc (3×25 mL). The organic layer was combined, dried, concentrated and purified using flash chromatography with 5% Diethyl ether/hexanes as eluent to provide 3.17 g (85%) of the product as a yellow solid. $^1$H NMR (400 MHz, $CDCl_3$) 7.59 (s, 1H), 7.51 (s, 1H), 6.55-6.47 (m, 1H), 5.69 (d, J=16 Hz, 1H), 5.32 (d, J=10.8 Hz, 1H), 3.92 (s, 3H); $^{13}$C NMR (100 MHz, $CDCl_3$) δ 148.7, 145.2, 134.5, 133.1, 131.6, 130.5, 120.8, 117.2, 62.3. GC-MS (EI) m/z 213 (M$^+$).

3-Chloro-5-ethyl-2-methoxyaniline (A6): A mixture of the A5 (3.17 g, 14.8 mmol) and 10% Pd/C (0.350 g) in Ethyl acetate (30 mL) was stirred under an atmosphere of hydrogen (45 psi) at room temperature for 45 minutes. The reaction mixture was filtered through a Celite pad and evaporated under vacuum. The reaction mixture was sufficiently pure to be used for the next step without further purification. $^1$H NMR (400 MHz, $CDCl_3$) 6.60 (d, J=2.0 Hz, 1H), 6.44 (d, J=2.0 Hz, 1H), 3.96 (bs, 2H), 3.83 (s, 3H), 2.48 (q, J=7.6 Hz, 2H), 1.19 (t, J=7.6 Hz, 3H); $^{13}$C NMR (100 MHz, $CDCl_3$) δ 141.3, 141.0, 140.9, 127.0, 118.3, 113.7, 59.4, 28.1, 15.2. GC-MS (EI) m/z 185 (M$^+$).

1-(3-Chloro-5-ethyl-2-methoxyphenyl)piperazine (A7): The reaction mixture of A6 (2.8 g, 15.13 mmol) and bis(2-chloroethyl)amine hydrochloride (2.69 g, 15.13 mmol) in diethylene glycol monomethyl ether (4.0 mL) was heated at 150° C. for 7 h under inert atmosphere. The reaction mixture was allowed to come to RT, crushed ice was added and the mixture was neutralized with 2M NaOH to pH 8-9, followed by extraction with ethyl acetate (250 mL). The organic layer was collected, washed twice with ice cold water, concentrated and purified by column chromatography using 5% MeOH/$CHCl_3$ as eluent to provide 2.7 g (70%) of solid product. $^1$H NMR (400 MHz, $CDCl_3$) δ 6.84 (d, J=2 Hz, 1H), 6.61 (d, J=2.4 Hz, 1H), 3.85 (s, 3H), 3.08-3.01 (m, 8H), 2.55 (q, J=8 Hz, 2H), 1.20 (t, J=7.6 Hz, 3H); $^{13}$C NMR (100 MHz, $CDCl_3$) δ 146.8, 146.6, 140.9, 128.4, 122.4, 116.9, 59.2, 51.9, 46.8, 28.6, 15.6. GC-MS (EI) m/z 254.2 (M$^+$). The oxalate salt was precipitated from acetone; Mp 190-191° C. Anal. $C_{13}H_{19}ClN_2O \cdot C_2H_2O_4 \cdot 0.5H_2O$) C, H, N.

4-amino-1-(4-(3-chloro-5-ethyl-2-methoxyphenyl)piperazin-1-yl)butan-2-ol (A9) 2-(2-(oxiran-2-yl)ethyl)isoindoline-1,3-dione A8 (0.768 g, 3.54 mmol) was added to the reaction mixture of A7 (0.90 g, 3.54 mmol) in 2-propanol (15 mL) and stirred at reflux for 3 h. The formation of 2-(4-(4-(3-chloro-5-ethyl-2-methoxyphenyl)piperazin-1-yl)-3-hydroxybutyl)isoindoline-1,3-dione was confirmed by thin layer chromatography (Kumar et al. J. Med. Chem., 2016, 59 (16), pp 7634-7650.) The reaction mixture was cooled to 20° C. and hydrazine was added and again the reaction mixture was heated to reflux at 90° for 7 h. The reaction was monitored by TLC and when the reaction was complete, the solvent was evaporated and basified with 20% $K_2CO_3$ solution (20 mL), followed by extraction with chloroform (250 mL). The combined organic layer was dried over anhydrous $Na_2SO_4$ and the solvent was evaporated to afford the product as an oil. $^1$H NMR (400 MHz, $CDCl_3$) δ 6.77 (d, J=2.0 Hz, 1H), 6.55 (d, J=1.6 Hz, 1H), 3.85-3.81 (m, 1H), 3.76 (s, 3H), 3.06 (bs, 4H), 2.86 (m, 2H), 2.72-2.70 (m, 2H), 2.53-2.44 (m, 4H), 2.37-2.28 (m, 3H), 1.53-1.44 (m, 2H), 1.13 (t, J=8.0 Hz, 3H); $^{13}$C NMR (100 MHz, $CDCl_3$) δ 146.3, 146.0, 140.7, 128.1, 122.2, 116.6, 66.2, 64.6, 58.9, 53.8, 50.3, 39.6, 37.7, 28.4, 15.4.

(S)-4-amino-1-(4-(3-chloro-5-ethyl-2-methoxyphenyl) piperazin-1-yl)butan-2-ol (A9S) was prepared by the method described for A9 using (S)-2-(2-(oxiran-2-yl)ethyl) isoindoline-1,3-dione (A8S); $^1$H NMR (400 MHz, $CDCl_3$) δ 6.99 (s, 1H), 6.88 (dd, J=19.1, 8.2 Hz, 2H), 6.61 (s, 1H), 3.97-3.76 (m, 4H), 3.14 (s, 4H), 2.91 (d, J=3.4 Hz, 6H), 2.79 (s, 3H), 2.55 (dt, J=14.5, 7.3 Hz, 6H), 2.47-2.32 (m, 4H), 1.67-1.46 (m, 4H), 1.20 (t, J=7.6 Hz, 4H).

(R)-4-amino-1-(4-(3-chloro-5-ethyl-2-methoxyphenyl) piperazin-1-yl)butan-2-ol(A9R) was prepared by the method described for A9 using (R)-2-(2-(oxiran-2-yl)ethyl)isoindoline-1,3-dione (A8R). The product obtained as such taken for the next step.

General Amidation Procedure A. The carboxylic acid (1.0 mmol) was dissolved in a solution of chloroform and dimethylformamide (8:2) and cooled to 0° C. To this solution was added 1-Ethyl-3-(3-dimethylaminopropyl)carbodiimide (EDCI) (1.3 mmol) and Hydroxybenzotriazole (Hobt) (1.2 mmol). (*Org Biomol Chem.* 2015; 13(40):10162-78). After 30 min, 1 eq of the aryl amine was added at 0° C. To this reaction mixture was added diisopropylethylamine (DIPEA) (1.5 mmol) and the reaction mixture continued stirring at room temperature for 8 h. The reaction progress was monitored by TLC. After completion saturated sodium bicarbonate ($NaHCO_3$) solution was added and the final compounds were extracted from chloroform (50 ml×4). The organic layer obtained was evaporated to afford the crude amide, which were purified using flash column chromatography to provide the desired pure product. All the enantiomers and racemic compounds were characterized by chiral HPLC.

N-(4-(4-(3-chloro-5-ethyl-2-methoxyphenyl)piperazin-1-yl)-3-hydroxybutyl)-1H-indole-2-carboxamide (±)-29 was prepared from indole-2-carboxylic acid and A9 according to the general amidation procedure A. The crude product was purified by flash chromatography using 30% acetone/$CHCl_3$ as eluent to give the desired product in 60.0% yield. $^1$H NMR (400 MHz, CDCl3) δ 9.21 (s, 1H), 7.64 (d, J=8.1 Hz, 1H), 7.42 (t, J=10.3 Hz, 2H), 7.37 (s, 1H), 7.27 (dd, J=11.1, 4.0 Hz, 1H), 7.13 (t, J=7.5 Hz, 1H), 6.85 (d, J=10.7 Hz, 1H), 6.62 (s, 1H), 4.10-3.87 (m, 2H), 3.84 (s, 3H), 3.57-3.39 (m, 1H), 3.16 (s, 3H), 2.84 (s, 2H), 2.55 (dd, J=15.1, 7.6 Hz, 3H), 2.48-2.37 (m, 2H), 1.94-1.74 (m, 1H), 1.72-1.52 (m, 3H), 1.21 (t, J=7.5 Hz, 3H). $^{13}$C NMR (101 MHz, CDCl3) δ 162.89, 162.02, 161.43, 146.41, 145.72, 140.79, 136.06, 131.10, 128.25, 127.76, 124.27, 122.44, 121.72, 120.54, 116.59, 111.86, 101.69, 66.42, 63.67, 58.99, 53.61, 50.30, 38.06, 33.24, 28.40, 15.31; The hydrochloride salt was precipitated from acetone; Anal ($C_{26}H_{33}ClN_4O_3 \cdot HCl.2H_2O$) C, H, N.

(S)—N-(4-(4-(3-chloro-5-ethyl-2-methoxyphenyl)piperazin-1-yl)-3-hydroxybutyl)-1H-indole-2-carboxamide ((S)-

29) was prepared from indole-2-carboxylic acid and A9S according to the general amidation procedure A. The crude product was purified by flash chromatography using 30% acetone/CHCl$_3$ as eluent to give the desired product in 55% yield. $^1$H NMR (400 MHz, CDCl3) δ 9.42 (s, 1H), 7.64 (d, J=8.0 Hz, 1H), 7.43 (t, J=6.9 Hz, 2H), 7.40 (s, 1H), 7.31-7.22 (m, 1H), 7.13 (t, J=7.5 Hz, 1H), 6.89-6.81 (m, 1H), 6.62 (d, J=1.5 Hz, 1H), 4.02-3.86 (m, 2H), 3.85 (d, J=10.7 Hz, 3H), 3.50 (ddd, J=13.1, 8.3, 3.9 Hz, 1H), 3.15 (s, 3H), 2.84 (d, J=5.3 Hz, 2H), 2.55 (dd, J=15.1, 7.6 Hz, 3H), 2.48-2.34 (m, 2H), 1.91-1.77 (m, 1H), 1.64 (dtd, J=13.8, 8.9, 4.6 Hz, 3H), 1.21 (t, J=7.6 Hz, 3H). $^{13}$C NMR (101 MHz, CDCl3) δ 161.47, 146.41, 145.76, 140.76, 136.16, 131.14, 128.16, 127.61, 124.18, 122.44, 121.84, 120.38, 116.67, 111.77, 101.69, 66.48, 63.74, 58.98, 53.68, 50.39, 37.96, 33.10, 28.46, 28.21, 15.42. The hydrochloride salt was precipitated from acetone; Anal (C$_{26}$H$_{33}$ClN$_4$O$_3$·HCl) C, H, N. [α]$^{23}_D$+ 34.54 (CHCl3, c 0.16) ee>98%. Mp 191-192° C. In an alternative procedure, (S)-29 was prepared using chiral preparative HPLC from its corresponding racemate achieving >99% ee.

Preparative HPLC Method C: CHIRALCEL OZ-H (Daicel Corporation CPI Company) semi preparative column (20×250 mm, 5 μm) performed on an Agilent Technologies HP series 1200 HPLC. The mobile phase used (10 mL/min flow rate) was composed of 10% 2-propanol in hexanes with isocratic resolution. The total run time was 50 min and DAD detector wavelength was set at 254 nm. A sample of 0.6 mL with a concentration of 10 mg/mL, was injected for preparative separation. Preparative HPLC Method D: CHIRALPAK AD-H (Daicel Corporation CPI Company) semi preparative column (21×250 mm, 5 μm). The mobile phase used (18 mL/min flow rate) was composed of 10% 2-propanol in hexanes with isocratic resolution. The total run time was 60 min and DAD detector wavelengths were set at 254 nm and 280 nm. A Sample of 5.0 ml with concentration of 10 mg/mL, was injected for preparative separation.

(R)—N-(4-(4-(3-chloro-5-ethyl-2-methoxyphenyl)piperazin-1-yl)-3-hydroxybutyl)-1H-indole-2-carboxamide ((R)-29) was prepared from indole-2-carboxylic acid and A9R according to the general amidation procedure A. The crude product was purified by flash chromatography using 30% acetone/CHCl$_3$ as eluent to give the desired product in 51% yield. $^1$H NMR (400 MHz, CDCl3) δ 9.33 (s, 1H), 7.64 (d, J=7.9 Hz, 1H), 7.43 (t, J=8.1 Hz, 1H), 7.40 (s, 1H), 7.32-7.22 (m, 1H), 7.13 (t, J=7.6 Hz, 1H), 6.85 (d, J=8.4 Hz, 1H), 6.62 (s, 1H), 3.91 (dd, J=13.1, 6.2 Hz, 2H), 3.84 (s, 3H), 3.58-3.41 (m, 1H), 3.16 (s, 3H), 2.85 (s, 2H), 2.56 (dd, J=15.1, 7.6 Hz, 3H), 2.45 (d, J=6.4 Hz, 2H), 1.82 (s, 1H), 1.64 (d, J=9.2 Hz, 3H), 1.21 (t, J=7.6 Hz, 3H); $^{13}$C NMR (101 MHz, CDCl3) δ 161.52, 146.26, 145.95, 140.77, 136.06, 131.15, 128.30, 127.72, 124.25, 122.33, 121.73, 120.52, 116.67, 111.87, 101.88, 66.43, 63.75, 59.09, 53.69, 50.39, 38.05, 33.26, 28.47; The hydrochloride salt was precipitated from acetone; Anal (C$_{26}$H$_{33}$ClN$_4$O$_3$·HCl·H$_2$O) C, H, N. [α]$^{23}_D$ −27.89 (CHCl3, c 0.23) ee>98%. It has been determined that the R-enantiomer is the eutomer. Mp 194-195° C. In an alternative procedure, (R)-29 was prepared using chiral preparative HPLC from its corresponding racemate achieving >99% ee.

2-Chloro-1-nitro-3-vinylbenzene (B4): The same procedure was used as described for A5, starting from B3 (Kumar et al. J. Med. Chem., 2016, 59 (16), pp 7634-7650) to give the desired product in 70% yield. $^1$H NMR (400 MHz, CDCl$_3$) 7.74 (dd, J=8.0, 1.6 Hz, 1H), 7.64 (dd, J=8.0, 1.6 Hz, 1H), 7.37 (t, J=8.0 Hz, 1H), 7.12 (dd, J=17.2, 11.0 Hz, 1H), 5.81 (dd, J=17.2, 0.8 Hz, 1H), 5.54 (dd, J=10.8, 0.8 Hz, 1H); $^{13}$C NMR (100 MHz, CDCl$_3$) δ 149.6, 138.9, 132.1, 129.9, 127.2, 124.8, 123.9, 119.6.

2-Chloro-3-ethylaniline (B5): The same procedure was used as described for A6 using B4 in EtOAc as the solvent. The product was sufficiently pure to be used for the next step without further purification. $^1$H NMR (400 MHz, CDCl$_3$) 6.99 (t, J=7.6 Hz, 1H), 6.66-6.62 (m, 2H), 4.04 (bs, 2H), 2.72 (q, J=7.6 Hz, 2H), 1.22 (t, J=7.6 Hz, 3H); $^{13}$C NMR (100 MHz, CDCl$_3$) δ 143.1, 142.4, 126.9, 119.2, 118.9, 113.4, 27.1, 13.9.

1-(2-Chloro-3-ethylphenyl)piperazine (B6): The same procedure was used as described for A7 starting with B5. The product was purified by flash chromatography using 2% MeOH/CHCl$_3$ as eluent to give the desired product in 46% yield. $^1$H NMR (400 MHz, CDCl$_3$) δ 7.16-7.12 (m, 1H), 6.94-6.89 (m, 2H), 3.05-2.95 (m, 8H), 2.76 (q, J=7.6 Hz, 2H), 1.21 (t, J=7.6 Hz, 3H); $^{13}$C NMR (100 MHz, CDCl$_3$) δ 150.0, 143.2, 128.7, 126.9, 123.9, 118.0, 53.0, 46.3, 27.5, 14.1. The oxalate salt was precipitated from acetone; Mp 166-167° C. Anal. (C$_{12}$H$_{17}$ClN$_2$·1.5C$_2$H$_2$O$_4$·H$_2$O) C, H, N.

4-Amino-1-(4-(2-chloro-3-ethylphenyl)piperazin-1-yl)butan-2-ol (B8): The same procedure was used as described for A9, employing B7 to afford B8 in 90% yield and was sufficiently pure to be used for the next step without further purification. $^1$H NMR (400 MHz, CDCl$_3$) 7.03-7.0 (m, 1H), 6.82-6.77 (m, 2H), 3.80-3.71 (m, 1H), 2.92-2.61 (m, 10H), 2.49-2.24 (m, 7H), 1.46-1.40 (m, 2H), 1.10 (t, J=7.6, 0.8 Hz, 3H); $^{13}$C NMR (100 MHz, CDCl$_3$) δ 149.2, 142.8, 128.3, 126.6, 123.6, 117.7, 65.8, 64.4, 51.3, 39.3, 37.5, 27.1, 13.8.

(S)-4-amino-1-(4-(2-chloro-3-ethylphenyl)piperazin-1-yl)butan-2-ol (B8S) was prepared by the method described for B8 using (S)-2-(2-(oxiran-2-yl)ethyl)isoindoline-1,3-dione B7S.

(R)-4-amino-1-(4-(2-chloro-3-ethylphenyl)piperazin-1-yl)butan-2-ol (B8R) was prepared by the method described for A9 using (R)-2-(2-(oxiran-2-yl)ethyl)isoindoline-1,3-dione B7R.

N-(4-(4-(2-chloro-3-ethylphenyl)piperazin-1-yl)-3-hydroxybutyl)-1H-indole-2-carboxamide (±)-19 was prepared from indole-2-carboxylic acid and B8 according to the general amidation procedure A. The crude product was purified by flash chromatography using 30% acetone/CHCl$_3$ as eluent to give the desired product in 60% yield. $^1$H NMR (400 MHz, CDCl3) δ 9.20 (s, 1H), 7.64 (d, J=7.8 Hz, 2H), 7.43 (d, J=8.2 Hz, 1H), 7.40 (s, 1H), 7.31-7.23 (m, 1H), 7.20-7.09 (m, 1H), 7.00-6.88 (m, 2H), 6.84 (d, J=1.4 Hz, 1H), 3.91 (ddd, J=13.5, 10.7, 5.2 Hz, 3H), 3.57-3.41 (m, 1H), 3.07 (s, 3H), 2.88 (d, J=5.4 Hz, 2H), 2.78 (q, J=7.5 Hz, 2H), 2.61 (s, 2H), 2.51-2.39 (m, 2H), 1.89-1.76 (m, 1H), 1.64 (ddd, J=18.9, 9.1, 4.4 Hz, 1H), 1.22 (q, J=7.5 Hz, 3H). $^{13}$C NMR (101 MHz, CDCl3) δ 161.36, 149.36, 143.15, 136.05, 131.04, 128.50, 127.81, 126.90, 124.19, 124.14, 121.76, 120.53, 117.96, 111.76, 101.73, 66.52, 63.62, 51.65, 51.34, 38.00, 33.11, 27.46, 27.32, 14.07. The hydrochloride salt was precipitated from acetone; Anal (C$_{25}$H$_{31}$ClN$_4$O$_2$·HCl·H$_2$O) C, H, N.

(R)—N-(4-(4-(2-chloro-3-ethylphenyl)piperazin-1-yl)-3-hydroxybutyl)-1H-indole-2-carboxamide (R)-19 was prepared from indole-2-carboxylic acid and 8R according to the general amidation procedure A. The crude product was purified by flash chromatography using 30% acetone/CHCl$_3$ as eluent to give the desired product in 50% yield. $^1$H NMR (400 MHz, CDCl$_3$) δ 9.44 (s, 1H), 7.64 (d, J=7.7 Hz, 2H), 7.44 (d, J=7.9 Hz, 1H), 7.33-7.21 (m, 1H), 7.15 (dt, J=14.9, 7.5 Hz, 1H), 6.95 (dd, J=17.8, 7.6 Hz, 2H), 6.85 (s, 2H), 4.01-3.82 (m, 3H), 3.51 (s, 1H), 3.07 (s, 3H), 2.89 (s, 2H), 2.78 (dd, J=14.8, 7.3 Hz, 2H), 2.63 (s, 2H), 2.52-2.40 (m, 2H), 1.83 (s, 1H), 1.64 (d, J=9.4 Hz, 1H), 1.23 (t, J=7.4 Hz, 3H). $^{13}$C NMR (101 MHz, CDCl3) δ 161.54, 149.26, 143.23, 136.18, 131.14, 128.72, 127.64, 126.78, 124.22, 121.70, 120.49, 117.97, 111.85, 101.83, 66.45, 63.70, 51.63, 38.09, 33.26, 27.46, 14.02. The hydrochloride salt was precipitated from acetone; Anal ($C_{25}H_{31}ClN_4O_2 \cdot HCl \cdot H_2O$) C, H, N. $[\alpha]^{23}{}_D$ −45.29 (CHCl3, c 0.23), ee>98%. Mp 233-234° C. In an alternative procedure, (R)-19 was prepared using chiral preparative HPLC from its corresponding racemate achieving >99% ee.

(S)—N-(4-(4-(2-chloro-3-ethylphenyl)piperazin-1-yl)-3-hydroxybutyl)-1H-indole-2-carboxamide (S)-19 was prepared from indole-2-carboxylic acid and B8S according to the general amidation procedure A. The crude product was purified by flash chromatography using 30% acetone/CHCl3 as eluent to give the desired product in 55% yield. $^1$H NMR (400 MHz, CDCl3) δ 9.52 (s, 1H), 7.64 (d, J=7.8 Hz, 1H), 7.45 (dd, J=8.3, 0.7 Hz, 2H), 7.33-7.21 (m, 1H), 7.14 (dt, J=7.9, 4.3 Hz, 1H), 6.95 (ddd, J=18.5, 7.8, 1.4 Hz, 2H), 6.86 (d, J=1.3 Hz, 2H), 4.07-3.82 (m, 3H), 3.51 (ddd, J=13.2, 8.4, 4.1 Hz, 1H), 3.07 (s, 3H), 2.89 (dd, J=10.6, 5.0 Hz, 2H), 2.78 (q, J=7.5 Hz, 2H), 2.62 (d, J=7.8 Hz, 2H), 2.51-2.38 (m, 2H), 1.84 (dd, J=13.5, 5.6, 3.3 Hz, 1H), 1.73-1.55 (m, 1H), 1.24 (dd, J=12.8, 5.3 Hz, 3H). $^{13}$C NMR (101 MHz, CDCl3) δ 161.56, 149.36, 143.16, 136.20, 131.02, 128.66, 127.76, 126.90, 124.20, 121.92, 120.48, 117.97, 111.92, 101.82, 66.40, 63.70, 51.64, 38.11, 33.17, 27.47, 14.08. The hydrochloride salt was precipitated from acetone; Anal ($C_{25}H_{31}ClN_4O_2 \cdot HCl \cdot H_2O$) C, H, N. $[\alpha]^{23}{}_L$ +48.13 (CHCl3, c 0.25) ee>98%. Mp 237-238° C. In an alternative procedure, (S)-19 was prepared using chiral preparative HPLC from its corresponding racemate achieving >99% ee.

2-(4-(4-(3-Chloro-5-ethyl-2-methoxyphenyl)piperazin-1-yl)butyl)isoindoline-1,3-dione (14a): N-(4-Bromobutyl) phthalimide (0.378 g, 1.34 mmol) was added to a reaction mixture of A7 (0.310 g, 1.22 mmol) and $K_2CO_3$ (0.505 g, 3.65 mmol) in acetone (15 mL) and stirred at reflux overnight. The crude product was filtered, concentrated and purified by flash chromatography using 12% EtOAc/hexanes as eluent to provide 0.465 g (83.6%) of the product as oil. $^1$H NMR (400 MHz, CDCl$_3$) δ 7.68 (dd, J=5.6, 2.8 Hz, 2H), 7.57 (dd, J=5.6, 3.2 Hz, 2H), 6.68 (d, J=2.4 Hz, 1H), 6.49 (d, J=2.0 Hz, 1H), 3.69 (s, 3H), 3.60 (t, J=7.0 Hz, 2H), 3.01 (bs, 4H), 2.48 (bs, 4H), 2.40 (q, J=7.6 Hz, 2H), 2.32 (t, J=7.0 Hz, 2H), 1.62 (quintet, J=7.6 Hz, 2H), 1.48-1.45 (m, 2H), 1.06 (t, J=7.6 Hz, 3H); $^{13}$C NMR (100 MHz, CDCl$_3$) δ 168.2, 146.3, 146.0, 140.6, 133.8, 132.0, 128.0, 123.0, 122.0, 116.6, 58.8, 57.9, 53.6, 50.0, 37.7, 28.3, 26.5, 23.9, 15.3.

2-(4-(4-(2-Chloro-3-ethylphenyl)piperazin-1-yl)butyl) isoindoline-1,3-dione (14b): The same procedure was used as described for 14a, employing B6. The product was purified by flash chromatography using 20% EtOAc/hexanes as eluent to afford 14b in 64.2% yield. $^1$H NMR (400 MHz, CDCl$_3$) 7.85-7.82 (m, 2H), 7.71-7.69 (m, 2H), 7.15 (dt, J=7.6, 2.4 Hz, 1H), 6.95-6.91 (m, 2H), 3.75 (dt, J=6.4, 0.8 Hz, 2H), 3.06 (bs, 4H), 2.77 (dq, J=7.6, 2.0 Hz, 2H), 2.64 (bs, 4H), 2.47 (t, J=6.8 Hz, 2H), 1.80-1.75 (m, 2H), 1.63-1.59 (m, 2H), 1.27-1.21 (m, 3H); $^{13}$C NMR (100 MHz, CDCl$_3$) δ 167.9, 149.4, 142.8, 133.6, 131.9, 128.4, 126.6, 123.6, 122.8, 117.7, 57.8, 53.2, 51.3, 37.6, 27.2, 26.4, 24.0, 13.9.

4-(4-(3-Chloro-5-ethyl-2-methoxyphenyl)piperazin-1-yl)butan-1-amine (16a): Hydrazine (0.097 g, 3.02 mmol) was added to a solution of compound 14a (0.460 g, 1.00 mmol) in EtOH (15 mL) and stirred at reflux for 7 h. The solvent was evaporated and the reaction mixture was diluted with 20% aq. $K_2CO_3$ solution (15 mL) and extracted in CHCl$_3$ (2×15 mL). The organic layer was combined, dried and concentrated to afford yellow oily product, which was sufficiently pure to be used for the next step without further purification. $^1$H NMR (400 MHz, CDCl$_3$) δ 6.70 (d, J=2.0 Hz, 1H), 6.49 (d, J=2.0 Hz, 1H), 3.70 (s, 3H), 3.01 (bs, 4H), 2.59 (s, 2H), 2.47-2.38 (m, 6H), 2.27 (t, J=7.6 Hz, 2H), 1.46-1.33 (m, 4H), 1.07 (t, J=7.6 Hz, 3H); $^{13}$C NMR (100 MHz, CDCl$_3$) δ 146.3, 146.1, 140.6, 128.0, 122.0, 116.5, 58.8, 58.5, 53.7, 50.2, 28.3, 24.2, 15.3.

4-(4-(2-Chloro-3-ethylphenyl)piperazin-1-yl)butan-1-amine (16b): The same procedure was used as described for 16a, employing 14b to afford 16b in 85.1% yield and was sufficiently pure to be used for the next step without further purification. $^1$H NMR (400 MHz, CDCl$_3$) 6.99-6.95 (m, 1H), 6.77-6.74 (m, 2H), 2.89 (bs, 4H), 2.63-2.54 (m, 4H), 2.47 (bs, 4H), 2.27-2.23 (m, 2H), 1.43-1.28 (m, 4H), 1.08-1.04 (m, 5H); $^{13}$C NMR (100 MHz, CDCl$_3$) δ 149.3, 142.7, 128.3, 126.5, 123.5, 117.6, 58.2, 53.1, 51.2, 41.8, 31.5, 27.1, 24.0, 13.8.

General Amidation Procedure B. CDI (1 equiv) was added to a solution of the carboxylic acid (1 equiv) in dry THF (10 mL/mmol) and stirred for 3 h at RT. The reaction mixture was cooled to 0° C. and particular amine (1 equiv) was added dropwise after diluting with dry THF (10 mL/mmol). The reaction mixture was allowed to come to RT and stirred overnight, concentrated, diluted with H$_2$O (20 mL) and extracted in CHCl$_3$ (3×10 mL). The organic layer was concentrated and the product was purified by flash column chromatography to provide the respective amide.

N-(4-(4-(2-Chloro-3-ethylphenyl)piperazin-1-yl)butyl)-1H-indole-2-carboxamide (18): 18 was prepared from indole-2-carboxylic acid and 16b according to the general amidation procedure B. The crude product was purified by flash chromatography using 30% acetone/CHCl$_3$ as eluent to give the desired product in 51.0% yield. $^1$H NMR (400 MHz, CDCl$_3$) 10.35 (s, 1H), 7.63 (d, J=7.6 Hz, 1H), 7.47 (d, J=8.8 Hz, 1H), 7.27 (dt, J=8.0, 1.2 Hz, 1H), 7.13 (sextet, J=4.0 Hz, 2H), 6.96-6.87 (m, 4H), 3.56 (dd, J=12.8, 6.4 Hz, 2H), 3.06 (bs, 4H), 2.78 (q, J=7.6 Hz, 2H), 2.65 (bs, 4H), 2.47 (t, J=7.2 Hz, 2H), 1.72-1.64 (m, 4H), 1.23 (t, J=7.6 Hz, 3H); $^{13}$C NMR (100 MHz, CDCl$_3$) δ 162.1, 149.6, 143.3, 136.7, 131.1, 128.7, 127.6, 127.0, 124.3, 124.1, 121.9, 120.6, 118.1, 112.2, 102.2, 58.1 53.5, 51.5, 39.8, 27.7, 27.6, 24.5, 14.2. The oxalate salt was precipitated from acetone; Mp 228-229° C. Anal ($C_{25}H_{31}ClN_4O \cdot C_2H_2O_4 \cdot 0.75H_2O$) C, H, N.

N-(4-(4-(2-Chloro-3-ethylphenyl)piperazin-1-yl)butyl) benzofuran-2-carboxamide (20): 20 was prepared from benzofuran-2-carboxylic acid and 16b according to the general amidation procedure B. The crude product was purified by flash chromatography using 25% EtOAc/hexanes as eluent to give the desired product in 76.5% yield. $^1$H NMR (400 MHz, CDCl$_3$) 7.65-7.63 (m, 1H), 7.46 (bs, 1H), 7.44 (d, J=0.8 Hz, 1H), 7.38 (dt, J=7.2, 1.2 Hz, 1H), 7.29-7.25 (m, 1H), 7.15-7.11 (m, 2H), 6.91 (dq, J=7.2, 1.6 Hz, 2H), 3.53 (dd, J=12.4, 6.4 Hz, 2H), 3.08 (bs, 4H), 2.77 (q, J=7.6 Hz, 2H), 2.67 (bs, 4H), 2.48 (t, J=7.0 Hz, 2H), 1.74-1.65 (m, 4H), 1.22 (t, J=7.6 Hz, 3H); $^{13}$C NMR (100 MHz, CDCl$_3$) δ 158.9, 154.7, 149.6, 149.0, 143.2, 128.7, 127.7, 126.9, 126.8, 124.0, 123.7, 122.7, 118.0, 111.7, 110.2, 58.0, 53.5, 51.5, 39.2, 27.6, 27.5, 24.4, 14.1. The oxalate salt was precipitated from acetone; Mp 119-120° C. Anal ($C_{25}H_{30}ClN_3O_2 \cdot C_2H_2O_4 \cdot 0.5H_2O$) C, H, N.

N-(4-(4-(2-Chloro-3-ethylphenyl)piperazin-1-yl)-3-hydroxybutyl)benzofuran-2-carboxamide (21): 21 was prepared from benzofuran-2-carboxylic acid and B8 according to the general amidation procedure B. The crude product was purified by flash chromatography using 25% acetone/CHCl$_3$ as eluent to give the desired product in 52.1% yield. $^1$H NMR (400 MHz, CDCl$_3$) 7.64 (d, J=7.2 Hz, 1H), 7.58 (t, J=5.0 Hz, 1H), 7.50-7.45 (m, 2H), 7.38 (dt, J=7.2, 1.2 Hz, 1H), 7.28-7.24 (m, 1H), 7.15 (t, J=7.6 Hz, 1H), 6.92 (dq, J=8.0, 1.2 Hz, 2H), 3.94-3.84 (m, 3H), 3.55-3.50 (m, 1H), 3.06 (bs, 4H), 2.87-2.85 (m, 2H), 2.76 (q, J=7.6 Hz, 2H), 2.62-2.61 (m, 2H), 2.48-02.43 (m, 2H), 1.85-1.80 (m, 1H), 1.66-1.63 (m, 1H), 1.22 (t, J=7.6 Hz, 3H); $^{13}$C NMR (100 MHz, CDCl$_3$) δ 159.0, 154.8, 149.4, 149.1, 143.3, 128.7, 127.7, 127.0, 126.7, 124.2, 123.6, 122.7, 118.0, 111.9, 110.1, 66.0, 63.9, 51.7, 37.5, 33.7, 27.5, 14.2. The oxalate salt was precipitated from ether; Mp 147-148° C. Anal (C$_{25}$H$_{30}$ClN$_3$O$_3$.C$_2$H$_2$O$_4$.H$_2$O) C, H, N.

N-(4-(4-(2-chloro-3-ethylphenyl)piperazin-1-yl)butyl) imidazo[1,2-a]pyridine-2-carboxamide (22): 22 was prepared from imidazo[1,2-a]pyridine-2-carboxylic acid and 16b according to the general amidation procedure B. The crude product was purified by flash chromatography using 3% MeOH/CHCl$_3$ as eluent to give the desired product in 78.4% yield. $^1$H NMR (400 MHz, CDCl$_3$) δ 8.11-8.09 (m, 2H), 7.53-7.49 (m, 2H), 7.21-7.17 (m, 1H), 7.10 (t, J=8.0 Hz, 1H), 6.89 (t, J=7.2 Hz, 2H), 6.81-6.77 (m, 1H), 3.48 (q, J=6.0 Hz, 2H), 3.03 (bs, 4H), 7.72 (q, J=7.6 Hz, 2H), 2.62 (m, 4H), 2.45-2.42 (m, 2H), 1.65 (m, 4H), 1.18 (t, J=7.6 Hz, 3H); $^{13}$C NMR (100 MHz, CDCl$_3$) δ 162.7, 149.6, 144.4, 143.1, 140.0, 128.6, 126.9, 126.5, 126.0, 123.9, 118.0, 114.1, 113.3, 58.1, 53.4, 51.4, 39.0, 27.7, 27.4, 24.3, 14.1. The oxalate salt was precipitated from acetone; Mp 144-145° C. Anal (C$_{24}$H$_{30}$ClN$_5$O.2C$_2$H$_2$O$_4$.1.5H$_2$O) C, H, N.

N-(4-(4-(2-Chloro-3-ethylphenyl)piperazin-1-yl)-3-hydroxybutyl)imidazo[1,2-a]pyridine-2-carboxamide (23): 23 was prepared from imidazo[1,2-a]pyridine-2-carboxylic acid and B8 according to the general amidation procedure B. The crude product was purified by flash chromatography using 2% MeOH/CHCl$_3$ as eluent to give the desired product in 46.3% yield. $^1$H NMR (400 MHz, CDCl$_3$) δ 8.13-8.11 (m, 2H), 7.90 (bt, J=6.0 Hz, 1H), 7.56 (dd, J=7.2, 0.8 Hz, 1H), 7.23-7.19 (m, 1H), 7.14 (t, J=8.0 Hz, 1H), 6.93 (dq, J=7.6, 1.6 Hz, 2H), 6.82 (dt, J=6.4, 1.2 Hz, 1H), 3.91-3.78 (m, 2H), 3.56-3.48 (m, 1H), 3.04 (bs, 4H), 2.86-2.83 (m, 2H), 2.75 (q, J=7.6 Hz, 2H), 2.62-2.60 (m, 2H), 2.45-2.40 (m, 2H), 1.84-1.76 (m, 1H), 1.70-1.61 (m, 1H), 1.21 (t, J=7.6 Hz, 3H); $^{13}$C NMR (100 MHz, CDCl$_3$) δ 162.9, 149.5, 144.6, 143.2, 140.2, 128.7, 126.9, 126.4, 125.8, 124.0, 118.2, 118.0, 114.1, 113.3, 65.3, 63.9, 53.5, 51.6, 36.6, 34.4, 27.4, 14.1. The oxalate salt was precipitated from acetone; Mp 137-138° C. Anal (C$_{24}$H$_{30}$ClN$_5$O$_2$·2C$_2$H$_2$O$_4$.H$_2$O.0.75CHCl$_3$) C, H, N.

N-(4-(4-(2-chloro-3-ethylphenyl)piperazin-1-yl)butyl)-6-methylimidazo[2,1-b]thiazole-5-carboxamide (24): 24 was prepared from 6-methylimidazo[2,1-b]thiazole-5-carboxylic acid and 16b according to the general amidation procedure B. The crude product was purified by flash chromatography using 3% MeOH/CHCl$_3$ as eluent to give the desired product in 48.9% yield. $^1$H NMR (400 MHz, CDCl$_3$) δ 8.19 (d, J=4.0 Hz, 1H), 7.13-7.09 (m, 1H), 6.92-6.82 (m, 3H), 5.98 (m, 1H), 3.50-3.45 (m, 2H), 3.03 (bs, 4H), 2.73 (q, J=7.6 Hz, 2H), 2.64 (bs, 4H), 2.58 (s, 3H), 2.48-2.45 (m, 2H), 1.66 (m, 4H), 1.19 (t, J=8.0 Hz, 3H); $^{13}$C NMR (100 MHz, CDCl$_3$) δ 160.7, 150.9, 149.4, 145.1, 143.2, 128.7, 126.9, 124.0, 121.4, 118.7, 117.9, 112.4, 58.1, 53.4, 51.3, 39.4, 27.9, 27.4, 24.2, 16.5, 14.1. The oxalate salt was precipitated from acetone; Mp 113-114° C. Anal (C$_{23}$H$_{30}$ClN$_5$OS.2C$_2$H$_2$O$_4$.2.5H$_2$O) C, H, N.

N-(4-(4-(2-Chloro-3-ethylphenyl)piperazin-1-yl)butyl)-4-ethyl-1H-imidazole-2-carboxamide (25): A solution of trimethylaluminium (2M in hexane) (0.18 mL, 3.54 mmol) was added dropwise to a solution of 16b (0.105 g, 3.54 mmol) in CH$_2$Cl$_2$ (10 mL) under argon at RT. The reaction mixture was stirred at RT for 15 min and ethyl 4-ethyl-1H-imidazole-2-carboxylate solution in CH$_2$Cl$_2$ (10 mL) was added dropwise and stirred for 6 h. The reaction mixture was quenched with dil. HCl solution (15 mL). The organic layer was extracted, dried over Na$_2$SO$_4$, concentrated and purified using flash chromatography with 4% MeOH/CHCl$_3$ as eluent to provide 0.148 g (14.9%) of product. $^1$H NMR (400 MHz, CDCl$_3$) δ 7.56 (bs, 1H), 7.13 (t, J=7.6 Hz, 1H), 6.92 (t, J=8.0 Hz, 2H), 6.82 (s, 1H), 3.46-3.43 (m, 2H), 3.06 (s, 4H), 2.75 (q, J=7.6 Hz, 2H), 2.66 (m, 5H), 2.48-2.46 (m, 2H), 2.18-2.15 (m, 1H), 1.65 (s, 5H), 1.29-1.18 (m, 6H); $^{13}$C NMR (100 MHz, CDCl$_3$) δ 159.1, 149.5, 143.2, 140.0, 128.7, 126.9, 124.0, 118.0, 58.0, 53.4, 51.2, 39.1, 27.5, 27.4, 24.1, 14.1, 13.5. The oxalate salt was precipitated from acetone; Mp 167-168° C. Anal (C$_{22}$H$_{32}$ClN$_5$O.2.5C$_2$H$_2$O$_4$.H$_2$O) C, H, N.

N-(4-(4-(2-Chloro-3-ethylphenyl)piperazin-1-yl)butyl)-4-methyl-1H-imidazole-2-carboxamide (26): 26 was prepared from 4-methyl-1H-imidazole-2-carboxylic acid and 16b according to the general amidation procedure B. The crude product was purified by flash chromatography using 3% MeOH/CHCl$_3$ as eluent to give the desired product in 65.2% yield. $^1$H NMR (400 MHz, CDCl$_3$) δ 7.76 (bs, 1H), 7.13 (t, J=8.0 Hz, 1H), 6.94-6.89 (m, 2H), 6.82 (s, 1H), 3.46 (q, J=6.4 Hz, 2H), 3.06 (bs, 4H), 2.75 (q, J=8.0 Hz, 2H), 2.64 (bs, 4H), 2.45 (t, J=7.2 Hz, 2H), 2.28 (s, 3H), 1.68-1.61 (m, 4H), 1.20 (t, J=7.6 Hz, 3H); $^{13}$C NMR (100 MHz, CDCl$_3$) δ 159.3, 149.5, 143.2, 140.1, 128.6, 126.9, 124.0, 118.0, 58.1, 53.4, 51.4, 39.2, 27.5, 24.2, 14.1. The oxalate salt was precipitated from acetone; Mp 175-176° C. Anal (C$_{21}$H$_{30}$ClN$_5$O.2C$_2$H$_2$O$_4$.H$_2$O) C, H, N.

N-(4-(4-(2-Chloro-3-ethylphenyl)piperazin-1-yl)-3-hydroxybutyl)-4-methyl-1H-imidazole-2-carboxamide (27): 27 was prepared from 4-methyl-1H-imidazole-2-carboxylic acid and B8 according to the general amidation procedure B. The crude product was purified by flash chromatography using 3% MeOH/CHCl$_3$ as eluent to give the desired product in 39.8% yield. $^1$H NMR (400 MHz, CDCl$_3$) δ 12.40 (bs, 1H), 8.11 (bs, 1H), 8.01 (s, 1H), 7.14 (t, J=8.0 Hz, 1H), 6.95-6.88 (m, 2H), 6.83 (bs, 1H), 3.90-3.84 (m, 1H), 3.79-3.70 (m, 1H), 3.57-3.49 (m, 1H), 3.03 (bs, 4H), 2.83-2.81 (m, 2H), 2.75 (q, J=8.0 Hz, 2H), 2.58 (bs, 2H), 2.42 (d, J=6.6 Hz, 2H), 2.29 (bs, 3H), 1.81-1.73 (m, 1H), 1.68-1.59 (m, 1H), 1.20 (t, J=8.0 Hz, 3H); $^{13}$C NMR (100 MHz, CDCl$_3$) δ 162.6, 159.3, 149.4, 143.2, 140.0, 128.6, 126.9, 124.1, 118.0, 65.0, 63.9, 53.5, 51.6, 36.8, 34.1, 27.5, 14.1. The oxalate salt was precipitated from acetone; Mp 130-131° C. Anal (C$_{21}$H$_{30}$ClN$_5$O$_2$.2C$_2$H$_2$O$_4$.3H$_2$O) C, H, N.

N-(4-(4-(3-Chloro-5-ethyl-2-methoxyphenyl)piperazin-1-yl)butyl)-1H-indole-2-carboxamide (28): 28 was prepared from indole-2-carboxylic acid and 16a according to the general amidation procedure B. The crude product was purified by flash chromatography using 25% acetone/CHCl$_3$ as eluent to give the desired product in 57.6% yield. $^1$H NMR (400 MHz, CDCl$_3$) δ 10.25 (s, 1H), 7.62 (d, J=8.0 Hz, 1H), 7.45 (dd, J=8.0, 0.8 Hz, 1H), 7.28-7.24 (m, 1H), 7.14-7.10 (m, 1H), 6.93 (m, 1H), 6.90 (s, 1H), 6.84 (d, J=1.6 Hz, 1H), 6.58 (d, J=1.6 Hz, 1H), 3.83 (s, 3H), 3.54 (q, J=6.0 Hz, 2H), 3.14 (bs, 4H), 2.60 (bs, 4H), 2.53 (q, J=7.6 Hz, 2H), 2.45 (t, J=7.0 Hz, 2H), 1.73-1.64 (m, 4H), 1.19 (t, J=7.6 Hz, 3H); $^{13}$C NMR (100 MHz, CDCl$_3$) δ 162.0, 146.4, 146.0, 140.9, 136.6, 131.0, 128.2, 127.6, 124.3, 122.3, 121.8, 120.5, 116.7, 112.1, 102.3, 59.0, 58.0, 53.7, 50.1, 39.6, 28.4, 27.5, 24.2, 15.4. The oxalate salt was precipitated from acetone and crystallized in MeOH/ether; Mp 220-221° C. Anal ($C_{26}H_{33}ClN_4O_2 \cdot C_2H_2O_4 \cdot 0.5H_2O$) C, H, N.

N-(4-(4-(3-Chloro-5-ethyl-2-methoxyphenyl)piperazin-1-yl)butyl)benzofuran-2-carboxamide (30): 30 was prepared from benzofuran-2-carboxylic acid and 16a according to the general amidation procedure. The crude product was purified by flash chromatography using 20% acetone/CHCl$_3$ as eluent to give the desired product in 76.5% yield. $^1$H NMR (400 MHz, CDCl$_3$) δ 7.63 (dd, J=7.2, 1.2 Hz, 1H), 7.44-7.42 (m, 2H), 7.36 (dt, J=7.0, 1.2 Hz, 1H), 7.28-7.24 (m, 1H), 7.13 (m, 1H), 6.82 (d, J=2.0 Hz, 1H), 6.59 (d, J=2.0 Hz, 1H), 3.82 (s, 3H), 3.51 (q, J=6.4 Hz, 2H), 3.15 (bs, 4H), 2.61 (bs, 4H), 2.51 (q, J=7.6 Hz, 2H), 2.45 (t, J=7.0 Hz, 2H), 1.73-1.63 (m, 4H), 1.17 (t, J=7.6 Hz, 3H); $^{13}$C NMR (100 MHz, CDCl$_3$) δ 158.9, 154.7, 149.0, 146.4, 146.1, 140.8, 128.2, 127.7, 126.7, 123.7, 122.7, 122.2, 116.7, 111.6, 110.2, 59.0, 58.0, 53.8, 50.2, 39.2, 28.4, 27.5, 24.3, 15.4. The oxalate salt was precipitated from acetone and crystallized in MeOH/ether; Mp 126-127° C. Anal ($C_{26}H_{32}ClN_3O_3 \cdot 2C_2H_2O_4 \cdot H_2O$) C, H, N.

N-(4-(4-(3-Chloro-5-ethyl-2-methoxyphenyl)piperazin-1-yl)-3-hydroxybutyl)benzofuran-2-carboxamide (31): 31 was prepared from benzofuran-2-carboxylic acid and A9 according to the general amidation procedure. The crude product was purified by flash chromatography using 20% acetone/CHCl$_3$ as eluent to give the desired product in 50.5% yield. $^1$H NMR (400 MHz, CDCl$_3$) δ 7.64 (dd, J=7.6, 0.8 Hz, 1H), 7.53 (m, 1H), 7.49 (dd, J=8.4. 0.8 Hz, 1H), 7.44 (d, J=0.8 Hz, 1H), 7.40-7.36 (m, 1H), 7.29-7.25 (m, 1H), 6.85 (d, J=2.0 Hz, 1H), 6.61 (d, J=2.0 Hz, 1H), 3.95-3.81 (m, 5H), 3.56-3.48 (m, 1H), 3.14 (bs, 4H), 2.84-2.81 (m, 2H), 2.62-2.51 (m, 4H), 2.46-2.42 (m, 2H), 1.87-1.80 (m, 1H), 1.68-1.61 (m, 1H), 1.20 (t, J=7.6 Hz, 3H); $^{13}$C NMR (100 MHz, CDCl$_3$) δ 159.0, 154.8, 149.0, 146.4, 146.0, 140.8, 128.3, 127.7, 126.7, 123.6, 122.6, 122.4, 116.7, 111.8, 110.1, 65.9, 63.8, 59.1, 53.7, 50.4, 37.3, 33.7, 28.5, 15.4. The oxalate salt was precipitated from acetone and crystallized in 2-PrOH/ether; Mp 154-155° C. Anal ($C_{26}H_{32}ClN_3O_4 \cdot 1.5C_2H_2O_4 \cdot H_2O$) C, H, N.

(E)-2-(4-(4-(2-Chloro-3-ethylphenyl)piperazin-1-yl)but-2-en-1-yl)isoindoline-1,3-dione (33): 32 (0.592 g, 2.11 mmol) was added to the reaction mixture of B6 (0.475 g, 2.11 mmol) and K$_2$CO$_3$ (0.1.458 g, 10.56 mmol) in acetone (25 ml) and stirred at reflux overnight. The reaction mixture was filtered, concentrated and purified using flash chromatography with 15% acetone/CHCl$_3$ as eluent to provide 0.880 g (98.2%) of product as an oil. $^1$H NMR (400 MHz, CDCl$_3$) δ 7.67 (dd, J=5.2, 3.2 Hz, 2H), 7.53 (dd, J=5.2, 3.2 Hz, 2H), 6.98 (t, J=8.0 Hz, 1H), 6.76 (t, J=6.4 Hz, 2H), 5.63 (d, J=4.4 Hz, 1H), 5.61 (d, J=4.4 Hz, 1H), 4.16 (d, J=4.0 Hz, 2H), 2.90 (m, 6H), 2.59 (q, J=8.0 Hz, 2H), 2.47 (bs, 4H), 1.06 (t, J=7.6 Hz, 3H); $^{13}$C NMR (100 MHz, CDCl$_3$) δ 167.6, 149.5, 142.9, 133.8, 132.0, 130.1, 128.5, 126.9, 126.8, 123.8, 123.1, 117.9, 60.1, 53.3, 51.4, 38.9, 27.4, 14.1.

(E)-4-(4-(2-Chloro-3-ethylphenyl)piperazin-1-yl)but-2-en-1-amine (34): The same procedure was used as described for 16a. The product was isolated in 91.2% yield and was sufficiently pure to be used for the next step without further purification. $^1$H NMR (400 MHz, CDCl$_3$) δ 6.96 (t, J=8.0 Hz, 1H), 6.75 (dd, J=8.0. 1.6 Hz, 2H), 5.63-5.57 (m, 1H), 5.53-5.46 (m, 1H), 3.13 (d, J=5.6 Hz, 2H), 2.88-2.87 (m, 6H), 2.59 (q, J=7.6 Hz, 2H), 2.47 (bs, 4H), 1.16 (bs, 2H), 1.05 (t, J=7.6 Hz, 3H); $^{13}$C NMR (100 MHz, CDCl$_3$) δ 149.5, 142.9, 135.3, 128.5, 126.8, 126.0, 123.8, 117.9, 60.4, 53.2, 51.4, 43.7, 27.4, 14.1. GC-MS (EI) m/z 293.1 (M$^+$).

(E)-N-(4-(4-(2-Chloro-3-ethylphenyl)piperazin-1-yl)but-2-en-1-yl)-4-methyl-1H-imidazole-2-carboxamide (35): 35 was prepared from 4-methyl-1H-imidazole-2-carboxylic acid and 34 according to the general amidation procedure. The crude product was purified by flash chromatography using 3% MeOH/CHCl$_3$ as eluent to give the desired product in 54.7% yield. $^1$H NMR (400 MHz, CDCl$_3$) δ 12.70-12.63 (m, 1H), 7.90 (bs, 1H), 7.13 (t, J=8.0 Hz, 1H), 6.94-6.89 (m, 2H), 6.80 (s, 1H), 5.76 (d, J=5.0, 1H), 5.73 (d, J=5.0, 1H), 4.06 (t, J=5.0, 2H), 3.05-3.04 (m, 6H), 2.75 (q, J=7.6, 2H), 2.62 (bs, 4H), 2.31 (s, 2H), 2.24 (s, 1H), 1.20 (t, J=8.0, 3H); $^{13}$C NMR (100 MHz, CDCl$_3$) δ 159.1, 149.5, 143.2, 139.9, 129.3, 129.2, 128.7, 126.9, 124.0, 118.0, 60.3, 53.4, 51.4, 40.8, 27.5, 14.1. The oxalate salt was precipitated from acetone and crystallized in MeOH/ether; Mp 166-167° C. Anal ($C_{21}H_{28}ClN_5O \cdot 2C_2H_2O_4 \cdot 1.25H_2O$) C, H, N.

1-(2-Chloro-3-ethylphenyl)-4-(2-(oxiran-2-yl)ethyl)piperazine (37): 2-(2-Bromoethyl)oxirane (0.269 g, 1.78 mmol) was added to a reaction mixture of B6 (0.266 g, 1.18 mmol) and K$_2$CO$_3$ (0.491 g, 3.56 mmol) in acetone (20 mL) and stirred at reflux overnight. The crude product was filtered, concentrated and purified by flash chromatography using 12% acetone/CHCl$_3$ as eluent to provide 0.145 g (41.4%) of the product as oil. $^1$H NMR (400 MHz, CDCl$_3$) δ 7.15 (t, J=7.6 Hz, 1H), 6.95-6.91 (m, 2H), 3.06 (bs, 4H), 3.02-2.95 (m, 1H), 2.80-2.73 (m, 3H), 2.66 (bs, 4H), 2.62-2.55 (m, 2H), 2.53-2.51 (m, 1H), 1.87-1.79 (m, 1H), 1.76-1.67 (m, 1H), 1.22 (t, J=7.6 Hz, 3H); $^{13}$C NMR (100 MHz, CDCl$_3$) δ 149.6, 143.2, 128.7, 126.9, 124.0, 118.0, 55.0, 53.5, 51.6, 50.9, 47.1, 30.2, 27.5, 14.2. GC-MS (EI) m/z 294.1 (M$^+$).

1-Azido-4-(4-(2-chloro-3-ethylphenyl)piperazin-1-yl)butan-2-ol (38): A reaction mixture of 37 (0.170 g, 0.57 mmol), NaN$_3$ (0.056 g, 0.86 mmol) and NH$_4$Cl (0.062 g, 1.15 mmol) in DMF (5 mL) was heated at 100° C. for 6 h. The solvent was evaporated and the reaction mixture was diluted with water (15 mL) and extracted in EtOAc (3×15 mL). The organic layer was combined, dried, concentrated and purified by flash chromatography using 7% acetone/CHCl$_3$ as eluent to provide 0.103 g (52.9%) of the product as an oil. $^1$H NMR (400 MHz, CDCl$_3$) δ 7.17 (t, J=7.6 Hz, 1H), 6.97 (dd, J=7.6, 1.2 Hz, 1H), 6.91 (dd, J=7.6, 1.2 Hz, 1H), 4.07-4.02 ((m, 1H), 3.28 (m, 2H), 3.07 (bs, 4H), 2.85-2.71 (m, 6H), 2.64-2.61 (m, 2H), 1.87-1.77 (m, 1H), 1.60-1.54 (m, 1H), 1.26-1.22 (m, 3H); $^{13}$C NMR (100 MHz, CDCl$_3$) δ 149.2, 143.3, 128.7, 127.0, 124.3, 118.1, 73.0, 57.3, 56.6, 53.4, 51.5, 28.5, 27.5, 14.1.

1-Amino-4-(4-(2-chloro-3-ethylphenyl)piperazin-1-yl)butan-2-ol (39): A mixture of 38 (0.123 g, 0.36 mmol) and 10% Pd/C (0.050 g) in EtOAc (10 mL) was stirred under an atmosphere of hydrogen (50 psi) at room temperature for 2 h. The reaction mixture was filtered through a Celite pad and evaporated under vacuum. The reaction mixture was sufficiently pure to be used for the next step without further purification. $^1$H NMR (400 MHz, CD$_3$OD+CDCl$_3$) δ 7.07 (t, J=7.6 Hz, 1H), 6.89 (dd, J=13.6, 8.4 Hz, 2H), 4.89 (bs, 2H), 4.11 (bs, 1H), 3.33-3.17 (m, 10H), 3.04-2.99 (m, 1H), 2.64 (q, J=7.2 Hz, 2H), 2.06-1.97 (m, 2H), 1.12 (t, J=7.6 Hz, 3H); $^{13}$C NMR (100 MHz, CDCl$_3$) δ 147.5, 143.3, 128.5, 127.1, 125.1, 118.3, 65.5, 54.2, 52.7, 48.7, 44.8, 28.8, 27.2, 13.8.

N-(4-(4-(2-Chloro-3-ethylphenyl)piperazin-1-yl)-2-hydroxybutyl)-1H-indole-2-carboxamide (40): 40 was prepared from indole-2-carboxylic acid and 39 according to the general amidation procedure B using DMF as solvent. The crude product was purified by flash chromatography using 2% MeOH/CHCl$_3$ as eluent to give the desired product in 16.4% yield.

¹H NMR (400 MHz, CDCl₃) δ 9.73 (s, 1H), 7.63 (d, J=7.6 Hz, 1H), 7.43 (dd, J=8.4, 0.8 Hz, 1H), 7.28-7.23 (m, 1H), 7.16-7.09 (m, 2H), 6.95 (dd, J=7.6, 1.2 Hz, 2H), 6.91 (d, J=1.2 Hz, 1H), 6.86 (dd, J=7.6, 1.6 Hz, 1H), 4.10-4.06 (m, 1H), 3.76-3.71 (m, 1H), 3.43-3.37 (m, 1H), 3.04 (bs, 4H), 2.93-2.81 (m, 2H), 2.79-2.69 (m, 4H), 2.62 (m, 2H), 1.82-1.78 (m, 1H), 1.62-1.57 (m, 1H), 1.21 (t, J=7.6 Hz, 3H); ¹³C NMR (100 MHz, CDCl₃) δ 161.9, 149.1, 143.3, 136.3, 130.8, 128.7, 127.7, 126.9, 124.3, 124.3, 121.9, 120.5, 118.0, 112.0 102.3, 72.6, 57.3, 53.4, 51.4, 45.3, 30.9, 28.6, 27.4, 14.0. The oxalate salt was precipitated from acetone; Mp 225-226° C. Anal ($C_{25}H_{31}ClN_4O_2 \cdot 1.5C_2H_2O_4 \cdot 1.75H_2O$) C, H, N.

2-(4-(4-(3-chloro-5-ethyl-2-methoxyphenyl)piperazin-1-yl)-3-hydroxybutyl)isoindoline-1,3-dione (C1a). A mixture of compounds A7 (1 mmol) and 2-(2-(oxiran-2-yl)ethyl) isoindoline-1,3-dione (A8, 1 mmol) was stirred at reflux in 2-PrOH (20 mL) for 3 h. The reaction mixture was concentrated and purified by flash chromatography using 20% EtOAc/hexanes as eluent to provide 0.523 g (91%) of product. ¹H NMR (400 MHz, CDCl₃) δ 7.85 (dd, J=5.2, 3.2 Hz, 2H), 7.71 (dd, J=5.6, 2.8 Hz, 2H), 6.84 (d, J=2.0 Hz, 1H), 6.60 (d, J=2.0 Hz, 1H), 3.93-3.79 (m, 6H), 3.13 (bs, 4H), 2.81-2.79 (m, 2H), 2.60-2.58 (m, 2H), 2.55 (q, J=8.0 Hz, 2H), 2.45-2.41 (m, 2H), 1.79 (q, J=7.2 Hz, 2H), 1.19 (t, J=8.0 Hz, 3H); ¹³C NMR (100 MHz, CDCl₃) δ 168.5, 146.4, 145.9, 140.8, 133.9, 132.2, 128.2, 123.2, 122.4, 116.7, 64.5, 63.9, 59.1, 53.8, 50.3, 35.1, 33.6, 28.4, 15.4.

(R)-2-(4-(4-(3-Chloro-5-ethyl-2-methoxyphenyl)piperazin-1-yl)-3-hydroxybutyl)isoindoline-1,3-dione ((R)-C1a). (R)-2-(2-(oxiran-2-yl)ethyl)isoindoline-1,3-dione, A8R (0.66 g, 3.04 mmol) was added to a solution of A7 (0.61 g, 2.43 mmol) in 2-propanol (15 mL) and stirred at reflux for 3 h. The crude product was purified by flash chromatography using 35% EtOAc in hexanes as eluent to give the desired product as a brown oil in 70% yield. ¹H NMR (400 MHz, CDCl₃) δ 7.85 (br s, 2H), 7.72 (br s, 2H), 6.84 (s, 1H), 6.60 (s, 1H), 3.97-3.68 (m and s, 3H and 3H), 3.11 (br s, 4H), 2.78 (m, 2H), 2.67-2.50 (m, 4H), 2.49-2.27 (m, 2H), 1.79 (d, J=6.5 Hz, 2H), 1.60 (br s, 1H), 1.20 (t, J=6.8 Hz, 3H).

(S)-2-(4-(4-(3-Chloro-5-ethyl-2-methoxyphenyl)piperazin-1-yl)-3-hydroxybutyl)isoindoline-1,3-dione ((S)-C1a). (S)-2-(2-(oxiran-2-yl)ethyl)isoindoline-1,3-dione, A8S (0.79 g, 3.13 mmol) was added to a mixture of A7 (0.84 g, 3.91 mmol) in 2-propanol (15 mL) and stirred at reflux for 3 h. The crude product was purified by flash chromatography using 40% EtOAc in hexanes as eluent to give the desired product as brown oil in 65% yield. ¹H NMR (400 MHz, CDCl₃) δ 7.85 (d, J=3.2 Hz, 2H), 7.71 (d, J=2.5 Hz, 2H), 6.84 (s, 1H), 6.60 (s, 1H), 3.90 (m, 2H), 3.82 (s, 3H), 3.77 (m, 1H), 3.11 (br s, 4H), 2.78 (m, 2H), 2.54 (m, 4H), 2.47-2.30 (m, 2H), 1.79 (m, 2H), 1.60 (br s, 1H), 1.20 (t, J=7.6 Hz, 3H).

2-(4-(4-(2-Chloro-3-ethylphenyl)piperazin-1-yl)-3-hydroxybutyl)isoindoline-1,3-dione (C1b): The same procedure was used as described for C1a, employing B6 (1 mmol) and 2-(2-(oxiran-2-yl)ethyl)isoindoline-1,3-dione (B7, 1 mmol). The product was purified by flash chromatography using 30% EtOAc/hexanes as eluent to afford C₁b in 57% yield. ¹H NMR (400 MHz, CDCl₃) 7.85 (dd, J=7.2, 5.6 Hz, 2H), 7.71 (dd, J=5.6, 3.2 Hz, 2H), 7.15 (t, J=8.0 Hz, 1H), 6.92 (dq, J=7.6, 1.6 Hz, 2H), 3.94-3.77 (m, 4H), 3.03 (bs, 4H), 2.84-2.81 (m, 2H), 2.76 (q, J=7.6 Hz, 2H), 2.59 (m, 2H), 2.46-2.38 (m, 2H), 1.79 (q, J=7.0, 2H), 1.22 (t, J=7.6 Hz, 3H); ¹³C NMR (100 MHz, CDCl₃) δ 168.7, 151.7, 149.6, 143.4, 134.0, 132.4, 128.8, 127.0, 124.2, 123.4, 118.1, 64.6, 64.0, 51.8, 35.3, 33.8, 27.6, 14.2.

(R)-2-(4-(4-(2-Chloro-3-ethylphenyl)piperazin-1-yl)-3-hydroxybutyl)isoindoline-1,3-dione ((R)-C1b). The compound was prepared starting from B6 (0.70 g, 3.22 mmol) following the same procedure described for ((R)-C1a). The crude product was purified by flash chromatography using 40% EtOAc in hexanes as eluent to give the desired product as brown oil in 75% yield. ¹H NMR (400 MHz, CDCl₃) δ 7.85 (br s, 2H), 7.72 (br s, 2H), 7.15 (t, J=7.3 Hz, 1H), 6.93 (dd, J=17.7, 7.6 Hz, 2H), 4.00-3.70 (m, 3H), 3.03 (br s, 4H), 2.91-2.69 (m, 4H), 2.59 (br s, 2H), 2.51-2.30 (m, 2H), 1.79 (m, 2H), 1.60 (br s, 1H) 1.22 (t, J=7.1 Hz, 3H).

(S)-2-(4-(4-(2-Chloro-3-ethylphenyl)piperazin-1-yl)-3-hydroxybutyl)isoindoline-1,3-dione ((S)-C1b). The compound was prepared starting from A8S (0.90 g, 4.14 mmol) and B6 (0.74 g, 3.31 mmol) following the same procedure described for ((S)-C1a). The product was purified by flash column chromatography using 40% EtOAc in hexanes, as the eluent, to give the desired product in 85% yield, as pale-yellow solid. ¹H NMR (400 MHz, CDCl₃) δ 7.92-7.79 (m, 2H), 7.77-7.65 (m, 2H), 7.15 (t, J=7.5 Hz, 1H), 6.92 (dd, J=17.9, 7.6 Hz, 2H), 4.03-3.82 (m, 2H), 3.78 (m, 1H), 3.03 (br s, 4H), 2.89-2.67 (m, 4H), 2.59 (m, 2H), 2.50-2.30 (m, 2H), 1.79 (q, J=6.5 Hz, 2H), 1.60 (br s, 1H), 1.23 (t, J=7.8 Hz, 3H).

2-(4-(4-(3-chloro-5-ethyl-2-methoxyphenyl)piperazin-1-yl)-3-fluorobutyl)isoindoline-1,3-dione (C2a): To compound C1a (1 mmol) was added dry dichloromethane and the reaction mixture was cooled to −78 C. Maintaining the same temperature, (Diethylamino)sulfur trifluoride (DAST, 1.5 mmol) dissolved in dry dichloromethane was added drop wise and the stirring continued at 20° C. for 8 h. Thin layer chromatography was used to monitor the progress of the reaction. Once the reaction was complete, ice cold water was added to the reaction mixture and the product was extracted in ethylacetate and purified by flash column using 20% ethylacetate and hexane, as the eluent. 1H NMR (400 MHz, cdcl3) δ 7.95-7.80 (m, 2H), 7.79-7.62 (m, 2H), 6.82 (t, J=10.6 Hz, 1H), 6.57 (t, J=16.3 Hz, 1H), 4.92-4.66 (m, 1H), 3.97-3.83 (m, 2H), 3.83-3.74 (m, 3H), 3.64-3.41 (m, 2H), 3.11 (d, J=3.0 Hz, 4H), 2.80-2.59 (m, 4H), 2.54 (td, J=7.5, 4.4 Hz, 2H), 2.18-1.78 (m, 2H), 1.20 (dt, J=12.1, 5.0 Hz, 3H).

(R)-2-(4-(4-(3-Chloro-5-ethyl-2-methoxyphenyl)piperazin-1-yl)-3-fluorobutyl)isoindoline-1,3-dione ((R)-C2a). The compound was prepared starting from (R)-C1a (5.83 g, 1.238 mmol) following the same procedure described for C2a. The product was purified by flash column chromatography using 30% EtOAc in hexanes, as the eluent, to give the desired product in 85% yield, as pale-yellow solid. ¹H NMR (400 MHz, CDCl₃) was identical to the one described for C2a.

(S)-2-(4-(4-(3-Chloro-5-ethyl-2-methoxyphenyl)piperazin-1-yl)-3-fluorobutyl)isoindoline-1,3-dione ((S)-C2a). The compound was prepared starting from (S)-C1a (0.44 g, 0.93 mmol) following the same procedure described for C2a. The product was purified by flash column chromatography using 40% EtOAc in hexanes, as the eluent, to give the desired product in 70% yield, as pale-yellow solid. ¹H NMR (400 MHz, CDCl₃) was identical to the one described for C2a.

2-(4-(4-(2-chloro-3-ethylphenyl)piperazin-1-yl)-3-fluorobutyl)isoindoline-1,3-dione (C2b) was prepared with C2b according to the procedure described for C2a. ¹H NMR (400 MHz, CDCl3) δ 7.90-7.80 (m, 2H), 7.77-7.66 (m, 2H), 7.14 (t, J=7.8 Hz, 2H), 6.92 (ddd, J=14.9, 7.8, 1.5 Hz, 1H), 4.94-4.65 (m, 1H), 4.12 (q, J=7.2 Hz, 2H), 3.95-3.76 (m, 2H), 3.04 (s, 2H), 2.74 (ddd, J=13.8, 12.9, 7.4 Hz, 2H), 2.64-2.44 (m, 2H), 2.20-1.92 (m, 4H), 1.58 (s, 2H), 1.24 (dt, J=16.2, 7.3 Hz, 3H).

(R)-2-(4-(4-(2-Chloro-3-ethylphenyl)piperazin-1-yl)-3-fluorobutyl)isoindoline-1,3-dione ((R)-C2b). The compound was prepared starting from (R)-C1b (0.65 g, 1.47 mmol) following the same procedure described for C2a. The product was purified by flash column chromatography using 30% EtOAc in hexanes, as the eluent, to give the desired product as a pale-yellow solid in 62% yield. $^1$H NMR (400 MHz, CDCl$_3$) was identical to the one described for C2b.

(S)-2-(4-(4-(2-Chloro-3-ethylphenyl)piperazin-1-yl)-3-fluorobutyl)isoindoline-1,3-dione ((S)-C2b). The compound was prepared starting from (S)-C1b (1.42 g, 3.20 mmol) following the same procedure described for C2a. The product was purified by flash column chromatography using 40% EtOAc in hexanes, as the eluent, to give the desired product as a pale-yellow solid in 80% yield. $^1$H NMR (400 MHz, CDCl$_3$) was identical to the one described for C2b.

4-(4-(3-chloro-5-ethyl-2-methoxyphenyl)piperazin-1-yl)-3-fluorobutan-1-amine (C3a) Hydrazine (3 mmol) was added to a solution of compound C2a (1 mmol) in EtOH (15 mL) and stirred at reflux for 7 h. The solvent was evaporated and the reaction mixture was diluted with 20% aq. K$_2$CO$_3$ solution (15 mL) and extracted in CHCl$_3$ (2×15 mL). The organic layer was combined, dried and concentrated to afford a yellow oily product, which was sufficiently pure to be used for the next step without further purification. 1H NMR (400 MHz, CDCl$_3$) δ 6.85 (d, J=1.8 Hz, 1H), 6.61 (d, J=2.0 Hz, 1H), 4.86 (d, J=49.8 Hz, 1H), 3.83 (d, J=6.6 Hz, 3H), 3.15 (s, 2H), 2.89 (d, J=6.3 Hz, 2H), 2.72 (dt, J=19.2, 10.6 Hz, 2H), 2.59-2.48 (m, 2H), 1.56 (s, 10H), 1.20 (t, J=7.6 Hz, 3H).

(R)-4-(4-(3-Chloro-5-ethyl-2-methoxyphenyl)piperazin-1-yl)-3-fluorobutan-1-amine ((R)-C3a). The compound was prepared starting from (R)-C3a (0.60 g, 1.26 mmol) following the same procedure described for C3a. The crude product was used in the next step without further purification.

(S)-4-(4-(3-Chloro-5-ethyl-2-methoxyphenyl)piperazin-1-yl)-3-fluorobutan-1-amine ((S)-C3a). The compound was prepared starting from (S)-C2a (0.345 g, 0.72 mmol) following the same procedure described for C3a. The crude product was used in the next step without further purification.

4-(4-(2-chloro-3-ethylphenyl)piperazin-1-yl)-3-fluorobutan-1-amine (C3b) was prepared with C2b using the procedure described for C3a. $^1$H NMR (400 MHz, CDCl3) δ 7.15 (t, J=7.8 Hz, 1H), 6.95 (dd, J=19.8, 11.6 Hz, 2H), 4.92 (d, J=49.8 Hz, 1H), 3.07 (s, 2H), 2.89 (dd, J=13.0, 6.2 Hz, 2H), 2.81-2.67 (m, 2H), 2.17 (s, 4H), 1.54 (s, 8H), 1.22 (t, J=7.5 Hz, 3H).

(R)-4-(4-(2-Chloro-3-ethylphenyl)piperazin-1-yl)-3-fluorobutan-1-amine ((R)-C3b). The compound was prepared starting from (R)-C3b (0.67 g, 1.51 mmol) following the same procedure described for C3a. The crude product was used in the next step without further purification.

(S)-4-(4-(2-Chloro-3-ethylphenyl)piperazin-1-yl)-3-fluorobutan-1-amine ((S)-C3b). The compound was prepared starting from (S)-C3b (1.27 g, 2.86 mmol) following the same procedure described for C3a. The crude product was used in the next step without further purification.

N-(4-(4-(3-chloro-5-ethyl-2-methoxyphenyl)piperazin-1-yl)-3-fluorobutyl)-1H-indole-2-carboxamide (C4a) was prepared from indole-2-carboxylic acid and C3a according to the general amidation procedure A. The crude product was purified by flash chromatography using 30% acetone/CHCl$_3$ as eluent to give the desired product in 50% yield. 1H NMR (400 MHz, CDCl3) δ 9.16 (s, 1H), 8.02 (s, 1H), 7.66 (t, J=8.7 Hz, 1H), 7.44 (d, J=8.3 Hz, 1H), 7.34-7.22 (m, 1H), 7.15 (dd, J=13.2, 6.1 Hz, 1H), 6.84 (dd, J=7.6, 1.7 Hz, 1H), 6.60 (d, J=2.0 Hz, 1H), 6.55 (s, 1H), 4.90 (d, J=49.1 Hz, 1H), 3.83 (s, 2H), 3.79-3.58 (m, 1H), 3.15 (s, 2H), 2.95 (s, 1H), 2.92-2.84 (m, 2H), 2.75-2.64 (m, 3H), 2.56 (dt, J=15.2, 5.6 Hz, 2H), 2.02 (dd, J=17.8, 14.3 Hz, 2H), 1.59 (s, 2H), 1.20 (t, J=7.6 Hz, 3H). The oxalate salt was precipitated from acetone; Anal (C$_{26}$H$_{32}$ClFN$_4$O$_2$.1.2C$_2$H$_2$O$_4$.H$_2$O) C, H, N. Mp 198-199° C.

(R)—N-(4-(4-(3-Chloro-5-ethyl-2-methoxyphenyl)piperazin-1-yl)-3-fluorobutyl)-1H-indole-2-carboxamide ((R)-C4a). The compound was prepared from indole-2-carboxylic acid (0.14 g, 0.90 mmol) and (R)-C3a (0.26 g, 0.75 mmol) according to the general amidation procedure C. The crude product was purified by flash chromatography using 35% acetone/CHCl$_3$ as eluent to give the desired product as pale-yellow solid (0.235 g, 64.0% yield). $^1$H NMR (400 MHz, CDCl$_3$), $^{13}$C NMR (101 MHz, CDCl$_3$) and $^{19}$F NMR (376 MHz, CDCl$_3$/CFCl$_3$) were identical to the ones described for C4a. The oxalate salt was precipitated from acetone; Mp 202-203° C. Anal (C$_{26}$H$_{32}$ClFN$_4$O$_2$.C$_2$H$_2$O$_4$.0.5H$_2$O) C, H, N. [α]$_D^{23}$+11.69 (CHCl$_3$, c 1.0), (R)-C4a was analyzed by HPLC Method B, retention time=62.022 min and enantiomeric excess was >99%.

(S)—N-(4-(4-(3-Chloro-5-ethyl-2-methoxyphenyl)piperazin-1-yl)-3-fluorobutyl)-1H-indole-2-carboxamide ((S)-C4a). The compound was prepared from indole-2-carboxylic acid (0.29 g, 1.82 mmol) and (S)-C3a (0.57 g, 1.65 mmol) according to the general amidation procedure. The crude product was purified by flash chromatography using 30% acetone/CHCl$_3$ as eluent to give the desired product (0.54 g, 66% yield). $^1$H NMR (400 MHz, CDCl$_3$), $^{13}$C NMR (101 MHz, CDCl$_3$) and $^{19}$F NMR (376 MHz, CDCl$_3$/CFCl$_3$) were identical to the ones described for C4a. The oxalate salt was precipitated from acetone; Mp 202-203° C.; Anal (C$_{26}$H$_{32}$ClFN$_4$O$_2$.C$_2$H$_2$O$_4$.H$_2$O) C, H, N. [α]$_D^{23}$ −9.69 (MeOH, c 1.0), (S)-C4a was analyzed by HPLC Method B, retention time=60.353 min and enantiomeric excess was >99%.

N-(4-(4-(3-chloro-5-ethyl-2-methoxyphenyl)piperazin-1-yl)-3-fluorobutyl)benzofuran-2-carboxamide (C4b) was prepared from benzofuran-2-carboxylic acid and C3a according to the general amidation procedure A. The crude product was purified by flash chromatography using 30% acetone/CHCl$_3$ as eluent to give the desired product in 55% yield. 1H NMR (400 MHz, CDCl3) δ 8.02 (s, 1H), 7.72-7.64 (m, 1H), 7.51-7.44 (m, 1H), 7.44-7.36 (m, 1H), 7.33-7.26 (m, 1H), 7.01 (d, J=12.0 Hz, 1H), 6.85 (d, J=2.0 Hz, 1H), 6.61 (d, J=2.0 Hz, 1H), 4.89 (d, J=49.9 Hz, 1H), 3.84 (s, 3H), 3.74-3.61 (m, 2H), 3.16 (s, 4H), 2.95 (s, 1H), 2.88 (d, J=0.5 Hz, 1H), 2.79-2.64 (m, 5H), 2.59-2.48 (m, 2H), 2.24-1.97 (m, 2H), 1.59 (s, 4H), 1.19 (t, J=7.6 Hz, 3H). $^{13}$C NMR (101 MHz, CDCl3) δ 159.00, 154.65, 148.55, 146.26, 146.01, 140.71, 128.23, 127.61, 126.79, 123.60, 122.72, 122.33, 116.60, 111.69, 110.41, 106.50, 92.03, 90.30, 61.99, 59.24, 54.36, 50.18, 35.88, 33.14, 28.53, 15.39. $^{19}$F NMR (376 MHz, CDCl$_3$/CFCl$_3$) δ −182.153 to −182.403 (m, 1F). The oxalate salt was precipitated from acetone; Anal (C$_{26}$H$_{31}$ClFN$_3$O$_3$.1.1C$_2$H$_2$O$_4$.H$_2$O) C, H, N. Mp 179-180° C.

N-(4-(4-(2-chloro-3-ethylphenyl)piperazin-1-yl)-3-fluorobutyl)-1H-indole-2-carboxamide (ABS01-113 (C5a) was prepared from indole-2-carboxylic acid and C3b according to the general amidation procedure A. The crude product was purified by flash chromatography using 30% acetone/

CHCl$_3$ as eluent to give the desired product in 60% yield. 1H NMR (400 MHz, CDCl3) δ 9.11 (s, 1H), 7.86 (s, 1H), 7.49 (s, 1H), 7.28 (s, 1H), 7.19-7.06 (m, 1H), 7.06-6.93 (m, 1H), 6.85-6.73 (m, 2H), 6.68 (s, 1H), 6.48 (s, 1H), 4.76 (d, J=48.0 Hz, 1H), 3.53 (d, J=25.1 Hz, 2H), 2.92 (s, 1H), 2.80 (ddd, J=6.7, 3.6, 1.8 Hz, 3H), 2.73 (ddd, J=5.1, 3.6, 1.8 Hz, 3H), 2.67-2.54 (m, 3H), 1.85 (s, 2H), 1.51 (s, 3H), 1.16-0.98 (m, 3H). $^{13}$C NMR (101 MHz, CDCl3) δ 162.50, 161.68, 149.42, 143.22, 136.16, 130.50, 128.69, 127.62, 126.88, 124.31, 124.10, 121.84, 120.67, 117.97, 111.80, 101.97, 92.45, 90.77, 62.04, 54.00, 51.27, 36.39, 32.99, 31.46, 27.45, 14.08. $^{19}$F NMR (376 MHz, CDCl$_3$/CFCl3) δ −182.303 to −182.513 (m, 1F). The oxalate salt was precipitated from acetone; Mp 188-189° C. Anal (C$_{25}$H$_{29}$ClFN$_3$O$_2$.C$_2$H$_2$O$_4$.0.5H$_2$O) C, H, N.

(R)—N-(4-(4-(2-Chloro-3-ethylphenyl)piperazin-1-yl)-3-fluorobutyl)-1H-indole-2-carboxamide ((R)-C5a). The compound was prepared from indole-2-carboxylic acid (0.20 g, 1.28 mmol) and (R)-C3b (0.32 g, 1.02 mmol) according to the general amidation procedure C. The crude product was purified by flash chromatography using 30% acetone/CHCl$_3$ as eluent to give the desired product colorless solid (0.32 g, 68.0% yield). $^1$H NMR (400 MHz, CDCl$_3$), $^{13}$C NMR (101 MHz, CDCl$_3$) and $^{19}$F NMR (376 MHz, CDCl$_3$/CFCl$_3$) were identical to the ones described for C5a. The oxalate salt was precipitated from acetone; Mp 193-194° C. Anal (C$_{25}$H$_{30}$ClFN$_4$O·C$_2$H$_2$O$_4$) C, H, N. [α]$_D^{23}$+9.18 (CHCl$_3$, c 1.1), (R)-C5a was analyzed by HPLC Method B retention time=47.907 min and enantiomeric excess was >99%.

(S)—N-(4-(4-(2-Chloro-3-ethylphenyl)piperazin-1-yl)-3-fluorobutyl)-1H-indole-2-carboxamide ((S)-C5a). The compound was prepared from indole-2-carboxylic acid (0.38 g, 2.37 mmol) and (S)-C3b (0.74 g, 1.97 mmol) according to the general amidation procedure C. The crude product was purified by flash chromatography using 30% acetone/CHCl$_3$ as eluent to give the desired product in (0.815 g, 90% yield). $^1$H NMR (400 MHz, CDCl$_3$), $^{13}$C NMR (101 MHz, CDCl$_3$) and $^{19}$F NMR (376 MHz, CDCl$_3$/CFCl$_3$) were identical to the ones described for C5a. The oxalate salt was precipitated from acetone; Mp 195-196° C. Anal (C$_{25}$H$_{30}$ClFN$_4$O·C$_2$H$_2$O$_4$) C, H, N. [α]$_D^{23}$ −9.87 (MeOH, c 0.8), (S)-C5a was analyzed by HPLC Method B, retention time=46.085 min and enantiomeric excess was >99%.

In an alternative process, (R)-C5a and (S)-C5a were also prepared using chiral preparative HPLC from corresponding racemate C5a resulting in >99% ee for each enantiomer.

N-(4-(4-(2-chloro-3-ethylphenyl)piperazin-1-yl)-3-fluorobutyl)benzofuran-2-carboxamide (C5b) was prepared from benzofuron-2-carboxylic acid and C3b according to the general amidation procedure A. The crude product was purified by flash chromatography using 30% acetone/CHCl$_3$ as eluent to give the desired product in 60% yield. 1H NMR (400 MHz, CDCl3) δ 8.02 (s, 1H), 7.67 (ddd, J=7.8, 1.2, 0.7 Hz, 1H), 7.48 (ddd, J=5.4, 4.5, 3.0 Hz, 1H), 7.41 (ddd, J=8.3, 7.2, 1.3 Hz, 1H), 7.32-7.26 (m, 1H), 7.26 (s, 1H), 7.15 (t, J=7.8 Hz, 1H), 7.01 (s, 1H), 6.93 (ddd, J=15.4, 7.8, 1.5 Hz, 1H). 5.03-4.75 (m, 1H), 3.75-3.61 (m, 3H), 3.08 (s, 2H), 2.95 (s, 1H), 2.88 (d, J=0.5 Hz, 3H), 2.83-2.71 (m, 3H), 2.18-1.88 (m, 2H), 1.61 (s, 3H), 1.27-1.13 (m, 3H). 13C NMR (101 MHz, CDCl3) δ 158.92, 154.70, 149.48, 148.62, 143.22, 128.59, 128.21, 126.81, 124.02, 123.68, 122.71, 117.81, 111.69, 110.39, 92.14, 90.36, 62.21, 61.96, 54.09, 51.40, 35.88, 33.17, 32.92, 27.34, 14.08. $^{19}$F NMR (376 MHz, CDCl$_3$/CFCl$_3$) δ −182.530 to −182.660 (m, 1F). The oxalate salt was precipitated from acetone; Anal (C$_{25}$H$_{29}$ClFN$_3$O$_2$.1.3C$_2$H$_2$O$_4$.H$_2$O) C, H, N. Mp 175-176° C.

General Amidation Procedure C. The appropriate aryl carboxylic acid (1.2 mmol) was dissolved in mixture of CHCl$_3$ and dimethylformamide (8:2) and cooled to 0° C. To this solution was added EDCI (1-Ethyl-3-(3-dimethylaminopropyl)carbodiimide) HCl (1.3 mmol) and HOBt (Hydroxybenzotriazole) (1.2 mmol mmol).[45] After 30 min, the aryl amine (1.0 mmol) was added, at 0° C. To this reaction mixture was added DIPEA (N,N-Diisopropylethylamine) (1.5 mmol) and the mixture continued to stir at room temperature for 8 h. The reaction progress was monitored by TLC (thin layer chromatography). After completion of the reaction, the mixture was basified to pH 9 with saturated NaHCO$_3$ water solution. The product was extracted with CHCl$_3$ (50 ml×4). The combined organic fractions were evaporated to afford the crude amide product. All final products were purified using flash column chromatography eluting with CHCl$_3$ and acetone solvent systems, as described.

N-(4-(4-(3-Chloro-5-ethyl-2-methoxyphenyl)piperazin-1-yl)-3-hydroxybutyl)benzo[d][1,3]dioxole-5-carboxamide (113a). The compound was prepared from piperonylic acid (0.25 g, 1.51 mmol) and A9 (0.43 g, 1.25 mmol) according to the general amidation procedure C. The crude product was purified by flash chromatography using 40% acetone/CHCl$_3$ as eluent to give the desired product as a colorless solid (0.34 g, 55% yield). $^1$H NMR (400 MHz, CDCl$_3$) δ 7.38-7.27 (m, 2H), 7.21 (s, 1H), 6.90-6.76 (m, 2H), 6.61 (d, J=1.9 Hz, 1H), 6.02 (s, 2H), 3.95-3.79 (m and s, 2H and 3H), 3.51-3.33 (m, 1H), 3.15 (br s, 4H), 2.86 (m, 2H), 2.55 (m, 4H), 2.44 (dd, J=10.3, 5.3 Hz, 2H), 1.85 (m, 1H), 1.62-1.58 (m, 2H), 1.20 (dd, J=9.2, 6.1 Hz, 3H). $^{13}$C NMR (101 MHz, CDCl$_3$) δ 166.50, 149.93, 147.84, 146.36, 145.72, 140.80, 140.07, 128.83, 128.21, 122.32, 121.47, 116.66, 107.93, 107.52, 101.56, 66.55, 63.74, 59.10, 50.29, 38.39, 36.47, 36.38, 33.26, 28.46, 15.37. The HCl salt was precipitated from acetone; Mp 183-184° C. Anal (C$_{25}$H$_{32}$ClN$_3$O$_5$·HCl·1.5H$_2$O) C, H, N. HRMS=490.21023 [M+H$^+$].

N-(4-(4-(2-Chloro-3-ethylphenyl)piperazin-1-yl)-3-hydroxybutyl)benzo[d][1,3]dioxole-5-carboxamide (113b). The compound was prepared from piperonylic acid (0.23 g, 1.41 mmol) and B8 (0.40 g, 1.28 mmol) according to the general amidation procedure C. The crude product was purified by flash chromatography using 30% acetone/CHCl$_3$ as eluent to give the desired product as colorless solid (0.445 g, 75% yield). $^1$H NMR (400 MHz, CDCl$_3$) δ 7.33 (d, J=8.3 Hz, 2H), 7.30 (s, 1H), 7.16 (t, J=7.7 Hz, 1H), 6.96 (d, J=7.3 Hz, 1H), 6.92 (d, J=8.0 Hz, 1H), 6.81 (d, J=8.0 Hz, 1H), 6.01 (s, 2H), 3.99-3.78 (m, 2H), 3.50-3.34 (m, 1H), 3.07 (br s, 4H), 2.88 (m, 2H), 2.77 (q, J=7.5 Hz, 2H), 2.62 (m, 2H), 2.52-2.35 (m, 2H), 1.88-1.71 (m, 1H), 1.68-1.50 (m, 1H), 1.31-1.13 (m, 3H). $^{13}$C NMR (101 MHz, CDCl$_3$) δ 166.45, 150.06, 149.34, 147.84, 143.31, 129.04, 128.71, 126.88, 124.14, 121.47, 117.96, 107.91, 107.57, 101.54, 66.63, 63.69, 51.59, 38.54, 33.24, 27.45, 14.06. The HCl salt was precipitated from acetone; Mp 198-199° C. Anal (C$_{24}$H$_{30}$ClN$_3$O$_2$·HCl·0.75H$_2$O) C, H, N.

6-Nitrobenzo[d][1,3]dioxole-5-carbaldehyde (115). 3,4-(Methylenedioxy)-benzaldehyde 114 (5.0 g, 33.3 mmol) was added portion-wise to a mixture of dichloroethane and fuming HNO$_3$ (90%, 2 eq) at 0° C. The reaction mixture was allowed to warm to room temperature and stirred for an additional 2 h. Thin layer chromatography was used to monitor the progress of reaction. Ice cold water (50 mL) was added, the mixture was extracted with CHCl$_3$, and washed with brine. The organic phase was dried on anhydrous Na$_2$SO$_4$, filtered and concentrated. The crude product was purified by flash chromatography using 20% EtOAc in hexanes as eluent, to give the desired product as a yellow solid in 85% yield. 1H NMR (400 MHz, CDCl$_3$) δ 10.30 (s, 1H), 7.53 (s, 1H), 7.34 (s, 1H), 6.22 (s, 2H). GC-MS (EI) m/z 195 (M+), (retention time=8.258 min).

5-Nitro-6-vinylbenzo[d][1,3]dioxole (116). Lithium tert-butoxide (LiOtBu) (4.46 g, 55.8 mmol) was added portionwise to a suspension of methyltriphenylphosphonium bromide (7.90 g, 22.3 mmol) in anhydrous THF (100 mL) at −78° C., under argon atmosphere. The reaction mixture was allowed to warm to room temperature and stirred for 3 h. The formation of yellow precipitate was observed, then a solution of 115 (5.0 g, 25.6 mmol) in anhydrous THF (50 mL) was added dropwise over 30 min at 0° C., The reaction mixture was maintained at room temperature and stirred for additional 8 h. The reaction mixture was quenched with addition of saturated aq. NH$_4$Cl solution (50 mL) and the THF was removed under vacuum. The crude product was extracted with EtOAc. The organic layers were combined, dried on anhydrous Na$_2$SO$_4$, filtered, and concentrated. The crude product was purified by flash chromatography using 5% Et$_2$O in hexanes as eluent, to give the desired product as a yellow solid in 85% yield. $^1$H NMR (400 MHz, CDCl$_3$) δ 7.89 (d, J=8.6 Hz, 1H), 7.48 (s, 1H), 6.98 (s, 1H), 6.12 (s, 2H), 5.61 (d, J=17.2 Hz, 1H), 5.41 (d, J=10.6 Hz, 1H). GC-MS (EI) m/z 193 (M$^+$), (retention time=8.039 min).

6-Ethylbenzo[d][1,3]dioxol-5-amine (117). A mixture of 116 (3.17 g, 14.8 mmol) and 10% Pd/C (0.350 g) in ethyl acetate (30 mL) was shaken on a Parr hydrogenator apparatus, under an atmosphere of hydrogen gas (H$_2$, 45 psi) at room temperature, for 45 minutes. The reaction mixture was filtered through a celite pad and evaporated under vacuum. The crude product was purified by flash chromatography using 2% MeOH/CHCl$_3$ as eluent to give the desired product as a yellow oil in 80% yield. $^1$H NMR (400 MHz, CDCl$_3$) δ 6.71-6.49 (m, 1H), 6.28 (d, J=2.0 Hz, 1H), 5.84 (d, 2H), 3.44 (br s, 2H), 2.43 (q, J=7.5 Hz, 2H), 1.203 (t, J=7.5 Hz, 3H). GC-MS (EI) m/z 165 (M$^+$), (retention time=7.138 min).

1-(6-Ethylbenzo[d][1,3]dioxol-5-yl)piperazine (118). A mixture of 117 (2.8 g, 15.13 mmol) and bis(2-chloroethyl)amine HCl (2.69 g, 15.1 mmol) in diethylene glycol monomethyl ether (4.0 mL) was heated at 150° C. for 7 h under argon atmosphere. The reaction mixture was cooled to room temperature, ice cold water was added, and the mixture was basified with 2M aq. NaOH to pH 8-9, followed by extraction with EtOAc. The combined organic layers were washed twice with ice cold water, dried on anhydrous Na$_2$SO$_4$, filtered and concentrated. The crude product was purified by column chromatography using 5% MeOH/CHCl$_3$ as eluent to give the desired product as a as a brown solid in 70% yield. $^1$H NMR (400 MHz, CDCl$_3$) δ 6.71 (d, J=9.8 Hz, 1H), 5.92 (s, 1H), 5.30 (s, 2H), 3.49 (s, 1H), 3.36 (m, 4H), 3.11 (m, 4H), 2.59 (dd, J=14.9, 7.3 Hz, 2H), 1.16 (t, J=7.4 Hz, 3H) ppm. GC-MS (EI) m/z 234 (M$^+$), (retention time=9.833 min).

4-Amino-1-(4-(6-ethylbenzo[d][1,3]dioxol-5-yl)piperazin-1-yl)butan-2-ol (120). The compound was prepared starting from 118 (0.32 g, 1.38 mmol) and A8 (0.36 g, 1.66 mmol) (Grundt et al. "Heterocyclic Analogues of N-(4-(4-(2,3-Dichlorophenyl)Piperazin-1-Yl)Butyl)Arylcarboxamides with Functionalized Linking Chains as Novel Dopamine D3 Receptor Ligands: Potential Substance Abuse Therapeutic Agents" J. Med. Chem. 2007, 50, 4135-4146). The crude product was used in the following steps without further purification.

N-(4-(4-(6-Ethylbenzo[d][1,3]dioxol-5-yl)piperazin-1-yl)-3-hydroxybutyl)-1H-indole-2-carboxamide (121). The compound was prepared from indole-2-carboxylic acid (0.12 g 0.78 mmol) and 120 (0.21 g, 0.654 mmol) according to the general amidation procedure C. The crude product was purified by flash chromatography using 30% acetone/CHCl$_3$ as eluent to give the desired product as a yellow solid (0.15 g, 50% yield). $^1$H NMR (400 MHz, CDCl$_3$) δ 9.14 (s, 1H), 7.64 (d, J=8.0 Hz, 1H), 7.43 (m, 2H), 7.33-7.26 (m, 1H), 7.13 (t, J=7.5 Hz, 1H), 6.84 (s, 1H), 6.71 (s, 2H), 5.90 (s, 2H), 3.92 (m, 2H), 3.48 (m, 1H), 2.84 (m, 4H), 2.65-2.60 (dd, J=20.5, 13.1 Hz, 2H and br s, 1H), 2.44 (d, J=9.6 Hz, 2H), 1.85 (m, 1H), 1.64-1.61 (m, 4H), 1.17 (t, J=7.5 Hz, 3H). $^{13}$C NMR (101 MHz, CDCl$_3$) δ 161.38, 145.67, 144.75, 144.11, 136.03, 133.13, 131.12, 127.81, 124.26, 121.87, 120.54, 111.78, 108.62, 102.02, 101.74, 100.85, 66.51, 63.74, 53.22, 38.09, 33.24, 23.52, 15.30. The HCl salt was precipitated from acetone; Mp 133-135° C. Anal (C$_{26}$H$_{32}$N$_4$O$_4$·HCl·H$_2$O) C, H, N.

N-(4-(4-(6-Ethylbenzo[d][1,3]dioxol-5-yl)piperazin-1-yl)-3-hydroxybutyl)benzofuran-2-carboxamide (122). The compound was prepared from benzfuran-2-carboxylic acid (0.128 g, 0.79 mmol) and 120 (0.215 g, 0.66 mmol) according to the general amidation procedure C. The crude product was purified by flash chromatography using 30% acetone/CHCl$_3$ as eluent to give the desired product as brown oil (0.18 g 58% yield). $^1$H NMR (400 MHz, CDCl$_3$) δ 7.66 (d, J=7.8 Hz, 1H), 7.51 (d, J=8.3 Hz, 2H), 7.45-7.40 (m, 2H), 7.28 (m, 1H), 6.71 (s, 2H), 5.90 (s, 2H), 4.00-3.77 (m, 3H), 3.60-3.43 (m, 1H), 2.86-2.80 (m, 6H), 2.65-2.60 (dt, J=24.3, 12.1 Hz, 2H and br s, 1H), 2.46-2.43 (m, 1H), 1.83 (m, 1H), 1.72-1.47 (m, 2H), 1.17 (t, J=7.5 Hz, 3H). $^{13}$C NMR (101 MHz, CDCl$_3$) δ 158.95, 154.77, 149.03, 145.66, 144.79, 144.09, 133.13, 127.66, 126.63, 123.54, 122.59, 111.79, 110.01, 108.61, 102.02, 100.84, 65.88, 63.82, 53.21, 37.37, 33.64, 23.52, 15.29. The HCl salt was precipitated from acetone; Mp 127-128° C. Anal (C$_{26}$H$_{31}$N$_3$O$_5$·HCl·1.5H$_2$O) C, H, N.

Further abbreviations used in the following examples: DA, dopamine; TM, transmembrane; D2R, dopamine D2 receptor; D3R, dopamine D3 receptor; D4R, dopamine D4 receptor; 5-HT, 5-hydroxytryptamine (serotonin); i.p., intraperitoneal; PPB, potassium phosphate buffer; s.c. subcutaneous; and THC, (6aR,10aR)-delta-9-tetrahydrocannabinol.

Example 2. Radioligand Binding Assays

Binding at dopamine D2-like receptors was determined using previously described methods. (Chen et al. "Tranylcypromine substituted cis-hydroxycyclobutylnaphthamides as potent and selective dopamine D(3) receptor antagonists." J. Med. Chem. 2014, 57, 4962-4968) Membranes were prepared from HEK293 cells expressing human D2R, D3R or D4R, grown in a 50:50 mix of DMEM and Ham's F12 culture media, supplemented with 20 mM HEPES, 2 mM L-glutamine, 0.1 mM non-essential amino acids, 1× antibiotic/antimycotic, 10% heat-inactivated fetal bovine serum, and 200 μg/mL hygromycin (Life Technologies, Grand Island, NY) and kept in an incubator at 37° C. and 5% CO$_2$. Upon reaching 80-90% confluence, cells were harvested using pre-mixed Earle's Balanced Salt Solution (EBSS) with 5 μM EDTA (Life Technologies) and centrifuged at 3000 rpm for 10 min at 21° C. The supernatant was removed and the pellet was resuspended in 10 mL hypotonic lysis buffer (5 mM MgCl$_2$.6H$_2$O, 5 mM Tris, pH 7.4 at 4° C.) and centrifuged at 20,000 rpm for 30 min at 4° C. The pellet was then resuspended in fresh EBSS buffer made from 8.7 g/L Earle's Balanced Salts without phenol red (US Biological, Salem, MA), 2.2 g/L sodium bicarbonate, pH to 7.4. A Bradford protein assay (Bio-Rad, Hercules, CA) was used to determine the protein concentration and membranes were diluted to 500 µg/mL and stored in a −80° C. freezer for later use.

Radioligand competition binding experiments were conducted using thawed membranes. Test compounds were freshly dissolved in 30% DMSO and 70% H$_2$O to a stock concentration of 100 µM. To assist the solubilization of free-base compounds, 10 µl of glacial acetic acid was added along with the DMSO. Each test compound was then diluted into 13 half-log serial dilutions using 30% DMSO vehicle; final test concentrations ranged from 10 µM to 10 pM. Previously frozen membranes were diluted in fresh EBSS to a 100 µg/mL (for hD2R or hD3R) or 200 µg/mL (hD4R) stock for binding. Radioligand competition experiments were conducted in glass tubes containing 300 µl fresh EBSS buffer with 0.2 mM sodium metabisulfite, 50 µl of diluted test compound, 100 µl of membranes (10 µg total protein for hD2R or hD3R, 20 µg total protein for hD4R), and 50 µl of [$^3$H]N-methylspiperone (0.4 nM final concentration; Perkin Elmer). Nonspecific binding was determined using 10 µM butaclamol (Sigma-Aldrich, St. Louis, MO) and total binding was determined with 30% DMSO vehicle. All compound dilutions were tested in triplicate and the reaction incubated for one hour at room temperature. The reaction was terminated by filtration through Whatman GF/B filters, presoaked for one hour in 0.5% polyethylenimine, using a Brandel R48 filtering manifold (Brandel Instruments, Gaithersburg, MD). The filters were washed 3 times with 3 mL of ice cold EBSS buffer and transferred to scintillation vials. 3 mL CytoScint liquid scintillation cocktail (MP Biomedicals, Solon, OH) was added and vials were counted using a Perkin Elmer Tri-Carb 2910 TR liquid scintillation counter (Waltham, MA). IC$_{50}$ values for each compound were determined from dose-response curves and K$_i$ values were calculated using the Cheng-Prusoff equation; these analyses were performed using GraphPad Prism version 5.00 for Windows (GraphPad Software, San Diego, CA). Reported K$_i$ values were determined from least three independent experiments.

TABLE 1A

Human D$_2$R-Family Receptor Subtype Binding Data on piperazine butyl arylcarboxamide derivatives[a]

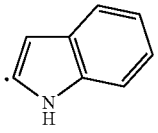

| Compd. | Ar | R$^1$ | R$^2$ | R$^3$ | Linker[c] | cLogP[b] | PSA | D$_2$R | D$_3$R | D$_4$R | D$_2$/D$_3$ | D$_4$/D$_3$ | D$_4$/D$_2$ |
| | | | | | | | | K$_i$ ± SEM (nM) | | | | | |
|---|---|---|---|---|---|---|---|---|---|---|---|---|---|
| 18 |  | Cl | H | H | 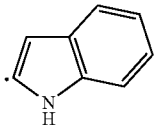 | 5.76 | 47.61 | 5.50 ± 0.805 | 0.142 ± 0.0249 | 334 ± 113 | 39 | 2352 | 61 |
| 19 |  | Cl | H | H | 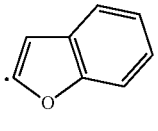 | 5.17 | 67.84 | 151 ± 25.4 | 0.362 ± 0.0474 | 5523 ± 1655 | 417 | 15257 | 37 |
| 20 |  | Cl | H | H | 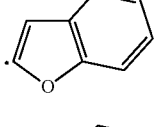 | 5.74 | 44.81 | 6.34 ± 0.959 | 0.153 ± 0.00527 | 356 ± 64.4 | 41 | 2327 | 56 |
| 21 |  | Cl | H | H | 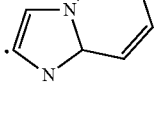 | 5.14 | 65.04 | 164 ± 32.4 | 0.985 ± 0.105 | 2381 ± 110 | 166 | 2417 | 15 |
| 22 |  | Cl | H | H | | 5.52 | 51.18 | 5.64 ± 0.98 | 0.33 ± 0.085 | 819 ± 175 | 17.1 | 2482 | 145.2 |

TABLE 1A-continued

Human D₂R-Family Receptor Subtype Binding Data on piperazine butyl arylcarboxamide derivatives[a]

| Compd. | Ar | R¹ | R² | R³ | Linker[c] | cLogP[b] | PSA | $D_2R$ $K_i \pm$ SEM (nM) | $D_3R$ $K_i \pm$ SEM (nM) | $D_4R$ $K_i \pm$ SEM (nM) | $D_2/D_3$ | $D_4/D_3$ | $D_4/D_2$ |
|---|---|---|---|---|---|---|---|---|---|---|---|---|---|
| 23 | imidazo[1,2-a]pyridine | Cl | H | H | sec-butanol (OH) | 4.93 | 71.41 | 193 ± 40.5 | 4.23 ± 0.84 | 11300 | 45.6 | 2671 | 58.5 |
| 24 | 2-methyl-imidazo[2,1-b]thiazole | Cl | H | H | propyl | 5.43 | 51.18 | 4.65 ± 1.24 | 0.94 ± 0.13 | 143 ± 3.18 | 4.9 | 152 | 30.8 |
| 25 | 4-ethyl-imidazole | Cl | H | H | propyl | 5.38 | 59.97 | 12.5 ± 1.07 | 1.14 ± 0.17 | 500 ± 30.9 | 11.0 | 439 | 40.0 |
| 26 | 4-methyl-imidazole | Cl | H | H | propyl | 4.391 | 59.97 | 12.2 ± 2.58 | 0.62 ± 0.096 | 529 ± 42.3 | 19.7 | 853 | 43.4 |
| 27 | 4-methyl-imidazole | Cl | H | H | sec-butanol (OH) | 3.79 | 80.2 | 150 ± 13.1 | 11.2 ± 2.66 | 1960 ± 344 | 13.4 | 175 | 13.1 |
| 28 | indole | H | OMe | Cl | propyl | 5.53 | 56.84 | 27.8 ± 6.71 | 0.341 ± 0.0312 | 1045 ± 279 | 82 | 3065 | 38 |
| 29 | indole | H | OMe | Cl | sec-butanol (OH) | 4.93 | 77.07 | 17127 ± 5087 | 6.29 ± 0.877 | >>100 μM ± 2723 | — | — | |
| 30 | benzofuran | H | OMe | Cl | propyl | 5.50 | 54.04 | 137 ± 9.00 | 3.19 ± 0.268 | 714 ± 293 | 43 | 224 | 5.2 |
| 31 | benzofuran | H | OMe | Cl | sec-butanol (OH) | 4.91 | 74.27 | 1619 ± 339 | 36.1 ± 5.00 | 5285 ± 319 | 45 | 146 | 3.3 |
| 35 | 4-methyl-imidazole | Cl | H | H | propenyl | 4.31 | 59.97 | 16.1 ± 1.2 | 1.28 ± 0.22 | 503 ± 157 | 12.6 | 393 | 31.2 |

TABLE 1A-continued

Human D₂R-Family Receptor Subtype Binding Data on piperazine butyl arylcarboxamide derivatives[a]

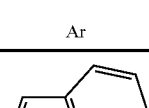

| Compd. | Ar | $R^1$ | $R^2$ | $R^3$ | Linker[c] | cLogP[b] | PSA | $D_2R$ $K_i \pm$ SEM (nM) | $D_3R$ $K_i \pm$ SEM (nM) | $D_4R$ $K_i \pm$ SEM (nM) | $D_2/D_3$ | $D_4/D_3$ | $D_4/D_2$ |
|---|---|---|---|---|---|---|---|---|---|---|---|---|---|
| 40 | indole | Cl | H | H | CH(OH) propyl | 5.05 | 67.84 | 6.83 ± 0.53 | 0.20 ± 0.018 | 305 ± 70.5 | 34.2 | 1525 | 44.7 |

[a]Binding inhibition values determined using HEK 293 cells transfected with hD2LR or hD3R and [3H]N-methylspiperone radioligand as described in (Chen et al. "Tranylcypromine substituted cis-hydroxycyclobutylnaphthamides as potent and selective dopamine D(3) receptor antagonists." J. Med. Chem. 2014, 57, 4962-4968)
[b]Partition coefficients (clogP) were calculated using ChemDraw Professional Ultra 15.0.
[c]"Linker" represents —(R⁵)═══C(R⁴)— of Formula (I).

TABLE 1B

| | | [³H]-N-methylspiperone competition[a] | | |
|---|---|---|---|---|
| Compounds | Structures | $D_2R$ $K_i \pm$ SEM (nM) | $D_3R$ $K_i \pm$ SEM (nM) | $D_2/D_3$ |
| (R)-29 | | 10200 ± 1870 | 5.97 ± 1.19 | 1709 |
| (S)-29 | | 11600 ± 1150 | 33.4 ± 8.46 | 347 |

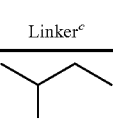

TABLE 1B-continued
| Compounds | Structures | [³H]-N-methylspiperone competition[a] | | |
|---|---|---|---|---|
| | | $D_2R$ $K_i$ ± SEM (nM) | $D_3R$ $K_i$ ± SEM (nM) | $D_2/D_3$ |
| (±)-29 | 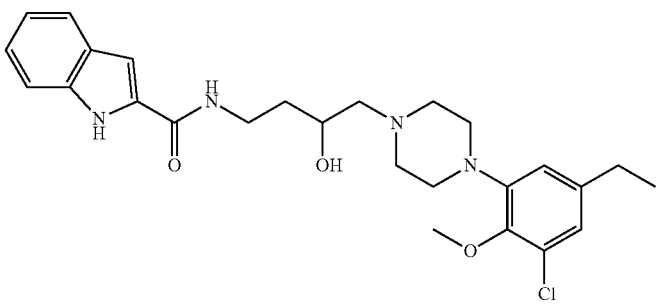 [SMILES: CCc1cc(Cl)c(OC)c(N2CCN(CC(O)CCNC(=O)c3cc4ccccc4[nH]3)CC2)c1] | 11400 ± 3270 | 6.84 ± 1.18 | 1667 |
| (R)-19 | 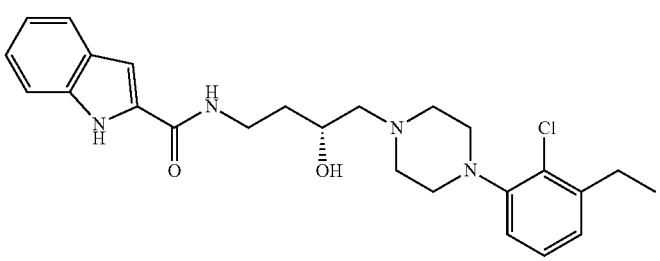 [SMILES: CCc1cccc(N2CCN(C[C@H](O)CCNC(=O)c3cc4ccccc4[nH]3)CC2)c1Cl] | 68.1 ± 12.3 | 0.245 ± 0.0915 | 278 |
| (S)-19 | 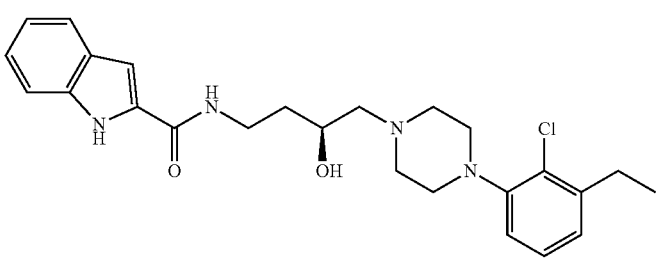 [SMILES: CCc1cccc(N2CCN(C[C@@H](O)CCNC(=O)c3cc4ccccc4[nH]3)CC2)c1Cl] | 200 ± 57.9 | 0.700 ± 0.286 | 286 |
| (±)-19 | 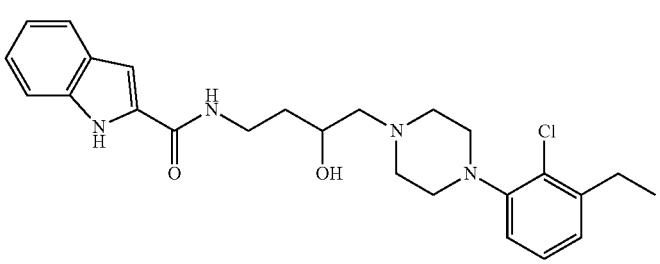 [SMILES: CCc1cccc(N2CCN(CC(O)CCNC(=O)c3cc4ccccc4[nH]3)CC2)c1Cl] | 119 ± 11.1 | 0.351 ± 0.114 | 339 |
| C4a | 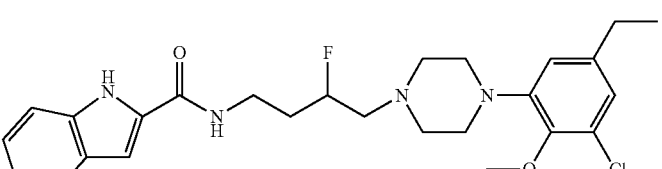 | 27100 ± 11600 | 28.0 ± 5.53 | 968 |
| C4b | 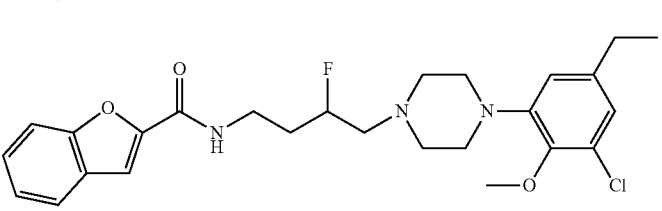 [SMILES: CCc1cc(Cl)c(OC)c(N2CCN(CC(F)CCNC(=O)c3cc4ccccc4o3)CC2)c1] | 9740 ± 2100 | 89.9 ± 12.3 | 108 |

TABLE 1B-continued

| Compounds | Structures | D₂R $K_i \pm$ SEM (nM) | D₃R $K_i \pm$ SEM (nM) | D₂/D₃ |
|---|---|---|---|---|
| C5a | 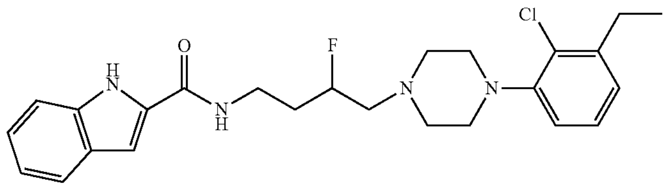 [SMILES: CCc1cccc(N2CCN(CC(F)CCNC(=O)c3cc4ccccc4[nH]3)CC2)c1Cl] | 124 ± 15.8 | 0.482 ± 0.150 | 257 |
| C5b | 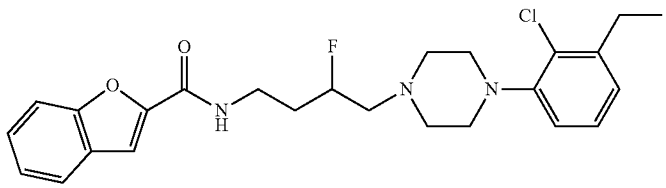 [SMILES: CCc1cccc(N2CCN(CC(F)CCNC(=O)c3cc4ccccc4o3)CC2)c1Cl] | 295 ± 30.1 | 2.09 ± 0.484 | 141 |

[a] The values represent the arithmetic mean ± SEM of triplicate determinations from at least three independent experiments. IC₅₀ values for each compound were determined from dose-response curves and $K_i$ values were calculated by the Cheng-Prusoff equation using GraphPad Prism version 6.00 for Macintosh. The competition experiments were performed, similarly to what previously reported, in presence of 0.4 nM [³H]-N-methylspiperone, 10 half-log serial dilutions of test drugs in triplicate and membrane preparations from stably transfected HEK293 cells expressing D₂ₗR or D₃R (D₂ₗR 20 μg/well and D₃R 20 μg/well). The binding experiments were conducted in 96-well plates containing 300 μl fresh binding buffer (EBSS at pH 7.4), 50 μl of diluted test compound, 100 μl of membranes and 50 μl of radioligand. The binding reactions were incubated for 1 hour at room temperature and then terminated by filtration through Perkin Elmer UniFilter-96 GF/B filters, presoaked for one hour in 0.5% polyethylenimine

TABLE 1C

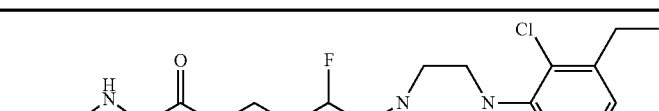

| Compound | Ar1 | X | Ar2 | cLogP | tPSA | D₂R $K_i \pm$ SEM (nM) | D₃R $K_i \pm$ SEM (nM) | D₂/D₃ |
|---|---|---|---|---|---|---|---|---|
| C4a | | | | 5.40 | 56.84 | 20800 ± 7060 (n = 6) | 27.9 ± 5.64 (n = 6) | 746 |
| (R)-C4a | | | | 5.40 | 56.84 | 21400 ± 1500 (n = 3) | 13.0 ± 2.94 (n = 3) | 1646 |
| (S)-C4a | | | | 5.40 | 56.84 | 18900 ± 2720 (n = 3) | 35.3 ± 5.15 (n = 3) | 535 |

TABLE 1C-continued
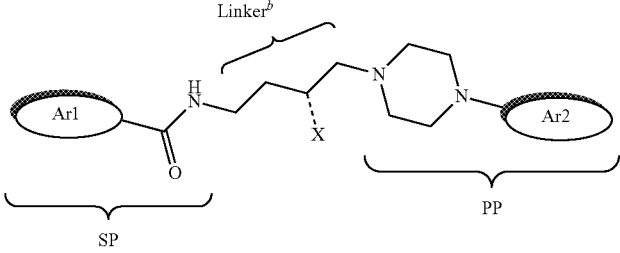
| Compound | Ar1 | X | Ar2 | cLogP | tPSA | D$_2$R K$_i$ ± SEM (nM) | D$_3$R K$_i$ ± SEM (nM) | D$_2$/D$_3$ |
|---|---|---|---|---|---|---|---|---|
| C5a | 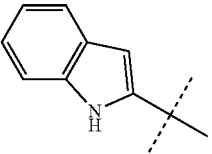 |  | 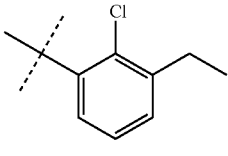 | 5.63 | 47.61 | 247 ± 57.4 (n = 7) | 0.756 ± 0.185 (n = 9) | 327 |
| (R)-C5a | 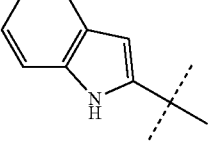 |  | 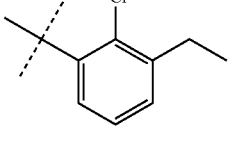 | 5.63 | 47.61 | 80.2 ± 13.8 (n = 4) | 0.373 ± 0.061 (n = 3) | 215 |
| (S)-C5a | 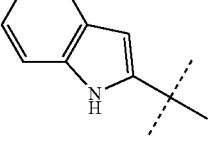 |  | 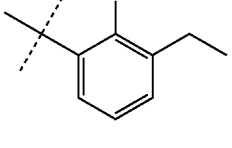 | 5.63 | 47.61 | 891 ± 305 (n = 4) | 0.840 ± 0.156 (n = 3) | 1060 |
| C4b | 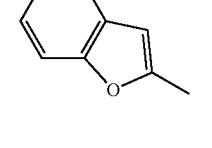 | 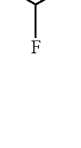 | 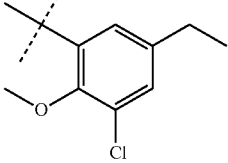 | 5.37 | 54.04 | 10800 ± 2290 (n = 3) | 99.9 ± 13.4 (n = 3) | 108 |
| C5b | 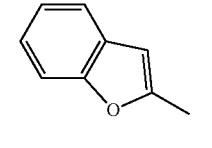 | 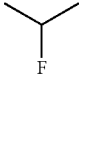 | 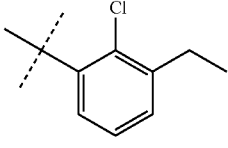 | 5.60 | 44.81 | 328 ± 33.5 (n = 4) | 2.45 ± 0.510 (n = 7) | 134 |
| 113a | 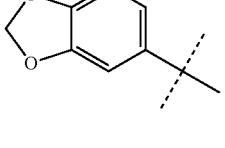 | 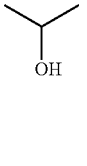 | 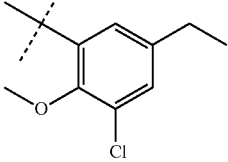 | 4.53 | 83.5 | 364 ± 101 (n = 3) | 24.5 ± 4.44 (n = 4) | 15 |
| 113b | 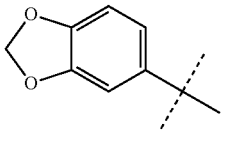 | 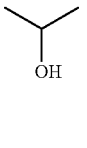 | 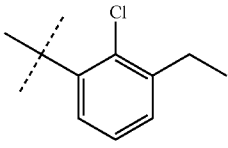 | 4.76 | 74.27 | 424 ± 79.9 (n = 3) | 3.02 ± 0.742 (n = 5) | 140 |

TABLE 1C-continued

| Compound | Ar1 | X | Ar2 | cLogP | tPSA | D$_2$R K$_i$ ± SEM (nM) | D$_3$R K$_i$ ± SEM (nM) | D$_2$/D$_3$ |
|---|---|---|---|---|---|---|---|---|
| 121 | 2-indolyl | OH | 5-ethyl-benzodioxole | 4.27 | 86.3 | 537 ± 41.3 (n = 3) | 4.31 ± 1.07 (n = 3) | 125 |
| 122 | 2-benzofuranyl | OH | 5-ethyl-benzodioxole | 4.24 | 83.5 | 1440 ± 48.8 (n = 3) | 23.6 ± 7.35 (n = 3) | 61 |
| 29 | 2-indolyl | OH | 5-ethyl-3-chloro-2-methoxyphenyl | 4.93 | 77.07 | 13200 ± 3770 (n = 4) | 7.61 ± 1.17 (n = 4) | 1735 |
| (R)-29 | 2-indolyl | OH (R) | 5-ethyl-3-chloro-2-methoxyphenyl | 4.93 | 77.07 | 10800 ± 2590 (n = 4) | 7.40 ± 1.09 (n = 4) | 1459 |
| (S)-29 | 2-indolyl | OH (S) | 5-ethyl-3-chloro-2-methoxyphenyl | 4.93 | 77.07 | 13500 ± 1230 (n = 3) | 37.9 ± 9.70 (n = 4) | 356 |
| 19 | 2-indolyl | OH | 2-chloro-6-ethylphenyl | 5.16 | 67.84 | 132 ± 12.7 (n = 4) | 0.433 ± 0.116 (n = 6) | 305 |

TABLE 1C-continued

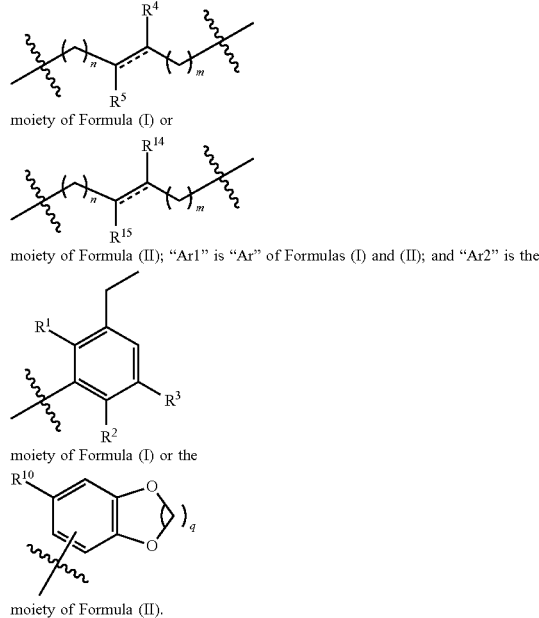

| Compound | Ar1 | X | Ar2 | cLogP | tPSA | $D_2R$ $K_i \pm$ SEM (nM) | $D_3R$ $K_i \pm$ SEM (nM) | $D_2/D_3$ |
|---|---|---|---|---|---|---|---|---|
| (R)-19 | 2-indolyl | CH(OH) | 2-Cl-6-Et-phenyl | 5.16 | 67.84 | 75.8 ± 13.7 (n = 4) | 0.290 ± 0.085 (n = 6) | 261 |
| (S)-19 | 2-indolyl | CH(OH) | 2-Cl-6-Et-phenyl | 5.16 | 67.84 | 219 ± 66.2 (n = 4) | 0.886 ± 0.296 (n = 6) | 247 | aThe values represent the arithmetic mean ± SEM of triplicate determinations from at least three independent experiments IC$_{50}$ values for each compound were determined from dose-response curves and K$_i$ values were calculated by the Cheng-Prusoff equation (Cheng, Y.; Prusoff, W. H., Relationship Between The Inhibition Constant (K1) and The Concentration of Inhibitor Which Causes 50 Per Cent Inhibition (I50) of An Enzymatic Reaction. Biochem. Pharmacol. 1973, 22, 3099-3108) using GraphPad Prism version 6.00 for Macintosh. n = number of independent experiments, each performed in triplicate.
b"Linker" represents moiety of Formula (I) or moiety of Formula (II); "Ar1" is "Ar" of Formulas (I) and (II); and "Ar2" is the moiety of Formula (I) or the moiety of Formula (II).

Pharmacological Results and Discussion

The binding affinities of the compounds were evaluated by performing competition binding studies with [$^3$H]N-methylspiperone using membranes prepared from HEK293 cells expressing either the human $D_2R$ or $D_3R$.

Binding data for the full length substituted ligands are shown in Tables 1A and 1B. In addition, cLogP values and polar surface area (PSA) were calculated to provide measures of lipophilicity and predicted brain penetration respectively, for the full length compounds. The majority of analogues demonstrated binding affinities in the low to sub-nanomolar range for $D_3R$. In the 1-(2-chloro-3-ethylphenyl)piperazine based series (18-27), both 18 and 19 showed high binding affinities for $D_3R$ ($K_i$=0.14 and 0.36 nM, respectively). Moreover, 19 showed $D_2R/D_3R$ selectivity of >400 fold. When the indole moiety of 18 and 19 was replaced with benzofuran, subnanomolar binding affinities were maintained for both 20 and 21, but $D_3R$ selectivity was reduced due to an improvement in $D_2R$ affinities. When the indole ring was also replaced with other heteroaryl ring systems, such as 2-(imidazo[1,2-a]pyridine) (22 and 23), 5-(6-methylimidazo[2,1-b]thiazole) (24), 2-(4-ethyl-1H- imidazole) (25), 2-(4-methyl-1H-imidazole) (26 and 27). In most of cases, although high $D_3R$ binding affinities were retained, relative improvements in $D_2R$ binding affinities reduced $D_3R$ selectivity. No major change in the affinity and selectivity of 26 was observed when a trans-butenyl linker was introduced between the aryl amide and piperazine moiety to afford 35.

In the more highly substituted 1-(3-chloro-5-ethyl-2-methoxyphenyl)piperazine-based series (28-31), the indole 28 showed a similar binding profile to its analogue 18. Compound 29 exhibited high affinity ($K_i$=6.29 nM) and the greatest $D_3R$ versus $D_2R$ binding selectivity, (~2700 fold) of all the 4-phenylpiperazines. The benzofuran derivatives 30 and 31 showed reduced $D_3R$ binding affinities and either similar or lower $D_3R$ selectivities, in comparison to 20 and 21, respectively. The introduction of a 3-OH group in the butyl linking chain resulted in lower cLogP values, predicting decreased lipophilicity, compared to corresponding parent aliphatic compounds. Compared to all the 3-OH-butyl analogues, the 2-OH-butyl derivative 40 showed high $D_3R$ affinity ($K_i$=0.20 nM) but it exhibited lower $D_3R$ selectivity, similar to compounds that had no OH substitution in the linking chain. None of the compounds demonstrated high binding affinity for $D_4R$.

The full length molecules based on both 3-chloro-5-ethyl-2-methoxyphenylpiperazine and 2-chloro-3-ethylphenylpiperazine showed high $D_3R$ binding affinities and selectivities over $D_2R$.

The replacement of the indole with other heteroaryl ring systems showed no improvement in $D_3R$ selectivity.

As shown in Table 1C, the binding affinities for the racemates of 29 and 19 were compared to their chiral analogs and fluoro analogs. (R)-29 exhibited very similar $D_3R$ binding affinity to the racemate with a $K_i$=7.40 nM and was similarly selective over $D_2R$ (1459-fold). Whereas, (S)-29 was the distomer with a $K_i$=37.9 nM, (~5-fold enantioselectivity). (±)-19, showed sub-nanomolar binding affinity at $D_3R$ ($K_i$=0.433 nM) and (R)-19 also exhibited similarly high $D_3R$ binding affinity ($K_i$=0.290 nM). (S)-19 ($K_i$=0.886 nM) was also the distomer, although its binding affinity was only reduced by ~3-fold compared to (R)-19. Further, both the R and S enantiomers of 19 were less selective at $D_3R$ over $D_2R$ when compared to similar enantiomers of 29, although still in the 300-fold range.

In comparison, the 3-F analogues with an indole-3-carboxamide demonstrated high $D_3R$ affinity and thus it was of interest to resolve the racemates C4a and C5a. Both the R-enantiomers (R)-C4a,C5a were the eutomers at $D_3R$. (R)-C4a exhibited ~2-fold higher binding affinity at $D_3R$ ($K_i$=13.0 nM) compared to (±)-C4a and ~1650-fold selectivity over $D_2R$ (2-fold higher than (±)-C4a). Whereas, (S)-C4a showed reduced $D_3R$ binding affinity and selectivity ($K_i$=35.3 nM, 535-fold over $D_2R$). Moreover, (R)-C5a exhibited sub-nanomolar affinity at $D_3R$ ($K_i$=0.373 nM). Interestingly, (S)-C5a also displayed sub-nanomolar binding affinity at $D_3R$ with $K_i$=0.840 nM and was >1000-fold selective over $D_2R$. Thus, the selectivity profile of (S)-C5a at $D_3R$ over $D_2R$ was dramatically increased and ~5-fold higher than either (±)-C5a (327-fold) or (R)-C5a (215-fold).

(R)-C4a and (R)-C5a with the 3-F in the linking chain showed similar binding affinities and selectivity profiles to their corresponding 3-OH analogues, (R)-29 and (R)-19. Whereas, (S)-C4a and (S)-C5a showed similar binding affinities to (S)-29 and (S)-19 respectively; however, (S)-C5a exclusively showed higher selectivity over $D_2R$ and was approximately 4-fold more selective than (S)-19, demonstrating the role of substitution and stereochemistry of the linking chain in the binding profile of this series of molecules.

Example 3. Microsomal Metabolism Studies: Rat, Rhesus Monkey, and Human Liver Microsomes Phase I metabolic stability assays were conducted on racemic compound (±)-29 and each enantiomer (R)-29 and (S)-29. The results, provided in the table below, illustrate the Phase I metabolic stability in human liver microsomes where 70-76% of intact drug remains after 1 hour for all compounds.

| Compound | Species | % at 0 min. | % at 30 min. | % at 60 mm. |
|---|---|---|---|---|
| (±)-29 | Rat | 100 | 95 | 85 |
| (±)-29 | Monkey | 100 | 79 | 66 |
| (±)-29 | Human | 100 | 89 | 73 |
| (R)-29 | Rat | 100 | 80 | 68 |
| (R)-29 | Human | 100 | 79 | 70 |
| (S)-29 | Rat | 100 | 70 | 57 |
| (S)-29 | Monkey | 100 | 56 | 38 |
| (S)-29 | Human | 100 | 84 | 76 |

Rat Liver Microsome Metabolic Stability: Test compounds including 3-F analogues (C4a, C4b, C5a, C5b) and 29, 19 as well as the R-, S-enantiomers of C4a, C5a, 29 and 19 were screened for phase I metabolic stability in rat liver microsomes. Of all the four 3-F analogues, C4a was the most stable with ~75% intact remaining, whereas C5a, C5b, C4b showed lower stability with 38%, 34% and 12% parent remaining, respectively. Individual R- and S-enantiomers of C4a and C5a showed higher stability with 57-70% intact remaining. Lastly, compounds 29 and 19 as well as their R- and S-enantiomers were found to be metabolically stable with 57-86% remaining at 60 min.

Example 4. Studies in Rats with Compound 29

Rat studies were conducted on compound (±)-29 by testing its effects on acquisition and maintenance of oxycodone self-administration, extinction, and oxycodone-induced reinstatement of drug-seeking behavior in rats. The effects of compound (±)-29 on oxycodone analgesia and naloxone-precipitated conditioned place aversion (CPA) in chronically oxycodone-treated rats were conducted to determine whether compound (±)-29 pretreatment compromises therapeutic opioid analgesia and/or alters withdrawal responses.

Materials and Methods

Animals: Male Long-Evans rats (275-325 g) (Charles-River Laboratories, Raleigh, N.C.) were used throughout this study. Upon arrival, they were housed in an animal facility under a reversed 12 h light-dark cycle (light on at 7:00 PM) with free access to food and water. They were allowed to acclimatize to the new environment at least for 7 days prior to study initiation. All procedures were approved by the Animal Care and Use Committee (IACUC) of the U.S. National Institute on Drug Abuse (NIDA) and were consistent with *the Guide for the Care and Use of Laboratory Animals, 8th edition* (National Research Council, 2011). Experiment 1: Effects of Compound (±)-29 on Acquisition of Oxycodone Self-Administration Surgery and self-administration procedures: The i.v. catheterization surgery and i.v. oxycodone self-administration procedures are the same as reported previously (You et al, 2017). Rats (300-350 g) used for oxycodone self-administration were first implanted with an intravenous catheter. They were anaesthetized with pentobarbital (30 mg/kg i.p.) supplemented with chloral hydrate (140 mg/kg, i.p.). A small incision was next made to the right of the midline of the neck and the external jugular vein was externalized and an i.v. catheter, made of microrenathane (Braintree Scientific Inc., Braintree, MA, USA) was inserted with its tip reaching right atrium. The catheter was secured to the vein with silk suture and the other end fed subcutaneously around the back of the neck to exit near the back of the skull. The end was slipped over a bent 24-gauge stainless steel cannula (Plastic One Inc., Roanoke, VA, USA) with a threaded head used to secure a dummy cannula and, during experimentation, an infusion line. The catheter and the guide cannula were then secured to the skull with four stainless steel screws threaded into the skull and dental cement and the wound was sutured. After surgery, the catheters were flushed daily with a gentamicin-heparin-saline solution (0.1 mg/ml gentamicin and 30 IU/ml heparin) as precaution against catheter clogging and infection. The animals were allowed to recover for at least 5 days before behavioral training started.

Oxycodone self-administration training was conducted in an operant conditioning chamber equipped with two response levers (Med Associates Inc., Georgia, VT, USA). Each rat was trained daily in 3 h sessions to press the active lever for oxycodone infusions on a fixed-ratio 1 (FR 1) schedule of reinforcement. Response on the active lever resulted in the activation of cue light and tone and infusion of an 0.08 ml oxycodone solution over 4.6 sec. This time also served as a timeout period during which the cue light and tone were kept on and the animal's response on the active lever was recorded but had no scheduled consequence. Each animal's response on the inactive lever was recorded but not rewarded throughout training and testing.

Three groups of rats (n=8/group) were used to test the effects of compound ($\pm$)-29 on acquisition of oxycodone self-administration. After recovery from surgery, they were transported daily to the test room, placed in the self-administration chambers and allowed to self-administer oxycodone (50 µg/kg/infusion) in a daily 3 h session for 10 sessions. Fifteen min before each of the initial 5 sessions, the 3 groups of rats were first systemically injected with either vehicle (25% 2-hydroxypropyl-$\beta$-cyclodextrin) or a dose of compound ($\pm$)-29 (5 or 15 mg/kg, i.p.). The animals were then tested for additional 5 sessions without compound ($\pm$)-29 pretreatment. Animals' responses on the levers and oxycodone infusions were recorded. Acquisition was operationally defined as the time course of learning intravenous drug self-administration.

Experiment 2: Effects of Compound ($\pm$)-29 on Maintenance of Oxycodone Self-Administration and Oxycodone-Seeking after Oxycodone was Replaced by Saline Four groups of rats (n=7/group) were first trained to self-administer oxycodone at a dose of 100 µg/kg/infusion for 2 weeks followed by 50 µg/kg/infusion for the rest of the training sessions and for the test session. The daily self-administration of oxycodone at the low dose continued until the average oxycodone infusions/session varied less than 10% over 3 consecutive sessions (normally 6-10 sessions were required to meet this criterion of stability). On the following test day, the groups of rats were first systemically injected with either vehicle or a dose of compound ($\pm$)-29 (5, 15 or 25 mg/kg, i.p.), and 15 min later, the animals were allowed to self-administer oxycodone.

Following completion of the self-administration testing, the rats continued to self-administer oxycodone (50 µg/kg/infusion) for additional 4 sessions. On the next day, the animals were re-assigned into 3 groups, and pretreated with either vehicle or 1 of the 2 doses of compound ($\pm$)-29 (5 or 15 mg/kg). Fifteen min later, the animals were placed in the chambers, and allowed to lever-press for an extinction session during which saline was substituted for cocaine. Other conditions remain the same as cocaine session. The responses on the active and inactive levers, and number of saline infusions were recorded.

Experiment 3: Oxycodone Self-Administration Under Progressive Ratio (PR) Reinforcement Initial oxycodone self-administration under FR1 reinforcement was identical to that outlined above. After stable oxycodone self-administration under FR1 reinforcement was established, the subjects were switched to oxycodone (0.05 mg/kg/injection) self-administration under a PR schedule, during which the work requirement (lever presses) needed to receive a single i.v. oxycodone infusion was progressively raised within each test session according to the following PR series: 1, 2, 4, 6, 9, 12, 15, 20, 25, 32, 40, 50, 62, 77, 95, 118, 145, 178, 219, 268, 328, 402, 492, and 603 until break-point (BP) was reached. BP was defined as the maximal work load (lever presses) completed for an oxycodone infusion before a 1 h period during which no infusion was obtained by the animal. The PR schedule is computer programmed to progress to a maximum of 603 and the average BP was ~150. Animals were allowed to continue daily sessions of oxycodone self-administration under PR reinforcement conditions until day-to-day variability in BP was within 1-2 ratio increments for three consecutive days. Once a stable BP was established, subjects were assigned to four subgroups to determine the effects of three different doses of compound ($\pm$)-29 (0, 5, 15, and 25 mg/kg, i.p.) on PR BP for oxycodone self-administration. Between-subjects design was chosen for this experiment because it is relatively difficult to re-establish stable BP oxycodone self-administration after each test under PR reinforcement as compared with oxycodone self-administration under FR1 conditions.

Experiment 4: Effects of Compound ($\pm$)-29 on Oxycodone-Triggered Reinstatement of Drug-Seeking Behavior For the three groups from Experiment 2, extinction sessions continued without drug treatment until the rats' average active lever-presses/session decreased to less than 10 responses over 3 consecutive sessions. On the following day, 2 groups of rats were first pretreated with 1 of 2 doses of compound ($\pm$)-29 (5 or 15 mg/kg) while another group with vehicle. Fifteen min following pretreatment, all the animals received a non-contingent injection of oxycodone priming (1 mg/kg, i.p.) and then were placed into the same operant chambers for another extinction session. Responses on the active and inactive levers and total saline infusions were recorded.

Experiment 5: Effects of Compound ($\pm$)-29 on Naloxone-Precipitated Conditioned Place Aversion (CPA)

Naloxone-precipitated CPA was tested in a place-conditioning apparatus (Med Associates, St Albans, VT) consisting of two side compartments (21 cm×28 cm) and a central gray connecting area (21 cm×12.5 cm); a sliding door separated each compartment from the connecting area. The two side compartments differed in wall color (black vs white), floor type (stainless steel net vs stainless steel grid), and illumination. Before the experiment started, all the animals were allowed to explore the conditioning apparatus for 15 min (preconditioning). Rats that displayed significant bias in one side compartment (≥200 s in one rather than in the other side compartment) during preconditioning session were excluded from the study.

Figure 4A:
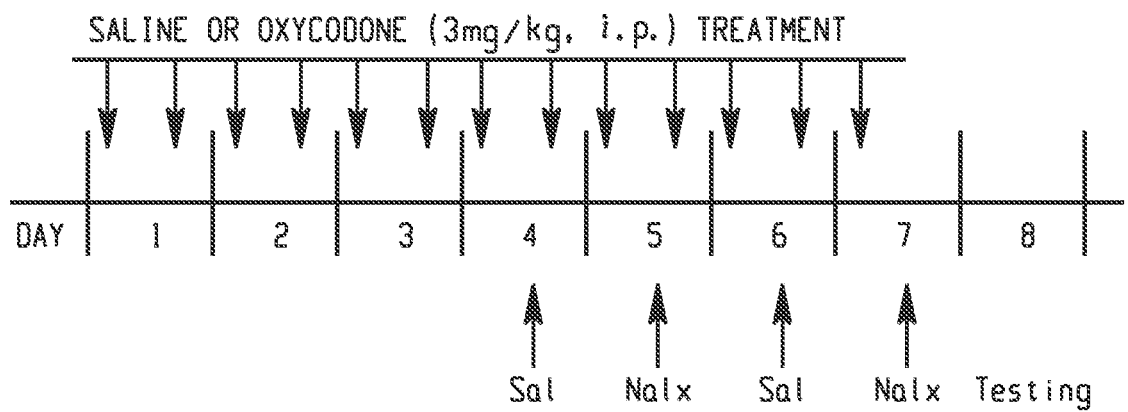
FIG. 4A describes the procedure for the naloxone-precipitated conditioned place aversion in chronic oxycodone treated rats and FIG. 4B illustrates the inhibition of naloxone-precipitated conditioned place aversion in chronic oxycodone-treated rats with compound (±)-29.

Six groups (n=8/group) of rats were involved in this test, 3 groups were chronically treated with oxycodone (3 mg/kg, i.p.) and the other 3 with saline (1 ml/kg), twice daily (800 and 1800 h). Four hours following the morning injection on Day 4 and 6, the oxycodone treated rats were challenged with saline and immediately confined in one side compartment of the conditioning box for 30 min, while on Day 5 and 7, they were first pretreated with either vehicle or 1 of 2 doses of compound (±)-29 (5 and 15 mg/kg, i.p.) 3 h after morning oxycodone injection, and 1 h later, challenged with naloxone (1 mg/kg, i.p.). The rats were then immediately confined in the other side compartment for 30 min. The side compartments for saline or naloxone conditioning were counterbalanced in each group. Place conditioning procedures for chronically saline treated groups were the same as for oxycodone treated groups on Day 4 and 6, but on Day 5 and 7, these 3 groups were challenged with either naloxone, vehicle or compound (±)-29 (15 mg/kg) at the same time point assigned for oxycodone treated groups (FIG. 4A). Twenty-four hours after the last conditioning session, the animals were each placed in the same apparatus and allowed to explore the apparatus for an additional 15 min. The time that animals spent in each compartment was recorded. The CPA score was calculated as the time difference (seconds) that animal spent in drug-paired versus saline-paired compartment.

Experiment 6: Effects of Compound (W)-29 on Sucrose Self-Administration.

The procedures for oral sucrose self-administration were identical to those for oxycodone self-administration, except that active lever presses led to delivery of 0.08 ml of 5% sucrose solution into a liquid food tray on the operant chamber wall, and surgery was not performed. Seven rats were involved in sucrose self-administration training and testing. Sucrose deliveries per session were capped at 100. Following completion of training, the animals were tested 3 times, with pretreatment by vehicle and 2 doses of compound (±)-29 (15 and 25 mg/kg, i.p.). The 3 tests in each rat were counterbalanced and were separated by 2 additional training sessions between each 2 tests.

Experiment 7: Effects of Compound (±)-29 on Oxycodone-Induced Antinociceptive Response.

Nociceptive tests were performed using a hot plate device (Model 39, IITC Life Science Inc., Woodland Hills, CA, USA). The rat was put inside a transparent cage on the hot plate (52±0.2° C.). When thermal nociceptive signs such as licking, stomping the hind paw, or jumping from the plate appeared, the rat was immediately removed from the cage. The time interval (sec) from rat being placed on the hotplate to exhibiting the first sign of thermal nociception was measured. The cut-off time for the test was 60 s to avoid tissue damage.

These experiments involved 8 groups of rats (n=8-9/group) in 2 series of repeated testing: 4 groups were used to test the effects of compound (±)-29 pretreatment on the time course of antinociception induced by oxycodone at a single dose, and another 4 groups were used to test the effects of compound (±)-29 pretreatment on the antinociception induced by various oxycodone doses. Each rat was first habituated to the testing environment for 1 h, followed by placement on the hot plate without treatment to obtain baseline response latencies. The groups in the time course test received baseline testing. Then, group 1 was pretreated with vehicle, and the other 3 groups were pretreated with a dose of compound (±)-29 (5, 15 or 25 mg/kg, i.p.). Fifteen min following the pretreatment, each rat was challenged with a saline injection (1 ml/kg) and, 30 min later, tested for the second time on the hot plate. On the next day, each group received the same pretreatment as on day 1, but challenged with oxycodone (2 mg/kg, i.p.), and each rat was then tested again at 30-, 60- and 120-min following oxycodone challenge. For the oxycodone dose-response curve determination, the animals were tested for 4 days, with the same pretreatment regimen on each day, but challenged with an ascending dose of oxycodone (0.5, 1, 2, and 4 mg/kg, for day 1, 2, 3 and 4, respectively). The hot plate test was conducted 30 min following an oxycodone challenge on each day. Data were calculated as % of maximum percentage effect (% MPE) using the formula: (treatment value−basal value)/(cutoff value−basal value)×100. The dose of oxycodone and the time point for the hot plate test were chosen based on reported studies indicating that the peak effects of oxycodone appeared approximately 30 min following injection, and the oxycodone dose range covered the effective dose range in rats (Lemberg et al, 2006; Poyhia and Kalso, 1992).

Chromatographic analysis was performed using an Accela™ ultra high-performance system consisting of an analytical pump, and an autosampler coupled with TSQ Vantage mass spectrometer (Thermo Fisher Scientific Inc., Waltham MA). Separation of the analyte was achieved at ambient temperature using the Agilent Eclipse Plus column (100×2.1 mm i.d.) packed with a 1.8 μm $C_{18}$ stationary phase. The mobile phase was composed of 0.1% formic acid in acetonitrile and 0.1% formic acid in $H_2O$ with gradient elution. The total run time for each analyte was 4.5 min. The $[M+H]^+$ ion transitions of compound (±)-29 (m/z 143.930, 213.003) and the internal standard (m/z 423.03>180.086, 207.086).

Active Agents

Compound (±)-29 [(±)-N-(4-(4-(3-Chloro-5-ethyl-2-methoxyphenyl)piperazin-1-yl)-3-hydroxybutyl)-1H-indole-2-carboxamide]. Oxycodone HCl, sucrose and 2-hydroxypropyl-β-cyclodextrin were purchased from Sigma/RBI (St Louis, MO, USA). Oxycodone was dissolved in physiological saline for either i.v. infusions or i.p. injections. 2-hydroxypropyl-β-cyclodextrin was dissolved in water to a concentration of 25% and used as a vehicle for compound (±)-29.

Data Analyses

All behavioral data are presented as means±SEM. One-way or two-way analysis of variance (ANOVA) for repeated measures over time was used to analyze the data across experiments. Post-ANOVA multiple comparisons were carried out using the Newman-Keuls test. $P<0.05$ was considered to indicate statistical significance.

Results

Compound (±)-29 Pretreatment Blocks the Acquisition of Oxycodone Self-Administration FIG. 1 shows mean (±S.E.) oxycodone infusions (FIG. 1A) and active lever presses (FIG. 1B) across self-administration sessions in three groups of rats pretreated with vehicle, 5 mg/kg or 15 mg/kg compound (±)-29 during the initial five sessions. Pretreatment with compound (±)-29 dose-dependently decreased the number of oxycodone infusions and active lever presses across the five compound (±)-29-pretreatment sessions. After termination of compound (±)-29 pretreatment, the rats' responses for oxycodone infusions on the active lever remained significantly lower in the compound (±)-29 treatment groups during the following three sessions (session 6-8, and gradually increased to approximately the same levels seen in the vehicle group. Two-way ANOVA for repeated measures over sessions revealed significant compound (±)-29 treatment main effects (A, $F_{2,21}$=10.59, P<0.001; B, $F_{2,21}$=10.22, P<0.001) and time main effects (A: $F_{10,210}$=5.48, P<0.0001; B: $F_{10,210}$=4.39, P<0.0001). Pretreatment with compound (±)-29 showed no effects on the rats' responses on the inactive lever (data not shown) suggesting that their general behavior was not disrupted.

Figure 1C:
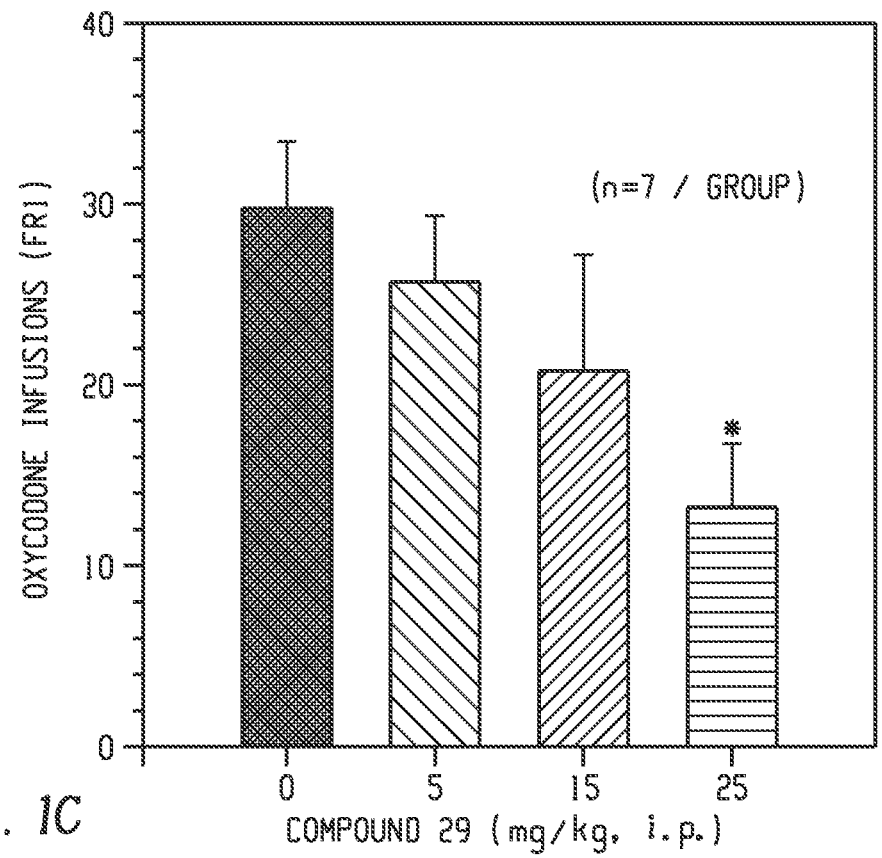
Figure 1D:
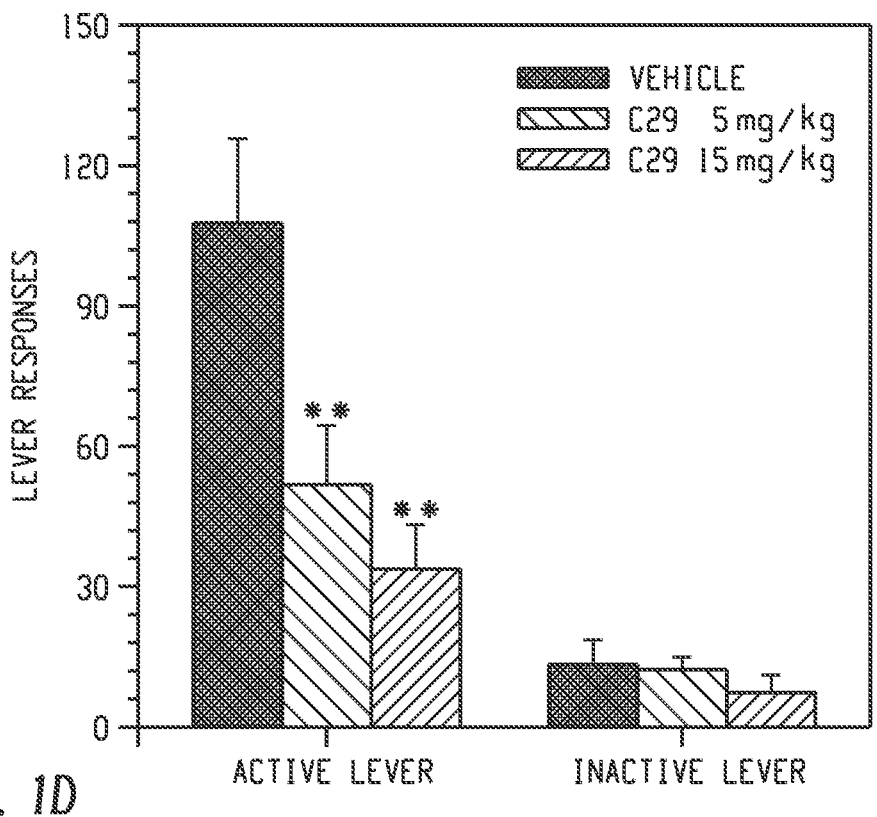

Compound (±)-29 Inhibits the Maintenance of Oxycodone Self-Administration and Oxycodone-Seeking when Oxycodone was Replaced by Saline In additional groups of rats trained to self-administer oxycodone, compound (±)-29 pretreatment (5-25 mg/kg, i.p.) dose-dependently decreased oxycodone infusions during the maintenance of self-administration compared to either the last training session or vehicle pretreated group (FIG. 1C). One-way ANOVA (FIG. 1C) revealed a significant group difference ($F_{3,21}$=5.49, P<0.01). Post-hoc analysis indicated that oxycodone infusions in the 25 mg/kg compound (±)-29 group were significantly lower than in the vehicle group (FIG. 1C). When saline was substituted for oxycodone during self-administration in a test session, compound (±)-29 pretreatment (5 or 15 mg/kg, i.p.) dose-dependently inhibited oxycodone-seeking behavior (i.e., extinction responding) as demonstrated by the selective decreases in the rats' responding on the active lever as opposed to the inactive lever (FIG. 1D). Two-way ANOVA revealed a significant group×lever interaction ($F_{2,40}$=17.86, P<0.001).

Figure 1E:
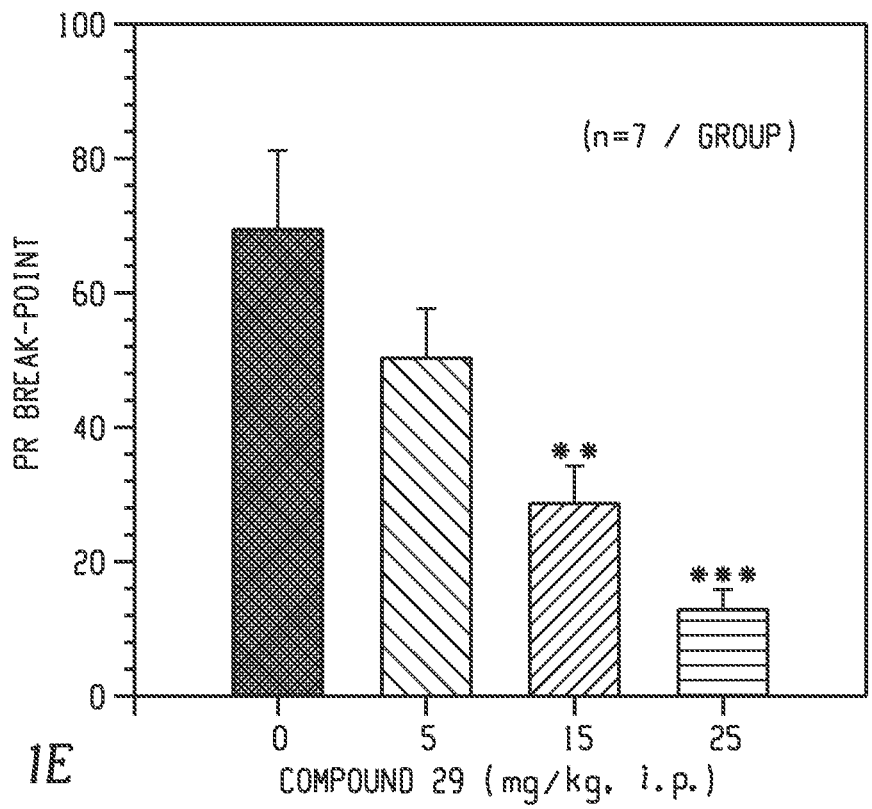

Compound (W)-29 Pretreatment Lowers the Break-Point for Oxycodone Self-Administration Under Progressive-Ratio Reinforcement To determine whether blockade of D3R alters motivation to seek oxycodone, oxycodone self-administration under progressive-ratio (PR) reinforcement was used to examine the effects of compound (±)-29 on the break-point, an index of reward strength (Xi et al., 2005), in an additional 4 groups of rats (n=7/group). FIG. 1E shows that systemic administration of compound (±)-29 significantly and dose-dependently lowers the break-point for oxycodone self-administration ($F_{3,18}$=11.07, p<0.001), suggesting reduced oxycodone reward after D3R blockade.

Compound (±)-29 does not Reduce Sucrose Self-Administration

Figure 1F:
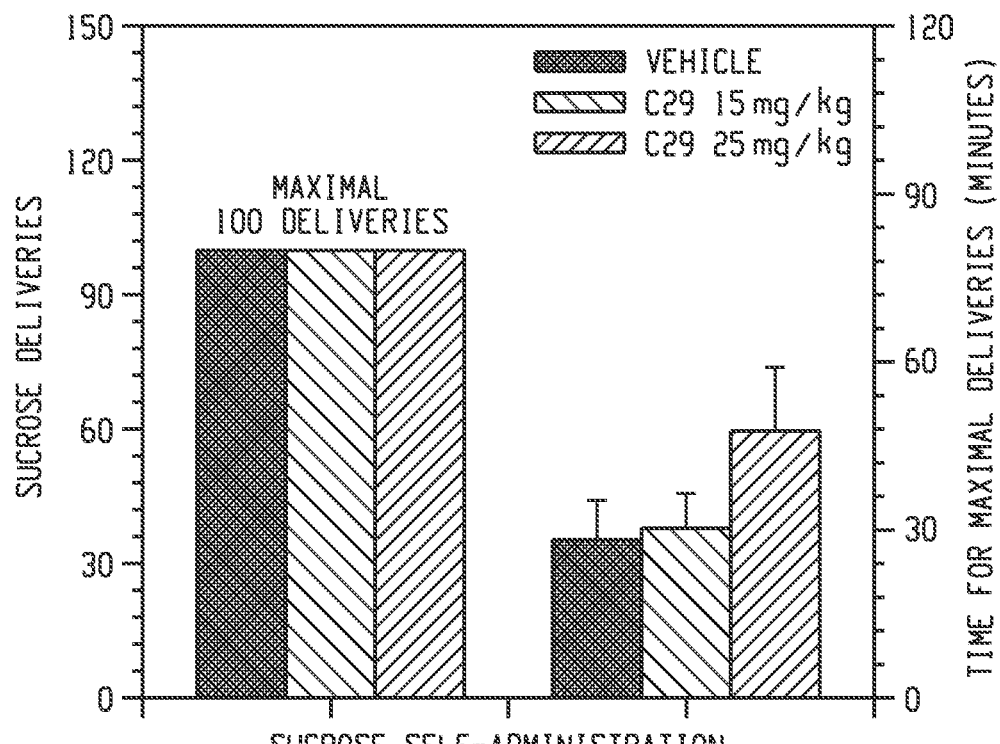

In contrast to the above, pretreatment with compound (±)-29 (15-25 mg/kg, i.p.) did not significantly alter sucrose self-administration (FIG. 1F). All rats reached the maximal allowed sucrose deliveries (100) in the 3 test sessions (FIG. 1F, left panel), while the time required to reach the maximal deliveries was significantly longer after compound (±)-29 administration compared to the vehicle control group (FIG. 1F, right panel, $F_{2,12}$=5.09, P<0.05).

Compound (±)-29 Blocks the Reinstatement of Oxycodone-Seeking Behavior

Figure 2A:
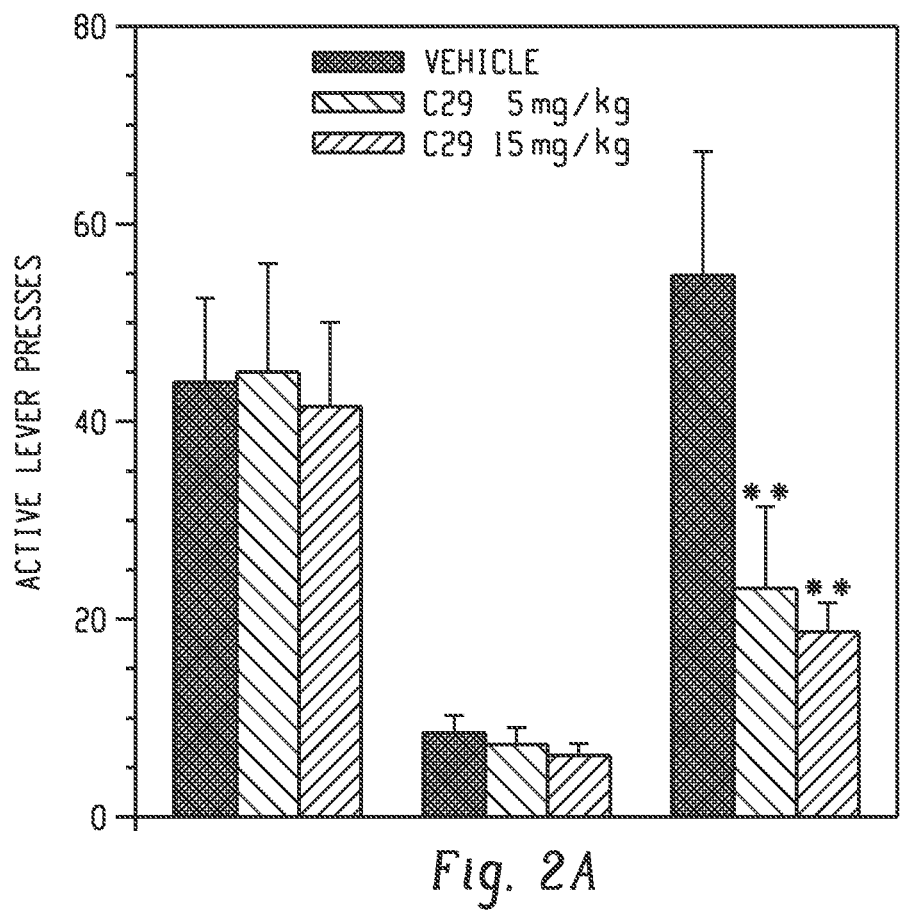
FIGS. 2A and 2B shows the mean±SE responses of animal groups on the active (FIG. 2A) and inactive (FIG. 2B) levers during the last oxycodone self-administration, the last extinction training sessions, and during the reinstatement test session where (±)-29 dose dependently reduced reinstatement to oxycodone seeking.
Figure 2B:
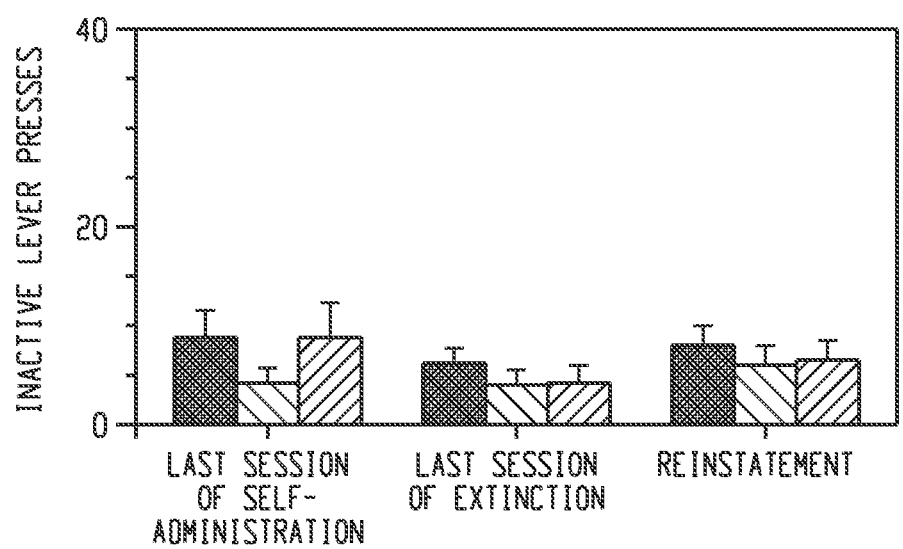

FIGS. 2A and 2B show the mean±SE responses of animal groups on the active and inactive levers during the last oxycodone self-administration, the last extinction training sessions, and during the reinstatement test session. Neither active (FIG. 2A) or inactive (FIG. 2B) lever-presses during the last self-administration session or during the last extinction session were different across treatment groups. Systemic injection of oxycodone (1 mg/kg, i.p.) robustly reinstated active lever-presses in the vehicle pretreated group, and such reinstatement was dose-dependently blocked in compound (±)-29 pretreated (5-15 mg/kg, i.p.) groups. Two-way ANOVA for repeated measures revealed a significant group×time interaction ($F_{3,38}$=4.38, P<0.02). Oxycodone injection and compound (±)-29 pretreatment showed no effects on the rats' inactive lever-presses ($F_{3,38}$=0.38, P=0.82).

Compound (±)-29 does not Diminish Oxycodone's Antinociceptive Effects in Rats

Figure 3A:
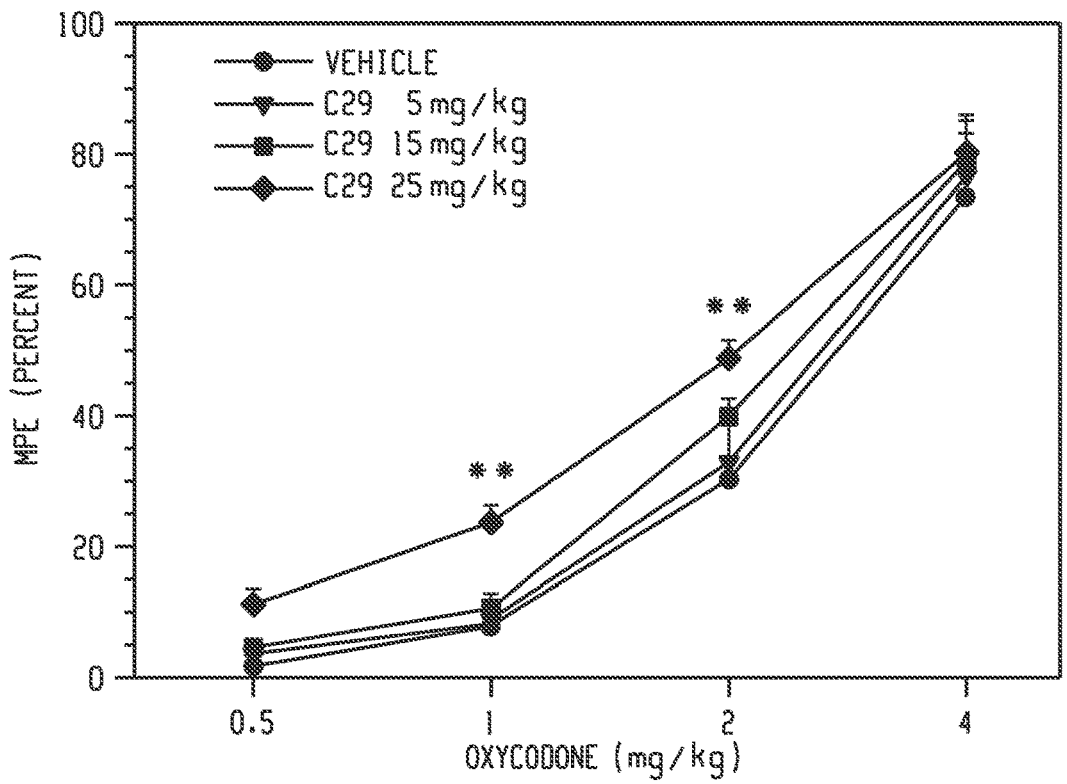
FIGS. 3A and 3B: Effects of compound (±)-29 on the anti-nociceptive effects of oxycodone in rats.
Figure 3B:
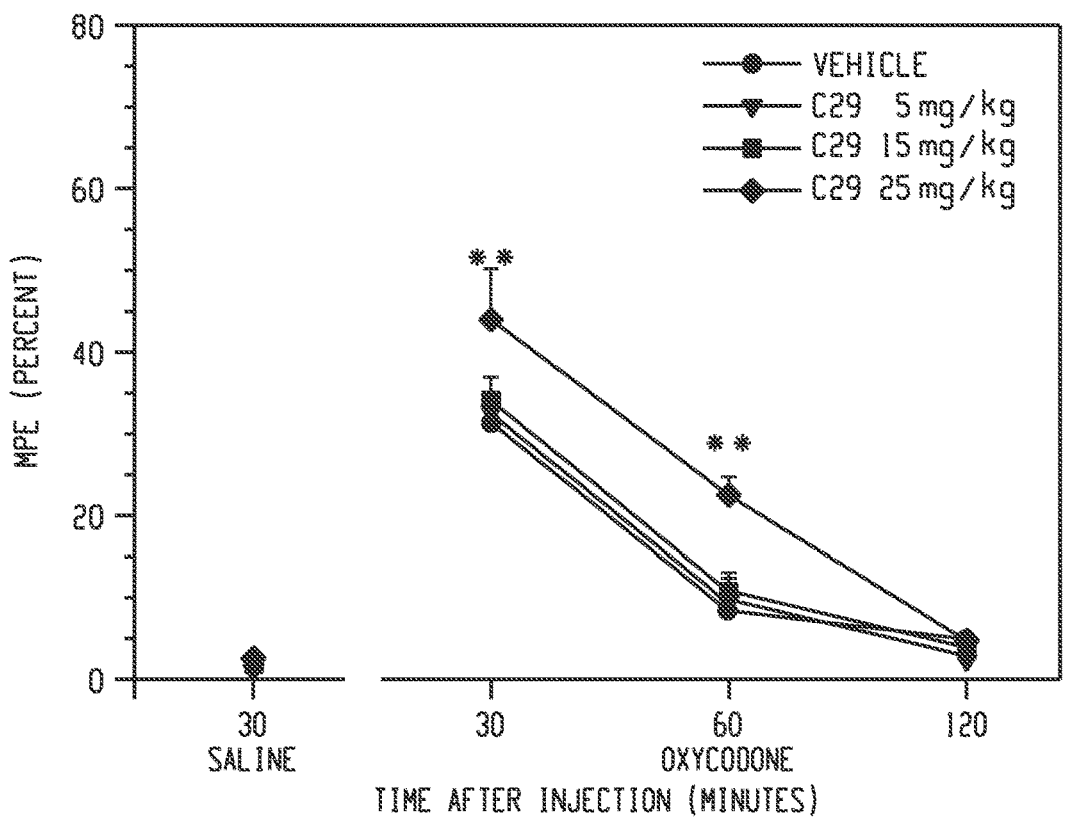

Baseline nociceptive response latencies ranged from 7.89±0.061 to 8.48±0.60 across all treatment groups with no significant differences among the groups. FIG. 3A shows the effects of compound (±)-29 pretreatment on the dose-response curve of oxycodone. Two-way ANOVA revealed significant effects of group (compound (±)-29 treatment) ($F_{3,25}$=3.85, P<0.05), oxycodone dose ($F_{3,75}$=230.62, P<0.0001), but no effect on group×time interaction ($F_{9,75}$=0.46, P=0.89). Post-hoc analysis indicated a significant elevation of MPE % in the 25 mg/kg pretreatment group (versus vehicle group) tested following 1 but not 0.5 or 4 mg/kg oxycodone. FIG. 3B shows the effects of compound (±)-29 (5-25 mg/kg, i.p.) pretreatment on the nociceptive responses induced by saline, and by 2 mg/kg of oxycodone. Saline administration did not significantly affect the rats' nociceptive responses compared to their basal levels and compound (±)-29 pretreatment showed no effects on saline-induced nociceptive responses. Oxycodone administration (filled circles) in the vehicle pretreated group significantly increased % MPE 30 min following drug administration, and such effects declined rapidly following 60 and 120 min of drug administration. Two-way ANOVA revealed significant effects of group (treatment) ($F_{3,26}$=3.60, P<0.05), and time ($F_{2,52}$=156.71, P<0.0001), but not group×time interaction ($F_{6,52}$=1.50, P=0.20).

Compound (±)-29 Inhibits Naloxone-Precipitated Conditioned Place Aversion

Figure 4B:
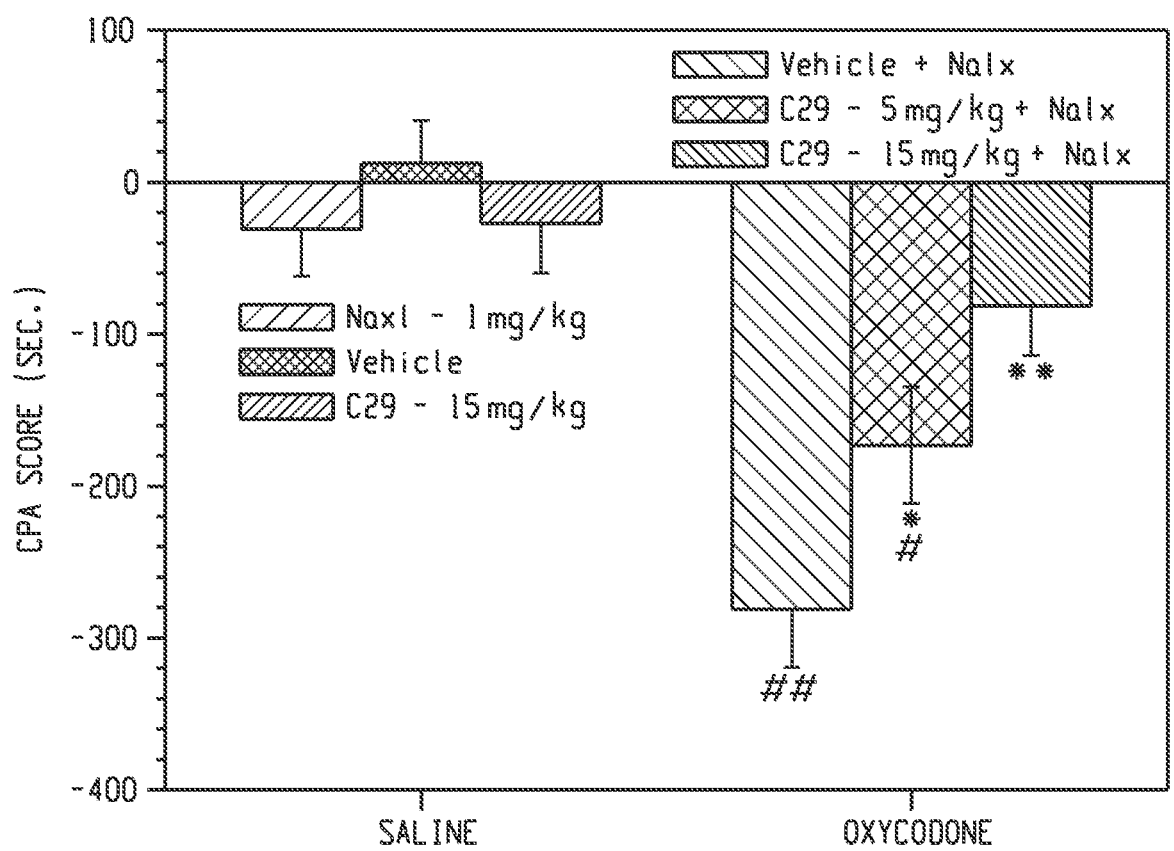

FIG. 4A shows the experimental procedure. In the chronically saline-treated groups, conditioning of rats with either naloxone, compound (±)-29 or vehicle alone produced neither CPP or CPA (FIG. 4B, left panel). In rats chronically treated with 3 mg/kg oxycodone, after 2 conditioning sessions, naloxone induced a significant CPA in the vehicle-pretreated rats (FIG. 4B, right panel). Compound (±)-29 (5 or 15 mg/kg, i.p., 1 h before naloxone conditioning) dose-dependently attenuated the CPA induced by naloxone compared to the vehicle control group. Two-way ANOVA of CPA scores revealed significant effects of treatment ($F_{1,42}$=35.60, P<0.0001; saline versus oxycodone), conditioning ($F_{2,42}$=5.12, P<0.02) and treatment×conditioning interaction ($F_{2,42}$=4.53, P<0.02). Post-hoc analysis indicated that the CPA score in the 15 mg/kg compound (±)-29 pretreated group was not significantly different to any groups that were chronically treated with saline.

Compound (±)-29 was found to be a highly selective and metabolically stable D3R antagonist across species, dose-dependently attenuated acquisition and maintenance of oxycodone self-administration, lowered the progressive-ratio break-point for oxycodone self-administration, and blocked oxycodone seeking in rats following extinction of self-administration. These findings suggest that compound (±)-29 is capable of reducing the reinforcing effects of oxycodone. These effects of compound (±)-29 are unlikely to have been the consequence of its effects on general motor function since compound (±)-29 nether significantly affected inactive lever-presses tested under any condition in the present study or basal locomotor activity tested in mice in the study below. Moreover, compound (±)-29 at doses effective in attenuating oxycodone self-administration did not significantly affect sucrose self-administration. In fact, most sucrose self-administering rats pretreated with compound (±)-29 were able to reach the capped number of sucrose deliveries in approximately 1 h, a response rate markedly higher than that seen for oxycodone self-administration in the vehicle pretreated group. Not wishing to be bound by theory, the effects of compound (±)-29 on oxycodone self-administration and on oxycodone seeking seen in this study are likely attributable to its selective inhibition of oxycodone-induced reinforcement, via D3R blockade.

Importantly, compound (±)-29 does not compromise the antinociceptive effects of oxycodone tested in the hot plate assay, at doses that effectively blocked acquisition of oxycodone self-administration. Indeed, at the highest dose tested (25 mg/kg), compound (±)-29 potentiated the antinociceptive effects of oxycodone in rats. This finding is consistent with the D3R antagonist SB-277011A significantly inhibiting opioid-induced conditioned place preference (Ashby et al, 2003) and deletion of D3R in D3-KO mice attenuating morphine-induced anti-nociception (Brewer et al, 2014; Li et al, 2012). The involvement of D3R antagonism in acquisition of opioid self-administration and in opioid analgesia has not been systematically examined prior to the present study.

Avoidance of the development of dependence during medically mandated prescription opioid use remains a continuous challenge clinically. It has been shown that ultra-low-dose naltrexone as a co-treatment with oxycodone can enhance oxycodone-induced analgesia while significantly reducing oxycodone's addictive liability (Leri and Burns, 2005; Webster et al, 2006), and genetic disruption of the endocannabinoid system has been shown to block CPP to morphine without significantly impacting its analgesic effects (Ledent et al, 1999). These findings indicate neurocircuits that mediate reward and pain sensation may be dissociated to a certain extent, and can be selectively targeted. Not wishing to be bound by theory, the present findings suggest that dopamine transmission at D3R may also be a neuronal element with promise for treatment targeting. Chronic administration of morphine is associated with increased D3R mRNA expression in dopaminergic brain regions, suggesting an increased D3R activity in opioid dependence (Spangler et al, 2003). Compound (±)-29 also significantly inhibits acquisition of both oxycodone-induced locomotor sensitization and CPP. Thus, D3R antagonist treatment may be an effective add-on medication to reduce the abuse liability of prescription opioids, particularly in those patients with high vulnerability to develop dependence.

The present study indicates that compound (±)-29 also inhibits the aversive or stress-like state induced by naloxone-precipitated withdrawal. Aversive or stress-like states arising from drug withdrawal are considered to be major factors that drive compulsive drug taking and seeking in drug dependence (Koob and Mason, 2016; Koob and Volkow, 2016). It was found that compound (±)-29, similar to SB277011A (Rice et al, 2012), significantly blocked CPA induced by naloxone-precipitated withdrawal at the doses effectively inhibiting oxycodone self-administration and oxycodone seeking. These doses of compound (±)-29 also effectively blocked reinstatement of oxycodone seeking trigged by oxycodone in rats trained to self-administer oxycodone and subsequently behaviorally extinguished. Hence, compound (±)-29 is a highly potent and selective D3R antagonist with a stable metabolic profile across species. Its metabolic stability distinguishes compound (±)-29 from many previously described D3R ligands, suggesting high translational potential (Keck et al, 2015). The findings indicate that compound (±)-29 may be a promising pharmacotherapeutic agent for treating opioid dependence at various stages, including prevention at initial use, and detoxification and relapse treatment.

REFERENCES

Ashby C R, Jr., Paul M, Gardner E L, Heidbreder C A, Hagan J J (2003). Acute administration of the selective D3 receptor antagonist SB-277011A blocks the acquisition and expression of the conditioned place preference response to heroin in male rats. *Synapse* 48(3): 154-156.

Brewer K L, Baran C A, Whitfield B R, Jensen A M, Clemens S (2014). Dopamine D3 receptor dysfunction prevents anti-nociceptive effects of morphine in the spinal cord. *Front Neural Circuits* 8: 62-64.

Keck T M, John W S, Czoty P W, Nader M A, Newman A H (2015). Identifying Medication Targets for Psychostimulant Addiction: Unraveling the Dopamine D3 Receptor Hypothesis. *J Med Chem* 58(14): 5361-5380.

Koob G F, Mason B J (2016). Existing and Future Drugs for the Treatment of the Dark Side of Addiction. *Annu Rev Pharmacol Toxicol* 56: 299-322.

Koob G F, Volkow N D (2016). Neurobiology of addiction: a neurocircuitry analysis. *Lancet Psychiatry* 3(8): 760-773.

Ledent C, Valverde O, Cossu G, Petitet F, Aubert J F, Beslot F, et al (1999). Unresponsiveness to cannabinoids and reduced addictive effects of opiates in CB1 receptor knockout mice. *Science* 283(5400): 401-404.

Lemberg K, Kontinen V K, Viljakka K, Kylanlahti I, Yli-Kauhaluoma J, Kalso E (2006). Morphine, oxycodone, methadone and its enantiomers in different models of nociception in the rat. *Anesth Analg* 102(6): 1768-1774.

Leri F, Burns L H (2005). Ultra-low-dose naltrexone reduces the rewarding potency of oxycodone and relapse vulnerability in rats. *Pharmacol Biochem Behav* 82(2): 252-262.

Li T, Hou Y, Cao W, Yan C X, Chen T, Li S B (2012). Role of dopamine D3 receptors in basal nociception regulation and in morphine-induced tolerance and withdrawal. *Brain Res* 1433: 80-84.

Poyhia R, Kalso E A (1992). Antinociceptive effects and central nervous system depression caused by oxycodone and morphine in rats. *Pharmacol Toxicol* 70(2): 125-130.

Rice O V, Gardner E L, Heidbreder C A, Ashby C R, Jr. (2012). The acute administration of the selective dopamine D(3) receptor antagonist SB-277011A reverses conditioned place aversion produced by naloxone precipitated withdrawal from acute morphine administration in rats. *Synapse* 66(1): 85-87.

Spangler R, Goddard N L, Avena N M, Hoebel B G, Leibowitz S F (2003). Elevated D3 dopamine receptor mRNA in dopaminergic and dopaminoceptive regions of the rat brain in response to morphine. *Brain Res Mol Brain Res* 111(1-2): 74-83.

Webster L R, Butera P G, Moran L V, Wu N, Burns L H, Friedmann N (2006). Oxytrex minimizes physical dependence while providing effective analgesia: a randomized controlled trial in low back pain. *J Pain* 7(12): 937-946.

Xi Z X, Gilbert J G, Pak A C, Ashby C R, Jr., Heidbreder C A, Gardner E L (2005). Selective dopamine D3 receptor antagonism by SB-277011A attenuates cocaine reinforcement as assessed by progressive-ratio and variable-cost-variable-payoff fixed-ratio cocaine self-administration in rats. *Eur J Neurosci* 21(12): 3427-3438.

You Z B, Gao J T, Bi G H, He Y, Boateng C, Cao J, et al (2017). The novel dopamine D3 receptor antagonists/ partial agonists CAB2-015 and BAK4-54 inhibit oxycodone-taking and oxycodone-seeking behavior in rats. *Neuropharmacology* 126: 190-199.

Tables 2a, 2b, 3a. and 3b provide additional functional data for selected compounds of Formula (I).

TABLE 2a

Functional data for selected compounds of Formula (I) using stimulation or inhibition of quinpirole-stimulated mitogenesis in CHO cells with human dopamine D3R[a]

| | D$_3$R mitogenesis assay | | |
|---|---|---|---|
| Compd | Agonist EC$_{50}$ ± SEM, nM | % Stimulation | Antagonist IC$_{50}$ ± SEM, nM |
| 18 | 4.70 ± 0.57 | 42.3 | 19.1 ± 3.5 |
| 19 | 2.58 ± 0.87 | 17.9 | 50.5 ± 7.2 |
| 20 | 410 ± 130 | 31.2 | 18.5 ± 6.3 |
| 21 | 196 ± 64 | 22.3 | 230 ± 27 |
| 28 | >8300 | 5.8 | 330 ± 100 |
| 29 | >8300 | 6.7 | 360 ± 100 |
| 30 | >6600 | 4.9 | 420 ± 130 |
| 31 | >7100 | 3.6 | 950 ± 350 |

[a]Data were obtained through the NIDA Addiction Treatment Discovery Program contract (ADA151001) with Oregon Health & Science University.
[b]ND = Not determined; Functional assays for each receptor was not conducted if the K$_i$ value for the binding assay is >500 nM for DA receptors.

TABLE 2b

Functional data for selected compounds using stimulation or inhibition of quinpirole-stimulated mitogenesis in CHO cells with human dopamine D$_3$R[a]

| Compound | Agonist EC$_{50}$ ± S.E.M., nM | % Stimulation | Antagonist IC$_{50}$ ± S.E.M., nM |
|---|---|---|---|
| C4a | >5400 | 2.7 | 510 ± 130 |
| C5a | >6800 | 5.4 | 95 ± 31 |
| C4b | >4000 | 5.1 | 490 ± 150 |
| C5b | >7500 | 15.5 | 450 ± 160 |
| (R)-29 | >3200 | 17.7 | 350 ± 110 |
| (S)-29 | >6800 | 17.0 | 1020 ± 200 |
| (R)-19 | >2200 | 20.2 | 18.7 ± 6.6 |
| (S)-19 | 46 ± 17 | 25.9 | 660 ± 260 |

[a]Data were obtained through the NIDA Addiction Treatment Discovery Program contract (ADA12013) with Oregon Health & Science University.

The in vitro functional efficacies of a subset of 3-F-analogues C4a,C5a and C4b,C5b and R- and S-enantiomers of both 29 and 19 were examined for stimulation or inhibition of quinpirole-stimulated mitogenesis in CHO cells (Table 2b). These data revealed that all the 3-F analogues were D$_3$R antagonists, as were (R)- and (S)-29 and (R)-19. However, (S)-19 was a relatively low efficacy partial agonist, like (±)-19.

TABLE 3a

Additional in vitro binding and functional data for selected compounds of Formula (I) at 5HT$_{1A}$, 5HT$_{2A}$ and 5HT$_{2C}$ receptors[a]

| | 5-HT$_{1A}$ [$^3$H]-8-OH-DPAT K$_i$ ± SEM, nM | 5-HT$_{2A}$ [$^{125}$I]DOI K$_i$ ± SEM, nM | 5-HT$_{2C}$ [$^{125}$I]DOI K$_i$ ± SEM, nM | 5HT$_{1A}$ [$^{35}$S]GTPγS binding | |
|---|---|---|---|---|---|
| Compd | | | | Agonist EC$_{50}$ ± SEM, nM | % Stimulation |
| 18 | 59 ± 13 | 5.22 ± 0.98 | 18.3 ± 2.2 | 149 ± 47 | 94.3 |
| 19 | 880 ± 160 | 28.1 ± 9.7 | 113 ± 33 | ND[b] | — |
| 20 | 26.0 ± 8.1 | 2.41 ± 0.82 | 18.7 ± 4.5 | 31 ± 10 | 99.4 |
| 21 | 27.6 ± 5.3 | 3.2 ± 1.1 | 89 ± 22 | 118 ± 39 | 101.1 |
| 28 | 2330 ± 700 | 60.1 ± 9.5 | 144 ± 37 | ND[b] | — |
| 29 | >7600 | 188 ± 22 | 2190 ± 460 | ND[b] | — |
| 30 | 560 ± 170 | 25.0 ± 6.6 | 55 ± 17 | ND[b] | — |
| 31 | 2410 ± 830 | 42.9 ± 6.8 | 268 ± 34 | ND[b] | — |

[a]Data were obtained through the NIDA Addiction Treatment Discovery Program contract (ADA151001) with Oregon Health & Science University.
[b]ND = Not determined; Functional assays for each receptor was not conducted if the K$_i$ value for the binding assay was >250 nM for 5-HT receptors.

TABLE 3b

In vitro binding and functional data for selected compounds at 5-HT$_{1A}$, 5-HT$_{2A}$ and 5-HT$_{2C}$ receptors[a]

| | 5-HT$_{1A}$ [$^3$H]-8-OH-DPAT K$_i$ ± SEM, nM | 5-HT$_{2A}$ [$^{125}$I]DOI K$_i$ ± SEM, nM | 5-HT$_{2C}$ [$^{125}$I]DOI K$_i$ ± SEM, nM | 5HT$_{1A}$ [$^{35}$S]GTPγS binding | |
|---|---|---|---|---|---|
| Compound | | | | Agonist EC$_{50}$ ± SEM, nM | % Stimulation |
| C4a | 9500 ± 3000 | 6600 ± 1400 | >8900 | ND[b] | — |
| C5a | 910 ± 120 | 620 ± 120 | 580 ± 160 | ND[b] | — |
| C4b | 2660 ± 570 | 2990 ± 530 | 1780 ± 390 | ND[b] | — |
| C5b | 117 ± 14 | 336 ± 19 | 464 ± 36 | 351 ± 84 | 43 |
| (R)-29 | 2800 ± 340 | 1933 ± 20 | 1260 ± 320 | ND[b] | — |
| (S)-29 | 4980 ± 270 | 7600 ± 1800 | 5670 ± 930 | ND[b] | — |
| (R)-19 | 248 ± 18 | 21.3 ± 6.6 | 50 ± 13 | 1050 ± 260 | 74 |
| (S)-19 | 131 ± 12 | 940 ± 130 | 1110 ± 360 | 2060 ± 580 | 69 |

[a]Data were obtained through the NIDA Addiction Treatment Discovery Program contract (ADA12013) with Oregon Health & Science University.
[b]ND = Not determined; Functional assays for each receptor was not conducted if the K$_i$ value for the binding assay was >250 nM for 5-HT receptors.

As depicted in Table 3b, none of these analogues showed high affinity binding to any of the 5-HT receptor subtypes tested compared to their D$_3$R affinities. Compound C5b showed the highest affinities of the 3-F analogues, across the 5-HT receptor subtypes, and was a low potency partial agonist at 5HT$_{1A}$ (EC$_{50}$=351 nM). (R)- and (S)-19 showed higher affinities across the 5-HT receptor subtypes than (R)- and (S)-29, however selectivities for D$_3$R remained high ((R)-29, 5-HT$_{1A}$/D$_3$R=469, 5-HT$_{2A}$/D$_3$R=324, 5-HT$_{2C}$/D$_3$R=211, and (S)-29, 5-HT$_{1A}$/D$_3$R=149, 5-HT$_{2A}$/D$_3$R=228, 5-HT$_{2C}$/D$_3$R=170).

Example 5. Methods for Pharmacokinetics Study of Novel Dopamine D3 Receptor Antagonists in Rats Male Long-Evans rats with body weights ~250 grams (Charles River Laboratories, Raleigh, NC, USA) were used in this study. All rats were housed individually in a climate-controlled room under a 12 h light/dark cycle. Food and water were available ad libitum throughout the experiments. All experimental procedures were conducted in accordance with the Guide for the Care and Use of Laboratory Animals and were approved by the Animal Care and Use Committee of the National Institute on Drug Abuse of the U.S. National Institutes of Health.

Experimental (oral gavage) procedures: The animals were gently restrained (grasp the animal by the loose skin of the neck and back) to immobilize the head but not such that the animals vocalize or show other signs of distress. Maintained the animal in an upright (vertical) position and passed the gavage needle (19-gauge) along the side of the mouth. Following the roof of the mouth, advanced the needle into the esophagus and toward the stomach. After the needle was passed to the correct length, the compound was injected. Then, the animals were deeply anesthetized with 100 mg/kg pentobarbital (i.p.), and then blood (~1 ml) was obtained via cardiac puncture and brain was dissected at different time points (15 min, 30 min, 60 min, 2 h, 4 h, and 8 h, n=3 rats per time point) after oral drug administration. Three additional rats received the vehicle (25% beta-hydroxy-cyclo-dextrin) as a "0 min" time point controls (i.e., baseline before the drug injection, in which the drug levels in the samples should be zero).

Sample analysis method; Preparation of standard and internal standard (IS) stock solution: Test compounds (R- and S-29 and R- and S-19) were dissolved in appropriate amount of DMSO to yield a 10 mM stock solution. These solutions were stored at −20° C. Losartan (IS) was dissolved in DMSO at 10 mM concentration that was further diluted in acetonitrile to obtain a final concentration of 500 nM and the solutions were stored at −20° C.

Standard Curve and Quality Control (QC) Sample Preparation: Standard curve plasma samples were prepared using naïve rat plasma, by serial dilution of the stock solution, with 8 standards and 4 QCs, ranging from 10-50,000 pmol/mL.

Standard curve brain samples were prepared using naïve rat brain. The tissue was homogenized in acetonitrile (Dilution Factor; DF=3), crushed, and centrifuged at 10,000 rpm for 10 minutes. The resulting supernatant was used as the standard curve matrix. The standard curve was subsequently prepared by serial dilution of the stock solution, with 7 standards and 4 QCs, ranging from 30-50000 pmol/mL.

Extraction Procedure: Test compounds were extracted from plasma samples by protein precipitation using acetonitrile. Compounds were extracted from brain samples by placing weighed tissue into 2 times w/v of acetonitrile (DF=3), crushed, centrifuged at 10,000 rpm for 10 minutes, and the resultant supernatant was used as the sample solution. Briefly standards, QCs, and samples (25 µL) were mixed with 100 µL acetonitrile containing 0.5 µM Losartan (internal standard; IS) in low retention microcentrifuge tubes. The mixture was vortexed for 1 min and centrifuged at 10,000 rpm for 10 min at 5° C. 50 µL of supernatant was transferred to a 250 µL polypropylene autosampler vials and mixed with 50 µL water, and sealed with a Teflon cap. A volume of 3 µL was injected onto the ultra-performance liquid chromatography (UPLC) instrument for quantitative analysis using a temperature-controlled autosampler operating at 10° C.

Chromatographic and Mass Spectrometric Conditions:
LC Conditions
UHPLC System: Accela pump 1250 and Accela open-arm autosampler AS
Column: Eclipse Plus C18 RRHD 1.8 um, 2.1×100 mm
Flow rate: 0.4 mL/min
Mobile Phase A: 0.1% FA in ACN, Phase B: 0.1% FA in water.
LC Gradient Condition

| Time (min) | Phase A(%) | Phase B(%) |
|---|---|---|
| 0.01 | 10 | 90 |
| 0.20 | 10 | 90 |
| 2.00 | 99 | 1 |

-continued

| Time (min) | Phase A(%) | Phase B(%) |
|---|---|---|
| 2.50 | 99 | 1 |
| 2.70 | 10 | 90 |
| 5.00 | 10 | 90 |

MS Condition

| Ionization Mode | ESI, MRM(+) | | | |
|---|---|---|---|---|
| Compound | Q1 | Q3 | CE | S-Lens |
| 29 | 485.146 | 143.930, 213.003 | 34, 23 | 139 |
| 19 | 454.827 | 143.864 | 31 | 127 |
| Losartan | 423.200 | 180.088, 207.107 | 35, 22 | 99 |

The mass spectrometer was operated with an ESI interface in positive ionization mode for all compounds tested and controlled by the Xcalibur software 2.3 (Thermo Scientific). Samples were introduced to the interface through Turbo Ion Spray with the capillary temperature setting at 350° C. Nitrogen was used as the sheath and auxiliary gas, and argon as a collision gas with the settings of 40, 5 and 1.4, respectively. Quantification was performed in multiple-reaction monitoring (MRM) mode.

Chromatographic analysis was performed using an Accela™ ultra high-performance system consisting of an analytical pump, and an autosampler coupled with TSQ Vantage mass spectrometer (Thermo Fisher Scientific Inc., Waltham MA). Separation of the analyte from potentially interfering material was achieved at ambient temperature using Agilent Eclipse Plus column (100×2.1 mm i.d.) packed with a 1.8 µm $C_{18}$ stationary phase. The mobile phase used was composed of 0.1% Formic Acid (FA) in Acetonitrile (ACN) and 0.1% Formic Acid in $H_2O$ with gradient elution, starting with 10% organic linearly increasing to 99% at 2 min, maintaining at 99% (2-2.5 min), re-equilibrating to 10% by 2.7 min and maintaining 10% organic until the end of the run. The total run time for each analyte was 5.00 min.

Calibration curves for all test compounds were computed using the ratio of the peak area of analyte to the internal standard by using a quadratic regression with 1/x weighting. The parameters of each calibration curve were used to back-calculate concentrations and to obtain values for the QC samples and unknown samples by interpolation.

FIGS. 5A1 and 5A2 disclose the rat pharmacokinetic results for each enantiomer of compound 29 orally administered at 10 mg/kg. FIGS. 5B1 and 5B2 show each enantiomer of compound 19 orally administered at 10 mg/kg. All compounds were orally bioavailable, with (R)- and (S)-29 achieving maximum plasma concentration ($C_{max}$) of 454.4±58.8 pmol/mL and 226.4±28.9 pmol/mL, respectively, at 4 h ($T_{max}$) post administration. In contrast, brain concentrations were higher with Cmax values of 1796.6±228 pmol/g and 959.9±53.3 pmol/g for (R)-29 and (S)-29 enantiomers, respectively. Similarly, the overall exposure calculated from area under the curve ($AUC_{0-t}$) was higher for both the enantiomers in brain versus plasma, with a corresponding brain to plasma (b/p) ratio of 3.8 and 4.1 for (R)-29 and (S)-29, respectively.

Likewise, (R)-19 and (S)-19 achieved a plasma $C_{max}$ of 305.5±112.8 pmol/mL and 600.6±108.1 pmol/mL and a brain $C_{max}$ of 3850±513.7 pmol/g and 3666.7±312.7 pmol/g respectively. The corresponding plasma exposures ($AUC_{0-t}$) for (R)-19 and (S)-19 were 1985±278.6 h*pmol/mL and 2678±207.5 h*pmol/mL and brain exposures were 21608±1411 h*pmol/g and 16665±1205 h*pmol/g, respectively. Significant brain/plasma ratios for (R)-19 (~11) and (S)-19 (~6), suggests excellent brain penetrability.

Overall, (R)-29 showed higher exposures in the brain and plasma when compared to the (S)-29 enantiomer, whereas exposure levels were mostly similar in the case of the (R)-19 and (S)-19 enantiomers. The brain to plasma ratios ($AUC_{brain}/AUC_{plasma}$) of R- and S-enantiomers of 29 and 19 were significant (>3), suggesting excellent brain penetration, with (R)-19 having the highest at brain exposures (b/p ratio ~11).

Example 6. Study of the Effect of Compound (±)-29 on Thermal Response in Rats

Methods: Compound (±)-29 was administered 15 minutes before saline or oxycodone challenge at 5 mg/kg, 15 mg/kg, and 25 mg/kg. Tests were performed after the rat was placed inside a transparent circular cage on a hot plate (52±0.2° C.). Licking the hind paw or jumping was considered as a sign of thermal nociception. The rat was then immediately removed from the hot plate and the time latency was recorded. Compound (±)-29 pretreatment showed no significant effects on animal's thermal response tested 30 minutes following either saline (1 ml/kg, i.p.) or oxycodone (2 mg/kg, i.p.) challenge. Thus, the compound was found to block the reinforcing effects of oxycodone that can lead to addiction, it will not prevent analgesia produced by the drug.

Figure 6A:
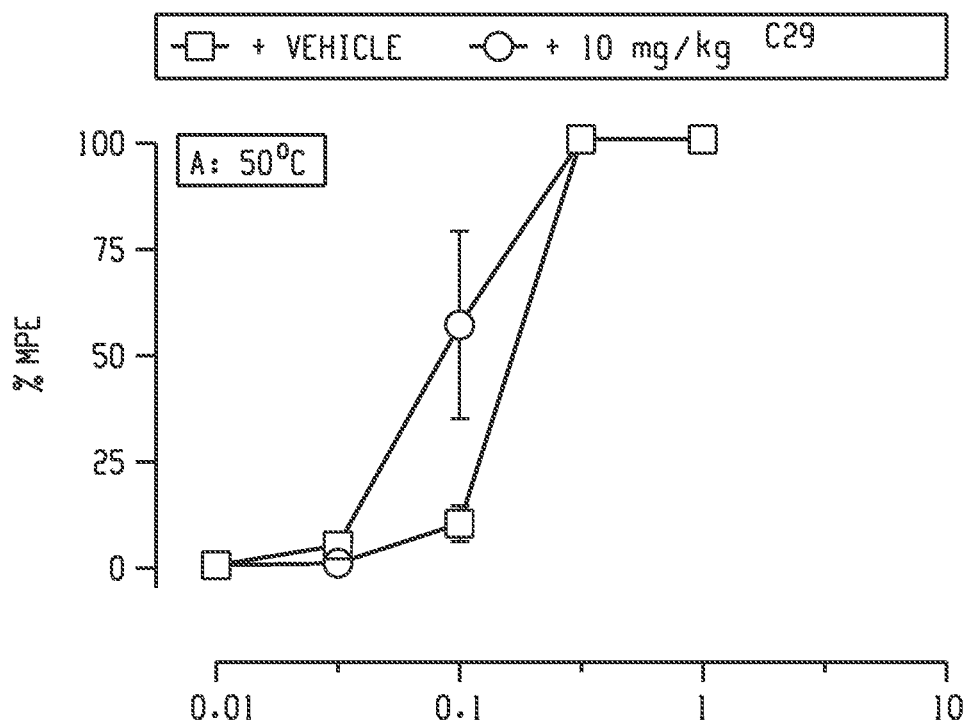
FIG. 6A: Compound (±)-29 potentiates the analgesic effects of a submaximal dose of oxycodone (0.1 mg/kg) but otherwise has no deleterious effects on oxycodone antinociception in rhesus monkey, as the opioid antagonist, naltrexone, does (FIG. 6B).
Figure 6B:
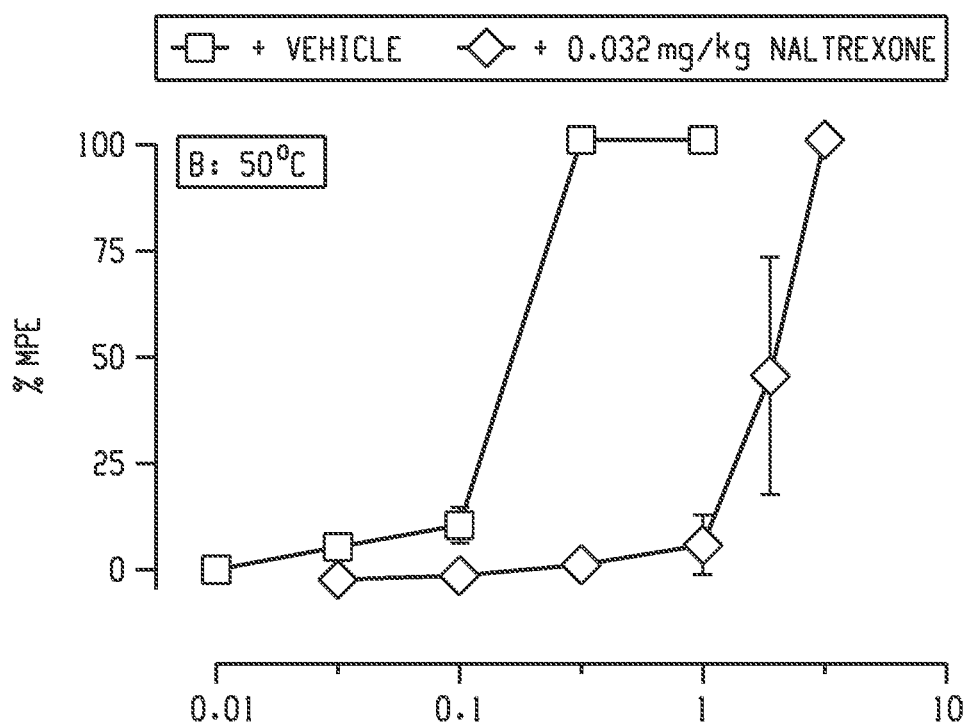

In an experiment in rhesus monkeys compound (±)-29 administered at 10 mg/kg, intramuscularly (i.m.) was found to have no effect on oxycodone antinociception at the highest and lowest doses of oxycodone. However, at the submaximal dose of 0.1 mg/kg oxycodone, compound (±)-29 potentiated antinociception in the thermal tail withdrawal model (FIG. 6A). These data suggest that D3 antagonists/partial agonists, exemplified by (±)-29 may be used with a prescription opioid to achieve analgesia at a lower dose of the opioid, decreasing the need for dose escalation and thus decreasing the development of opioid dependence.

Compound (±)-29 is a metabolically stable $D_3R$ antagonist that demonstrates high $D_3R$ binding affinity, ($K_i$=7 nM) and ~1700-fold selectivity over $D_2$ receptors. Compound (±)-29 attenuates self-administration of the prescription opioid oxycodone, in rats (FR-1, 15-25 mg/kg), significantly attenuates the acquisition of oxycodone self-administration when pretreated with compound (±)-29 and blocks oxycodone-induced reinstatement to drug seeking. Compound (±)-29 also significantly attenuates naloxone-precipitated conditioned place aversion in chronic oxycodone treated rats, but does not adversely affect oxycodone-induced analgesia, and potentiates the effects of subthreshold doses of oxycodone in both the rat hot plate test (25 mg/kg, i.p.) and the rhesus monkey (10 mg/kg, i.m.) thermal tail withdrawal test. These antinociception data in nonhuman primates suggests translational potential. Based on these findings compound (±)-29, specifically the R-enantiomer of compound 29 ("R-29"), and other selective dopamine D3 receptor antagonist compounds may serve as an effective agent for mitigating the development of prescription opioid addiction, reducing the severity of withdrawal and preventing relapse.

Example 7. Clinical Studies

The R-enantiomer of compound 29 ("R-29") will be the subject of one or more clinical studies to determine if R-29 can reduce the development of dependence to a prescription opioid, such as oxycodone, for the treatment of post-operative pain. Not wishing to be bound by theory, but it is hypothesized that if given with oxycodone, 1) the development of dependence will be mitigated over a period of 4 weeks and 2) the analgesic effects of oxycodone will either be unaffected or augmented such that tolerance does not develop and thus higher doses of oxycodone are not required for pain management.

The terms "a" and "an" do not denote a limitation of quantity, but rather denote the presence of at least one of the referenced item. The term "or" means "and/or". Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. The modifier "about" used in connection with a quantity is inclusive of the stated value and has the meaning dictated by the context (e.g., includes the degree of error associated with measurement of the particular quantity).

The endpoints of all ranges directed to the same component or property are inclusive of the endpoints, are independently combinable, and include all intermediate points and ranges (e.g., ranges of "up to about 25 wt. %, or, more specifically, about 5 wt. % to about 20 wt. %," is inclusive of the endpoints and all intermediate values of the ranges of "about 5 wt. % to about 25 wt. %," such as about 10 wt % to about 23 wt %, etc.).

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of treating pain, comprising providing to a human in need thereof a therapeutically effective amount of an opioid analgesic or a pharmaceutically acceptable salt thereof and a therapeutically effective amount of a compound of Formula (I), a stereoisomer thereof, or a pharmaceutically acceptable salt thereof

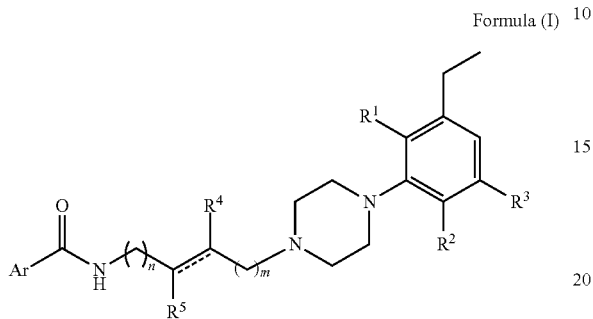

Formula (I)

wherein
Ar is a heteroaryl which may be optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, mono- or di-$C_1$-$C_3$alkylamino, or halogen, or Ar is a 3,4-methylenedioxy-phenyl group;
n is 1 or 2;
m is 1 or 2;
$R^1$ is H or halogen;
$R^2$ is H, $C_1$-$C_3$alkoxy, or halogen;
$R^3$ is H, halogen or $C_1$-$C_3$alkoxy;
$R^4$ is H, —OH, or halogen;
$R^5$ is H, —OH, or halogen; and
═══ is a single bond or a double bond,
with the provisos a) and b) for Formula (I)
a) when $R^1$ is H then at least one of $R^2$ and $R^3$ is not H; and
b) when one or both of $R^2$ and $R^3$ is H then $R^1$ is not H.

2. The method of claim 1, wherein
a.) $R^1$ is H; $R^2$ is —OMe; and $R^3$ is Cl;
b.) $R^1$ is Cl; $R^2$ is H; and $R^3$ is H;
c.) $R^1$ is H; $R^2$ is —OMe; $R^3$ is Cl; and Ar is benzofuranyl, benzothienyl, imidazolyl, imidazo[1,2-a]pyridinyl, imidazo[2,1-b]thiazolyl, or indolyl, where Ar is further optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$aloalkoxy, —OH, —COOH, amino, nitro, $C_2$-$C_3$alkanoyl group, or halogen;
d.) $R^1$ is Cl; $R^2$ is H; $R^3$ is H; and Ar is benzofuranyl, benzothienyl, imidazolyl, imidazo[1,2-a]pyridinyl, imidazo[2,1-b]thiazolyl, or indolyl, where Ar is further optionally substituted with 1, 2, or 3 substituents where each substituent independently is $C_1$-$C_6$alkyl, $C_1$-$C_6$haloalkyl, $C_1$-$C_6$alkoxy, $C_1$-$C_6$haloalkoxy, —OH, —COOH, amino, nitro, $C_2$-$C_3$alkanoyl group, or halogen;
e.) $R^1$ is H; $R^2$ is —OMe; $R^3$ is Cl; Ar is benzofuranyl, 4-ethyl-1H-imidazolyl, 4-methyl-1H-imidazolyl, imidazo[1,2-a]pyridinyl, 6-methylimidazo[2,1-b]thiazolyl, or indolyl; m is 1; and n is 1;
f.) $R^1$ is Cl; $R^2$ is H; $R^3$ is H; Ar is benzofuranyl, 4-ethyl-1H-imidazolyl, 4-methyl-1H-imidazolyl, imidazo[1,2-a]pyridinyl, 6-methylimidazo[2,1-b]thiazolyl, or indolyl; m is 1; and n is 1;
g.) $R^1$ is H; $R^2$ is —OMe; $R^3$ is Cl; Ar is benzofuranyl, 4-ethyl-1H-imidazolyl, 4-methyl-1H-imidazolyl, imidazo[1,2-a]pyridinyl, 6-methylimidazo[2,1-b]thiazolyl, or indolyl; and one of $R^4$ and $R^5$ is H and the other is —OH or —F;
h.) $R^1$ is Cl; $R^2$ is H; $R^3$ is H; Ar is benzofuranyl, 4-ethyl-1H-imidazolyl, 4-methyl-1H-imidazolyl, imidazo[1,2-a]pyridinyl, 6-methylimidazo[2,1-b]thiazolyl, or indolyl; and one of $R^4$ and $R^5$ is H and the other is —OH or —F;
i.) $R^1$ is H; $R^2$ is —OMe; $R^3$ is Cl; Ar is benzofuranyl or indolyl; n is 1 or 2; m is 1 or 2; $R^4$ is H, —OH, or halogen; and $R^5$ is H, —OH, or halogen; or
j.) $R^1$ is Cl; $R^2$ is H; $R^3$ is H; Ar is benzofuranyl or indolyl; n is 1 or 2; m is 1 or 2; $R^4$ is H, —OH, or halogen; and $R^5$ is H, OH, or halogen.

3. The method of claim 1, wherein the compound of Formula (I) is
N-(4-(4-(2-Chloro-3-ethylphenyl)piperazin-1-yl)butyl)-1H-indole-2-carboxamide (18);
N-(4-(4-(2-Chloro-3-ethylphenyl)piperazin-1-yl)-3-hydroxybutyl)-1H-indole-2-carboxamide (19);
N-(4-(4-(2-Chloro-3-ethylphenyl)piperazin-1-yl)butyl)benzofuran-2-carboxamide (20);
N-(4-(4-(2-Chloro-3-ethylphenyl)piperazin-1-yl)-3-hydroxybutyl)benzofuran-2-carboxamide (21);
N-(4-(4-(2-chloro-3-ethylphenyl)piperazin-1-yl)butyl)imidazo[1,2-a]pyridine-2-carboxamide (22);
N-(4-(4-(2-Chloro-3-ethylphenyl)piperazin-1-yl)-3-hydroxybutyl)imidazo[1,2-a]pyridine-2-carboxamide (23);
N-(4-(4-(2-chloro-3-ethylphenyl)piperazin-1-yl)butyl)-6-methylimidazo[2,1-b]thiazole-5-carboxamide (24);
N-(4-(4-(2-Chloro-3-ethylphenyl)piperazin-1-yl)butyl)-4-ethyl-1H-imidazole-2-carboxamide (25);
N-(4-(4-(2-Chloro-3-ethylphenyl)piperazin-1-yl)butyl)-4-methyl-1H-imidazole-2-carboxamide (26);
N-(4-(4-(2-Chloro-3-ethylphenyl)piperazin-1-yl)-3-hydroxybutyl)-4-methyl-1H-imidazole-2-carboxamide (27);
N-(4-(4-(3-Chloro-5-ethyl-2-methoxyphenyl)piperazin-1-yl)butyl)-1H-indole-2-carboxamide (28);
N-(4-(4-(3-chloro-5-ethyl-2-methoxyphenyl)piperazin-1-yl)-3-hydroxybutyl)-1H-indole-2-carboxamide (29);
N-(4-(4-(3-Chloro-5-ethyl-2-methoxyphenyl)piperazin-1-yl)butyl)benzofuran-2-carboxamide (30);
N-(4-(4-(3-Chloro-5-ethyl-2-methoxyphenyl)piperazin-1-yl)-3-hydroxybutyl)benzofuran-2-carboxamide (31);
(E)-N-(4-(4-(2-Chloro-3-ethylphenyl)piperazin-1-yl)but-2-en-1-yl)-4-methyl-1H-imidazole-2-carboxamide (35);
N-(4-(4-(2-Chloro-3-ethylphenyl)piperazin-1-yl)-2-hydroxybutyl)-1H-indole-2-carboxamide (40);
N-(4-(4-(3-chloro-5-ethyl-2-methoxyphenyl)piperazin-1-yl)-3-fluorobutyl)-1H-indole-2-carboxamide (C4a);
N-(4-(4-(3-Chloro-5-ethyl-2-methoxyphenyl)piperazin-1-yl)-3-fluorobutyl)benzofuran-2-carboxamide (C4b);
N-(4-(4-(2-chloro-3-ethylphenyl)piperazin-1-yl)-3-fluorobutyl)-1H-indole-2-carboxamide (C5a);
N-(4-(4-(2-Chloro-3-ethylphenyl)piperazin-1-yl)-3-fluorobutyl)benzofuran-2-carboxamide (C5b);

N-(4-(4-(3-Chloro-5-ethyl-2-methoxyphenyl)piperazin-1-yl)-3-hydroxybutyl)benzo[d][1,3]dioxole-5-carboxamide (113a);

N-(4-(4-(2-Chloro-3-ethylphenyl)piperazin-1-yl)-3-hydroxybutyl)benzo[d][1,3]dioxole-5-carboxamide (113b);

N-(4-(4-(6-Ethylbenzo[d][1,3]dioxol-5-yl)piperazin-1-yl)-3-hydroxybutyl)-1H-indole-2-carboxamide (121);

N-(4-(4-(6-Ethylbenzo[d][1,3]dioxol-5-yl)piperazin-1-yl)-3-hydroxy butyl)benzofuran-2-carboxamide (122);

a stereoisomer thereof; or a pharmaceutically acceptable salt thereof.

4. The method of claim 1, wherein the compound of Formula (I) is

N-(4-(4-(3-chloro-5-ethyl-2-methoxyphenyl)piperazin-1-yl)-3-hydroxybutyl)-1H-indole-2-carboxamide;

(R)—N-(4-(4-(3-chloro-5-ethyl-2-methoxyphenyl)piperazin-1-yl)-3-hydroxybutyl)-1H-indole-2-carboxamide;

(S)—N-(4-(4-(3-chloro-5-ethyl-2-methoxyphenyl)piperazin-1-yl)-3-hydroxybutyl)-1H-indole-2-carboxamide;

N-(4-(4-(2-chloro-3-ethylphenyl)piperazin-1-yl)-3-hydroxybutyl)-1H-indole-2-carboxamide;

(R)—N-(4-(4-(2-chloro-3-ethylphenyl)piperazin-1-yl)-3-hydroxybutyl)-1H-indole-2-carboxamide;

(S)—N-(4-(4-(2-chloro-3-ethylphenyl)piperazin-1-yl)-3-hydroxybutyl)-1H-indole-2-carboxamide;

N-(4-(4-(3-chloro-5-ethyl-2-methoxyphenyl)piperazin-1-yl)-3-fluorobutyl)-1H-indole-2-carboxamide;

(R)—N-(4-(4-(3-chloro-5-ethyl-2-methoxyphenyl)piperazin-1-yl)-3-fluorobutyl)-1H-indole-2-carboxamide;

(S)—N-(4-(4-(3-chloro-5-ethyl-2-methoxyphenyl)piperazin-1-yl)-3-fluorobutyl)-1H-indole-2-carboxamide;

N-(4-(4-(3-chloro-5-ethyl-2-methoxyphenyl)piperazin-1-yl)-3-fluorobutyl)benzofuran-2-carboxamide;

(R)—N-(4-(4-(3-chloro-5-ethyl-2-methoxyphenyl)piperazin-1-yl)-3-fluorobutyl)benzofuran-2-carboxamide;

(S)—N-(4-(4-(3-chloro-5-ethyl-2-methoxyphenyl)piperazin-1-yl)-3-fluorobutyl)benzofuran-2-carboxamide;

N-(4-(4-(2-chloro-3-ethylphenyl)piperazin-1-yl)-3-fluorobutyl)-1H-indole-2-carboxamide;

(R)—N-(4-(4-(2-chloro-3-ethylphenyl)piperazin-1-yl)-3-fluorobutyl)-1H-indole-2-carboxamide;

(S)—N-(4-(4-(2-chloro-3-ethylphenyl)piperazin-1-yl)-3-fluorobutyl)-1H-indole-2-carboxamide;

N-(4-(4-(2-chloro-3-ethylphenyl)piperazin-1-yl)-3-fluorobutyl)benzofuran-2-carboxamide;

(R)—N-(4-(4-(2-chloro-3-ethylphenyl)piperazin-1-yl)-3-fluorobutyl)benzofuran-2-carboxamide;

(S)—N-(4-(4-(2-chloro-3-ethylphenyl)piperazin-1-yl)-3-fluorobutyl)benzofuran-2-carboxamide; or a pharmaceutically acceptable salt thereof.

5. The method of claim 1, wherein the compound of Formula (I) is N-(4-(4-(3-Chloro-5-ethyl-2-methoxyphenyl)piperazin-1-yl)-3-hydroxybutyl)-1H-indole-2-carboxamide, (R)—N-(4-(4-(3-chloro-5-ethyl-2-methoxyphenyl)piperazin-1-yl)-3-hydroxybutyl)-1H-indole-2-carboxamide, or (S)—N-(4-(4-(3-chloro-5-ethyl-2-methoxyphenyl)piperazin-1-yl)-3-hydroxybutyl)-1H-indole-2-carboxamide.

6. The method of claim 1, wherein the opioid analgesic is bremazocine, butorphanol, carfentanyl, codeine, cyclazocine, dezocine, diamorphine, dihydrocodeine, dihydromorphine, dihydromorphinone (aka hydromorphone), enadoline, eseroline, ethylmorphine, etonitazine, etorphine, fentanyl, hydrocodone, levophenacylmorphan, levorphanol, meperidine/pethidine, morphine, nalbuphine, nicomorphine, oxycodone, oxymorphone, pentazocine, phenazocine, picenadol, tramadol, tapentadol, or a combination thereof.

7. The method of claim 1, wherein the opioid analgesic is oxycodone.

8. The method of claim 1, comprising providing the compound of Formula (I) at least once daily to the human for one or more weeks.

9. The method of claim 1, comprising providing the compound of Formula (I) to the human daily starting 1, 2, 3, 4, 5, 6, 7, 8, 9, 10, or more days prior to the initiation of opioid analgesic administration.

10. The method of claim 1, comprising providing the compound of Formula (I) to the human at least once daily for the duration of time of the opioid analgesic therapy, and optionally further providing the compound of Formula (I) to the human at least once daily for 1, 2, 3, 4, 5, 6, 7, 8, 9, 10, or more days after discontinuation of the opioid analgesic therapy.

11. The method of claim 1, comprising
providing the compound of Formula (I) to the human at least once daily starting 1, 2, 3, 4, 5, 6, 7, 8, 9, 10, or more days prior to the initiation of opioid analgesic administration;
providing the compound of Formula (I) to the human at least once daily for the duration of time of the opioid analgesic therapy, and
optionally further providing the compound of Formula (I) to the human at least once daily for 1, 2, 3, 4, 5, 6, 7, 8, 9, 10, or more days after discontinuation of the opioid analgesic therapy.

12. The method of claim 1, wherein the opioid analgesic and the compound of Formula (I) are formulated as a single pharmaceutical composition further comprising at least one pharmaceutically acceptable carrier, or formulated as separate pharmaceutical compositions, each further comprising at least one pharmaceutically acceptable carrier.

13. The method of claim 12, wherein the single pharmaceutical composition or each separate pharmaceutical composition independently is formulated for oral, topical, or parenteral administration.

14. The method of claim 12, wherein the single pharmaceutical composition or each separate pharmaceutical composition independently is an intravenous formulation, an injectable formulation, a subcutaneous formulation, an aerosol, a cream, a gel, a tablet, a capsule, a syrup, an ophthalmic solution, or a transdermal patch.

15. The method of claim 12, wherein one or more of the single pharmaceutical composition or separate pharmaceutical compositions are provided in a kit further comprising instructions for using the pharmaceutical composition in order to treat the human.

16. The method of claim 1, wherein
the compound of Formula (I) is N-(4-(4-(3-chloro-5-ethyl-2-methoxyphenyl)piperazin-1-yl)-3-hydroxybutyl)-1H-indole-2-carboxamide or (R)—N-(4-(4-(3-chloro-5-ethyl-2-methoxyphenyl)piperazin-1-yl)-3-hydroxybutyl)-1H-indole-2-carboxamide, and the opioid analgesic is oxycodone.

17. The method of claim 1, further comprising providing a Medication Assisted Treatment agent to the human, wherein the Medication Assisted Treatment agent is methadone, buprenorphine, naloxone, naltrexone, levo-alpha acetyl methadol, or a combination thereof.

* * * * *